US011667917B2

(12) United States Patent
Kim et al.

(10) Patent No.: US 11,667,917 B2
(45) Date of Patent: Jun. 6, 2023

(54) COMPOSITION FOR GENOME EDITING USING CRISPR/CPF1 SYSTEM AND USE THEREOF

(71) Applicant: Genkore Co. Ltd., Daejeon (KR)

(72) Inventors: Yong Sam Kim, Daejeon (KR); Jeong Heon Ko, Daejeon (KR); Jeong Mi Lee, Daejeon (KR); Su Bin Moon, Daejeon (KR)

(73) Assignee: GENKORE CO. LTD., Daejeon (KR)

( * ) Notice: Subject to any disclaimer, the term of this patent is extended or adjusted under 35 U.S.C. 154(b) by 393 days.

(21) Appl. No.: 16/765,553

(22) PCT Filed: Nov. 21, 2018

(86) PCT No.: PCT/KR2018/014312
§ 371 (c)(1),
(2) Date: May 20, 2020

(87) PCT Pub. No.: WO2019/103442
PCT Pub. Date: May 31, 2019

(65) Prior Publication Data

US 2020/0308583 A1 Oct. 1, 2020

(30) Foreign Application Priority Data

Nov. 21, 2017 (KR) ........................ 10-2017-0155927

(51) Int. Cl.
*C12N 15/113* (2010.01)
*C12N 9/22* (2006.01)
*C12N 15/82* (2006.01)
*C12N 15/85* (2006.01)
*C12N 9/96* (2006.01)

(52) U.S. Cl.
CPC .............. *C12N 15/113* (2013.01); *C12N 9/22* (2013.01); *C12N 9/96* (2013.01); *C12N 15/8201* (2013.01); *C12N 15/8509* (2013.01); *C12N 2310/20* (2017.05); *C12N 2310/3519* (2013.01)

(58) Field of Classification Search
None
See application file for complete search history.

(56) References Cited

FOREIGN PATENT DOCUMENTS

KR 10-2017-0063399 6/2017
KR 10-2017-0068400 6/2017

OTHER PUBLICATIONS

KIPO, Notice of Allowance of Application No. 10-2018-0144185 dated Oct. 13, 2020.
Michael T. McManus et al., "Trypanosoma brucei Guide RNA Poly(U) Tail Formation Is Stabilized by Cognate mRNA", Mol. Cell. Biol. vol. 20 (3):883-891(2000), Feb. 2000.
Michael T. McManus et al., "Trypanosoma brucei Guide RNA Poly(U) Tail Formation Is Stabilized by Cognate mRNA", Molecular and Cellular Biology, vol. 20, No. 3, Feb. 2000, p. 883-891.
Bin Li et al., "Engineering CRISPR-Cpf1 crRNAs and mRNAs to maximize genome editing efficiency", Nature biomedical engineering, 1(5), 0066. https://doi.org/10.1038/s41551-017-0066.
Alexandra East-Seletsky et al., "RNA Targeting by Functionally Orthogonal Type VI-A CRISPR-Cas Enzymes", Molecular Cell 66, 373-383, May 4, 2017.
Xu Tang et al., "A CRISPR-Cpf1 system for efficient genome editing and transcriptional repression in plants", Nature Plants, vol. 3, No. 3, Feb. 17, 2017, pp. 1-5, https://doi.org/10.1038/nplants.2017.18.
Su Bin Moon et al.: "Highly efficient genome editing by CRISPR-Cpf1 using CRISPR RNA with a uridinylate-rich 3'-overhang", Nature Communications, vol. 9, No. 1, Sep. 7, 2018, https://doi.org/10.1038/s41467-018-06129-w.
Dae-In Ha et al., "Highly efficient and safe genome editing by CRISPR-Cas12a using CRISPR RNA with a ribosyl-2'-O-methylated uridinylate-rich 3'-overhang in mouse zygotes", Experimental & Molecular Medicine, vol. 52, Nov. 9, 2020, pp. 1823-1830, https://doi.org/10.1038/s12276-020-00521-7.
EPO, Extended European Search Report of EP 18882084.9 dated Aug. 5, 2021.

*Primary Examiner* — Anand U Desai
(74) *Attorney, Agent, or Firm* — Lex IP Meister, PLLC

(57) ABSTRACT

The present invention relates to a composition for genome editing using a CRISPR/Cpf1 system and a use thereof and, more particularly, to a composition for genome editing comprising: a CRISPR RNA (crRNA) including a guide sequence capable of hybridizing with a target nucleotide sequence, and a uridine repeat sequence connected to the 3'-end of the guide sequence, or a DNA encoding the same; and a Cpf1 protein or a DNA encoding the same, a method for genome editing using the same, a method for construction of a genetically modified organism, and a genetically modified organism. The present invention can increase an indel efficiency and decrease off-target activity in genome editing of eukaryotic cells using the CRIPSPR/Cpf1 system and thus can easily construct a genetically modified cell or genetically modified animal or plant having a desired gene inserted thereinto (knock-in) or deleted therefrom (knock-out).

16 Claims, 39 Drawing Sheets

Specification includes a Sequence Listing.

FIG. 4

Target sequence (Amp$^R$ gene)

5'-TTTATCAGGGTTATTGTCTCATGAGCGgatacatattt-3' (SEQ ID NO: 440)

PAM 23-nt target crRNA library

Direct repeat Canonical 23-nt target sequence

UAAUUUCUACUCUUGUAGAUUCAGGGUUAUUGUCUCANNNNNNNNNNN (SEQ ID NO: 441) 3'-overhang

| Dilution factor | Number of colony |
|---|---|
| $10^5$ | 1,676 |
| $10^6$ | 144 |
| $10^7$ | 15 |
| Colony forming unit=$1.1558\times10^8$ CFU/mL | |

COMPOSITION FOR GENOME EDITING USING CRISPR/CPF1 SYSTEM AND USE THEREOF

TECHNICAL FIELD

The present invention relates to a composition for genome editing using a CRISPR/Cpf1 system and a use thereof and, more particularly, to a composition for genome editing comprising: a CRISPR RNA (crRNA) including a guide sequence complementary to a target nucleotide sequence, and a uridine (U) repeat sequence linked to the 3'-end of the guide sequence, or a DNA encoding the crRNA; and a Cpf1 protein or a DNA encoding the Cpf1 protein, a method for genome editing using the same, a method for construction of a genetically modified organism, and a genetically modified organism.

BACKGROUND ART

Genome editing refers to a method of exhibiting a desired genetic trait by freely correcting the genetic information of an organism, and has achieved remarkable development while being used in various fields from research on the function of a gene to the treatment of a disease through development of a CRISPR-associated protein (CRISPR/Cas) system.

Clustered regularly interspaced short palindromic repeats (CRISPR) are loci containing multiple short direct repeat sequences that are found in the genomes of bacteria and archaea whose gene sequences have been revealed, and functions as an acquired prokaryotic immune system that confers resistance to exogenous genetic elements such as viruses and phages. A short motif of exogenous DNA, called a protospacer, is integrated into the genome between CRISPR repeat sequences and serves to remember past exposure to external factors. The spacer of the thus integrated motif is used as a template for producing a guide RNA, and serves to cleave external invading genetic materials.

The core of CRISPR-based gene editing technology lies in the process of recognizing a specific base sequence using RNA as a medium in an organism, inducing a double strand breakage (DSB) at the corresponding gene site by an effector protein such as Cas9, and then repairing the DSB. In the process of restoring a DSB generated by a CRISPR/Cas system in eukaryotic cells, there are non-homologous end joining (NHEJ) in which random insertion and deletion (indel) occur in a truncated base sequence, and a homology directed repair (HDR) which repairs a cleavage site using a DNA strand having a base sequence identical to the vicinity of a cleaved DNA as a template. Each gene repair method enables knock-out that induces a frame shift of a specific gene caused by indel of a gene base sequence, and knock-in that induces an intended insertion or substitution of the specific base sequence in a desired gene. Therefore, an increase in DSB frequency and the accuracy are required to increase the efficiency of knock-out or knock-in of a precise location, and for this purpose, studies seeking to find out a modification method of an existing CRISPR/Cas system or a new CRISPR/Cas system have been continuously conducted.

Recently, like Cas9, Cpf1 (a Type V Cas system called CRISPR from *Prevotella* and *Francisella* 1) was found in various types of bacteria. Cpf1 belongs to Class 2, which has one protein as an effector protein, like Cas9, and under the guidance of crRNA (CRISPR RNA), the effector protein causes the DSB in the DNA by recognizing a specific protospacer-adjacent motif (PAM) sequence.

However, there is a difference in that Cas9 requires a crRNA and a trans-activating crRNA (tracrRNA) for specific base sequence recognition and cleavage, whereas Cpf1 requires only a crRNA. Further, in the PAM sequence in which the effector protein and crRNA complex recognize a specific DNA base sequence, there in a difference in that Cas9 requires a G-rich sequence, whereas Cpf1 recognizes a T-rich sequence. Even in the form of DSB generated in this case, Cas9 is cleaved into a blunt end in the site close to the PAM, whereas Cpf1 is cleaved into a staggered end 18-23 nucleotides (nt) away from the PAM. Further, Cpf1 has a smaller gene size than Cas9, and thus is expected to be more useful for clinical purposes.

The aforementioned features of Cpf1 may act as advantages in gene therapy. In particular, features of Cpf1, which requires proteins and crRNAs which are relatively small in size compared to Cas9, may be enormously advantageous, in that when a genetic material used for gene editing into the human body is delivered using a virus such as an adeno-associated virus (AAV), the size of the genetic material that can be delivered is limited. In addition, the fact that the off-target result of Cpf1 is low compared to Cas9 is an important advantage even in terms of stability of gene therapy. However, since it has been found to date that the indel efficiency of Cpf1 is relatively lower than that of Cas9 or that there is a large deviation depending on the gene to be targeted, it is difficult to replace Cas9. Therefore, in order to replace or surpass Cas9 while maximizing the advantages of Cpf1, it is essential to develop a method for increasing the indel efficiency of Cpf1.

The indel efficiency or accuracy of a target gene may be increased by manipulating an effector endonuclease or guide RNA in the CRISPR/Cas system, and in the case of Cas9, such studies have been actively conducted, whereas studies on the Cpf1 system are insufficient.

DETAILED DESCRIPTION OF THE INVENTION

Technical Problem

Thus, as a result of intensive studies to develop a CRISPR/Cpf1 system capable of overcoming the disadvantages of the CRISPR/Cas9 system, the present inventors have found that the indel efficiency is improved as compared to the Cpf1 system with crRNA and Cas9 system in the related art by adding a uridine repeat sequence to the 3'-terminal sequence of the crRNA used for the CRISPR/Cpf1 system, thereby completing the present invention.

An object of the present invention is to provide a polynucleotide consisting of a uridine (U) repeat nucleotide sequence linked to the 3'-end of a guide sequence complementary to a target nucleotide sequence in a CRISPR/Cpf1 system.

Another object of the present invention is to provide a composition for genome editing comprising: a CRISPR RNA (crRNA) including a guide sequence complementary to a target nucleotide sequence and a uridine (U) repeat sequence linked to the 3'-end of the guide sequence, or a DNA encoding the crRNA; and a Cpf1 protein or a DNA encoding the Cpf1 protein.

Still another object of the present invention is to provide a method for genome editing, the method including: introduction of the composition for genome editing into an isolated cell or organism.

Yet another object of the present invention is to provide a method for construction of a genetically modified organism, the method including: introduction of the composition for genome editing into an isolated cell or organism.

Still yet another object of the present invention is to provide a genetically modified organism constructed by the method.

Technical Solution

An aspect of the present invention provides a polynucleotide consisting of a uridine (U) repeat nucleotide sequence linked to the 3'-end of a guide sequence complementary to a target nucleotide sequence in a CRISPR/Cpf1 system.

Another aspect of the present invention provides a composition for genome editing comprising: a CRISPR RNA (crRNA) including a guide sequence complementary to a target nucleotide sequence, a uridine repeat sequence linked to the 3'-end of the guide sequence, or a DNA encoding the crRNA; and a Cpf1 protein or a DNA encoding the Cpf1 protein.

Still another aspect of the present invention provides a method for genome editing, the method including: introduction of the composition for genome editing into an isolated cell or organism.

Yet another aspect of the present invention provides a method for construction of a genetically modified organism, the method including: introduction of the composition for genome editing into an isolated cell or organism.

Still yet another aspect of the present invention provides a genetically modified organism constructed by the method.

Advantageous Effects

The present invention can increase an indel efficiency and decrease off-target activity in genome editing of eukaryotic cells using the CRIPSPR/Cpf1 system and thus can easily construct a genetically modified cell or genetically modified animal or plant having a desired gene inserted thereinto (knock-in) or deleted therefrom (knock-out).

BRIEF DESCRIPTION OF THE DRAWINGS

FIGS. 1 to 14 illustrate the results of in vitro experiments confirming that crRNAs (U-rich crRNAs) with a U-repeat sequence at the 3'-end increase the dsDNA cleavage efficiency of Cpf1:

FIG. 1 illustrates the results of confirming the difference in indel efficiency of AsCpf1 in vivo according to mutation of the 3 nucleotide sequences at the 3'-end of crRNA.

FIG. 2 illustrates the results of confirming the effects of the U3 end on the indel efficiency depending on the target (DNMT1, LGALS3BP, and VEGFA).

FIG. 3 illustrates the results of confirming the increase in dsDNA cleavage efficiency of AsCpf1 by U-rich crRNA at the 3'-end depending on the reaction time and conditions.

FIG. 4 is a view illustrating an ampicillin resistance gene target sequence and a crRNA library sequence.

FIG. 5 is a set of photographs illustrating colonies of BL21 (DE3) *E. coli* transformed with a pET21 plasmid vector in which an oligonucleotide library is cloned using a sequence- and ligation-independent cloning method (Li & Elledge, Methods Mol Biol, 2012) according to the colony forming unit (CFU).

FIG. 6 is a view illustrating a schematic view of an unbiased in vitro experiment method for searching for an optimal crRNA arrangement.

FIG. 7 illustrates the results of deep sequencing data analysis confirming that a crRNA-coding plasmid DNA library was prepared such that A, T, G and C accounted for almost the same molar ratio at each position.

FIG. 8 illustrates the results of calculating the probability value from the inverted value of the nucleotide ratio at each position exhibiting the optimal crRNA arrangement.

FIG. 9 illustrates the results of confirming the change in activity of AsCpf1 according to the length of the 3'-terminal uridine sequence of crRNA.

FIG. 10 is a schematic view illustrating an in vitro experimental method for analyzing the dsDNA cleavage activity.

FIG. 11 illustrates the results of verifying that the activity of AsCpf1 is enhanced by the U-rich 3'-overhang in crRNA (mean±standard deviation, compared to the case of *; $p<0.05$, **; $p<0.01$, $U_8$ (n=3)).

FIG. 12 is a schematic view illustrating an experimental design for confirming the optimal arrangement of the crRNA.

FIG. 13 illustrates the results showing that the number of reads and the efficiency of crRNA are inversely proportional.

FIG. 14 illustrates the results of confirming that crRNAs having a U8 3'-overhang exhibit an optimal AsCpf1 activity through standardization of reads.

FIG. 15 is a conceptual view schematically illustrating an in vivo analysis method for determining an optimal structure of crRNA according to the present invention.

FIG. 16 illustrates the results of confirming the improved indel efficiency by the U-rich 3'-overhang sequence according to the present invention (mean±standard deviation; exhibiting representative results after repeated experiments three times, respectively).

FIG. 17 illustrates the results of confirming that the improvement of the indel efficiency by the 3'-terminal U-rich guide RNA specifically appears in Cpf1 unlike Cas9 (mean±standard deviation; exhibiting representative results after repeated experiments three times, respectively).

FIG. 18 illustrates the results of confirming the change in indel efficiency of AsCpf1 according to an increase in uridine length.

FIG. 19 illustrates the results of confirming the difference in indel efficiency depending on the 3'-terminal sequence of crRNA (*;$p>0.05$, ;$p<0.05$, *;$p<0.01$, n=3).

FIG. 20 illustrates the results of confirming the optimal target length of uridine for U-rich crRNA.

FIG. 21 illustrates the results of verifying the optimal crRNA structure for improving the genome efficiency in the CRISPR/Cpf1 system (mean±standard deviation; exhibiting representative results after repeated experiments three times, respectively).

FIG. 22 schematically illustrates that dsDNA cleavage at the DNMT1 position appears in the presence of crRNA and donor DNA.

FIG. 23 illustrates the results of confirming indel and knock-in efficiencies at the target site after indel mutation was caused by the CRISPR/Cpf1 system.

FIG. 24 illustrates the results of targeting the same site with AsCpf1 and SpCas9.

FIG. 25 illustrates the results of showing the indel efficiencies of AsCpf1 and SpCas9 confirmed for the same target gene in HEK-293T cells by a dot plot, and FIG. 26 illustrates the results by a Box-Whisker plot.

FIG. 27 illustrates the results of deep-sequencing comparing the off-target activities of the crRNA sequence in the related art and the U-rich crRNA sequence at potential off-target sites.

FIG. 28 illustrates the results of comparing the off-target activities of a crRNA in the related art and the U-rich crRNA, which have one mismatched base with the on-target sequence.

FIG. 29 illustrates the results confirming that 98% or more of the genomic DNA was degraded by not only AsCpf1-U-rich crRNA but also the AsCpf1-standard crRNA ribonucleoprotein complex.

FIG. 30 illustrates the results of confirming typical cleavage patterns at positions 18-20 of the non-target strand and at position 22 of the target strand through an integrated genomic viewer (IGV).

FIG. 31 illustrates the results of showing off-target sites where the DNA cleavage scores and discrepancies of Con-crRNA and U-rich-crRNA were confirmed to be 2.5 or more and 6 or less in a whole genome Circosplot.

FIG. 32 illustrates the number of off-target sites and the number of common off-target sites respectively confirmed for the standard and the U-rich crRNA by a diagram.

FIG. 33 is a view illustrating the same off-target pattern of the whole genome Circos plot in the standard and the U-rich crRNA.

FIG. 34 illustrates the results confirming that the indel efficiencies of multiple targets are simultaneously increased by a plurality of U-rich crRNAs.

FIGS. 35 and 36 illustrate that U-rich crRNA is applied to the AsCpf1 PAM variant (*;p>0.001, **;p<0.01, n=3).

FIG. 37 illustrates the results of showing the levels of crRNA by performing Northern blot analysis in order to confirm whether the increased Cpf1 activity was due to improved stability of the crRNA or to direct regulation of Cpf1.

FIG. 38 illustrates the results showing that the chemically modified U-rich crRNA shows much higher Cpf1 activity than the chemically modified standard crRNA, but no significant difference for the chemically modified guide RNA for Cas9.

FIG. 39 illustrates results that the 63-nt length is the minimum length at which a decrease in activity of tracrRNA is not shown, and the presence of U4AU4 does not induce increased Cas9 activity at this length.

FIG. 40 illustrates the results confirming that U-rich crRNA significantly increases the binding affinity to AsCpf1 compared to the standard crRNA, but that U-rich sgRNA does not cause a significant difference in the binding strength to SpCas9 complex.

FIG. 41 illustrates the results of performing an isothermal titration calorimetry (ITC) analysis on U-rich and standard crRNA, respectively.

BEST MODE

Figure 1:
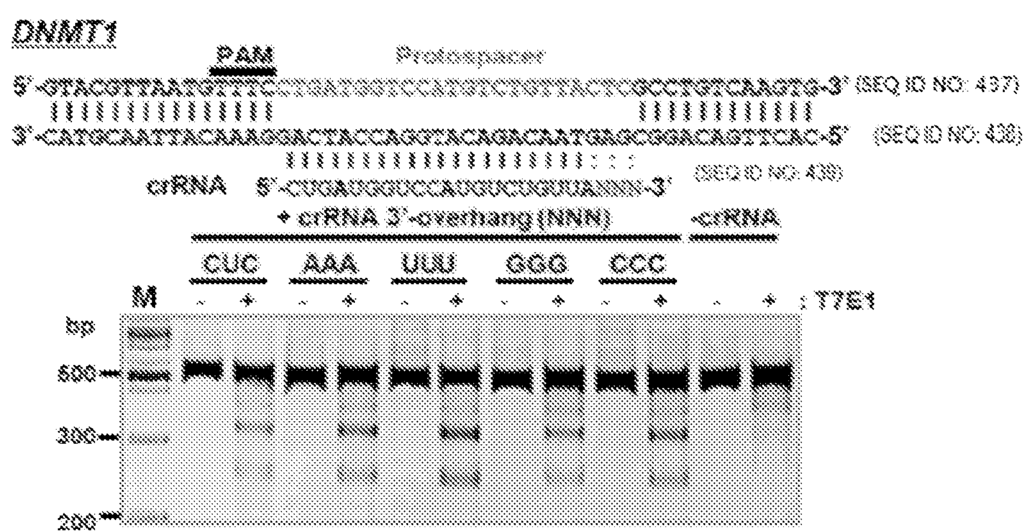

The present invention has been made in an effort to solve the above-described problems, and provides a polynucleotide consisting of a uridine (U) repeat nucleotide sequence linked to the 3'-end of a guide sequence capable of hybridizing with(complementary to) a target nucleotide sequence in a CRISPR/Cpf1 system. Further, the present invention provides a composition for genome editing comprising: a CRISPR RNA (crRNA) including a guide sequence capable of hybridizing with a target nucleotide sequence and a uridine repeat sequence linked to the 3'-end of the guide sequence, or a DNA encoding the crRNA; and a Cpf1 protein or a DNA encoding the Cpf1 protein.

As used herein, the term 'genome editing' refers to the loss, alteration, and/or repair (correction) of the gene function by the deletion, insertion, substitution, and the like of one or more nucleic acid molecules (for example, 1 to 100,000 bp, 1 to 10,000 bp, 1 to 1,000 bp, 1 to 100 bp, 1 to 70 bp, 1 to 50 bp, 1 to 30 bp, 1 to 20 bp, or 1 to 10 bp) by cleavage at a target site of a target gene, unless otherwise specifically mentioned. According to an exemplary embodiment, the cleavage at a desired position of a target DNA is enabled by a type V CRISPR/Cpf1 system using a Cpf1 protein, and according to another exemplary embodiment, a specific gene in cells can be corrected by a type V CRISPR/Cpf1 system using a Cpf1 protein.

In addition, a method for overcoming the disadvantages of the existing microinjection method is provided in the technology for delivering CRISPR/Cpf1 ribonucleoprotein (RNP) or a DNA encoding the RNP to cells. As an example of such a method, there is provided a technology of editing the genome by incorporating a ribonucleoprotein or a DNA encoding the ribonucleoprotein into a plasmid and the like and delivering the plasmid to a large number of cells at one time by electroporation, lipofection, and the like, but the genome editing technology using the Cpf1 system is not limited thereto.

The CRISPR/Cpf1 gene editing composition may be introduced in the form of a recombinant vector including a DNA encoding a Cpf1 and a recombinant vector including a DNA encoding a crRNA into a cell or organism, or may be introduced in the form of a mixture including a Cpf1 protein and a crRNA or a ribonucleoprotein in which the Cpf1 protein and the crRNA form a complex into a cell or organism.

An exemplary embodiment provides a composition for genome editing including a guide sequence capable of hybridizing with a target nucleotide sequence or a DNA encoding the guide sequence and a Cpf1 protein or a DNA encoding the Cpf1 protein, or a ribonucleoprotein which is a complex of a crRNA and a Cpf1 protein.

Another exemplary embodiment provides a method for genome editing of an organism, the method including: delivering a ribonucleoprotein including a guide RNA (crRNA) and a Cpf1 protein to an organism.

A Cpf1 protein or a DNA encoding the Cpf1 protein and a guide RNA or a DNA encoding the guide RNA, which are included or used in the composition for genome editing or the method for genome editing may be used in the form of a mixture including a Cpf1 protein and a guide RNA or a ribonucleoprotein (RNA) in which the Cpf1 protein and the guide RNA form a complex, or may be used while the DNA encoding the Cpf1 protein and the DNA encoding the guide RNA are each included in separate vectors, or included together in one vector.

The composition and the method may be applied to a eukaryotic organism. The eukaryotic organism may be selected from the group consisting of eukaryotic cells (for example: fungi such as yeast, eukaryotic animal- and/or eukaryotic plant-derived cells (for example, embryonic cells, stem cells, somatic cells, germ cells, and the like), and the like), eukaryotic animals (for example: vertebrates or invertebrates, more specifically, mammals including primates such as humans and monkeys, dogs, pigs, cows, sheep, goats, mice, rats, and the like), and eukaryotic plants (for example: algae such as green algae, monocotyledonous or dicotyledonous plants such as corn, soybean, wheat, and rice, and the like).

Still another exemplary embodiment provides a method for constructing a genetically modified organism by genome editing using a Cpf1 protein. More specifically, the method for constructing a genetically modified organism may include: delivering a Cpf1 protein or DNA encoding the Cpf1 protein and a guide RNA (CRISPR RNA; crRNA) or DNA encoding the guide RNA to eukaryotic cells. When the genetically modified organism is a genetically modified eukaryotic animal or genetically modified eukaryotic plant, the preparation method may further include culturing and/or differentiating the eukaryotic cells simultaneously with or after the delivering.

Yet another exemplary embodiment provides a genetically modified organism constructed by the method for constructing a genetically modified organism.

The genetically modified organism may be selected from the group consisting of all eukaryotic cells (for example: fungi such as yeast, eukaryotic animal- and/or eukaryotic plant-derived cells (for example, embryonic cells, stem cells, somatic cells, germ cells, and the like), and the like), eukaryotic animals (for example: vertebrates or invertebrates, more specifically, mammals including primates such as humans and monkeys, dogs, pigs, cows, sheep, goats, mice, rats, and the like), and eukaryotic plants (for example: algae such as green algae, monocotyledonous or dicotyledonous plants such as corn, soybean, wheat, and rice, and the like).

In the method for genome editing and the method for constructing a genetically modified organism provided in the present specification, the eukaryotic animals may be those except for humans, and the eukaryotic cells may include cells isolated from eukaryotic animals including humans.

As used herein, the term "ribonucleoprotein" refers to a protein-ribonucleic acid complex including a Cpf1 protein which is an RNA-guided endonuclease and a guide RNA (crRNA).

The Cpf1 protein is an endonuclease of a new CRISPR system distinguished from the CRISPR/Cas9 system , is relatively small in size compared to Cas9, does not require tracrRNA, and can act by a single guide crRNA. In addition, the Cpf1 protein is a protospacer-adjacent motif (PAM) sequence, recognizes a DNA sequence rich in thymine such as 5'-TTN-3' or 5'-TTTN-3' (N is any nucleotide, and a nucleotide having a base of A, T, G, or C) located at the 5'-end, and cuts the double strand of the DNA to produce a cohesive end (cohesive double-strand break). The resulting cohesive end may facilitate NHEJ-mediated transgene knock-in at the target position (or the cleavage position).

The Cpf1 protein of the present invention may be derived from *Candidatus* genus, *Lachnospira* genus, *Butyrivibrio* genus, *Peregrinibacteria, Acidominococcus* genus, *Porphyromonas* genus, *Prevotella* genus, *Francisella* genus, *Candidatus methanoplasma*, or *Eubacterium* genus, and may be derived from a microorganism such as, for example, *Parcubacteria bacterium* (GWC2011_GWC2_44_17), *Lachnospiraceae bacterium* (MC2017), *Butyrivibrio proteoclasiicus, Peregrinibacteria bacterium* (GW2011_GWA_33_10), *Acidaminococcus* sp. (BV3L6), *Porphyromonas macacae, Lachnospiraceae bacterium* (ND2006), *Porphyromonas crevioricanis, Prevotella disiens, Moraxella bovoculi* (237), *Smiihella* sp. (SC_K08D17), *Leptospira inadai, Lachnospiraceae bacterium* (MA2020), *Francisella novicida* (U112), *Candidatus methanoplasma termitum, Candidatus paceibacter*, and *Eubacterium eligens*, but is not limited thereto. In an example, the Cpf1 protein may be derived from *Parcubacteria bacterium* (GWC2011_GWC2_44_17), *Peregrinibacteria bacterium* (GW2011_GWA_33_10), *Acidaminococcus* sp. (BV3L6), *Porphyromonas macacae, Lachnospiraceae bacterium* (ND2006), *Porphyromonas crevioricanis, Prevotella disiens, Moraxella bovoculi* (237), *Leptospira inadai, Lachnospiraceae bacterium* (MA2020), *Francisella novicida* (U112), *Candidatus methanoplasma termitum*, or *Eubacterium eligens*, but is not limited thereto.

The Cpf1 protein may be isolated from microorganisms or non-naturally occurring by recombinant or synthetic methods. The Cpf1 protein may further include, but is not limited to, elements typically used for intranuclear delivery in eukaryotic cells (for example: nuclear localization signal (NLS), and the like). The Cpf1 protein may be used in the form of a purified protein, or may be used in the form of a DNA encoding the Cpf1 protein, or a recombinant vector including the DNA.

The crRNA used in the Cpf1 system of the present invention is characterized in that a uridine repeat sequence is linked to the 3'-end of a guide RNA sequence which is hybridized with a target gene.

In an exemplary embodiment of the present invention, the uridine repeat sequence may be a nucleotide sequence in which uridine is repeated 2 to 20 times. Preferably, the crRNA of the present invention may include 6 to 10 repeated uridine sequences, more preferably 8 uridine repeat sequences.

In another exemplary embodiment of the present invention, the uridine repeat sequence may be a nucleotide sequence represented by $(U_aV)_nU_b$. In this case, a and b are an integer from 2 to 20, n is an integer from 1 to 5, and V is adenine (A), cytosine (C), or guanine (G).

In a preferred exemplary embodiment of the present invention, V is A and may be a nucleotide sequence represented by $(U_aA)_nU_b$.

In a preferred exemplary embodiment of the present invention, n is 1 and may be a nucleotide sequence represented by $U_aVU_b$.

In a preferred exemplary embodiment of the present invention, the uridine repeat sequence may be a nucleotide sequence represented by $U_4AU_6$.

In the present invention, the guide sequence capable of hybridizing with the target nucleotide sequence means a nucleotide sequence having a sequence complementarity of 50% or more, 60% or more, 70% or more, 80% or more, 90% or more, 95% or more, 99% or more, or 100% with a nucleotide sequence (target sequence) of a gene target site (hereinafter, used in the same sense unless otherwise mentioned, and the sequence homology may be confirmed using a typical sequence comparison means (for example, BLAST)). For example, a crRNA capable of hybridizing with the target sequence may have a sequence complementary to a corresponding sequence located on the opposite strand of a nucleic acid strand (that is, a strand in which the PAM sequence is located) in which the target sequence (located on the same sequence as the strand in which the PAM sequence is located) is located, and in other words, the crRNA may include a sequence in which T is substituted with U in the target sequence indicated as the DNA sequence as a targeting sequence site.

In the present specification, the crRNA may be expressed as a target sequence, and in this case, even if not mentioned otherwise, the crRNA sequence may be interpreted as a sequence in which T is substituted with U in the target sequence.

The nucleotide sequence (target sequence) of the gene target site may be a sequence in which TTTN or TTN (N is A, T, C, or G) or a protospacer-adjacent motif (PAM) having a sequence homology of 50% or more, 66% or more, or 75% or more with TTTN or TTN is linked to the 5-end thereof (for example, the PAM sequence is directly linked to the 5'-end of the target sequence (0 nt distance), or is linked to the 5'-end of the target sequence with 1 to 10 nt distance), or may be a sequence in which a sequence (NAAA or NAA, a sequence having a sequence homology of 50% or more, 66% or more, or 75% or more with NAAA or NAA; N is A, T, C, or G; an inverted PAM sequence at the 3'-end) complementary to the PAM sequence in an inverted direction is linked to the 3'-end thereof (for example, the inverted PAM sequence is directly linked to the 3'-end of the target sequence (0 nt distance), or may be linked to the 3'-end of the target sequence with 1 to 10 nt distance) in addition to the 5' end PAM sequence).

In an exemplary embodiment of the present invention, the length of guide sequence included in the crRNA may be 18 to 23 nt, but is not limited thereto.

In an exemplary embodiment of the present invention, the crRNA may be provided in the form of a PCR amplicon including a DNA encoding the crRNA or in the form of being included in a recombinant vector. As an example, the present invention may provide a composition for genome editing including a PCR amplicon including a DNA encoding a crRNA and a recombinant vector including a DNA encoding the Cpf1 protein. As another exemplary embodiment, the present invention may provide a composition for genome editing including a recombinant vector including a DNA encoding a crRNA and a recombinant vector including a DNA encoding the Cpf1 protein. In this case, the recombinant vector may include a crRNA expression cassette including a transcription control sequence such as a crRNA encoding DNA and/or a promoter operatively linked thereto.

The DNA encoding the crRNA and the DNA encoding the Cpf1 protein according to the present invention may be inserted either in one recombinant vector or in separate vectors.

The DNA encoding the crRNA and the DNA encoding the Cpf1 protein according to the present invention may be cloned into either one recombinant vector or separate vectors.

As another example, the delivery of a mixture including a RNA-guided endonuclease (RGEN) and a guide RNA, or a ribonucleoprotein (RNP), a DNA encoding the RGEN, the guide RNA, and the RNP, or a recombinant vector including the DNA to a cell or organism may be carried out by local injection, microinjection, electroporation, lipofection, and the like.

In the above-described method, the delivery of a mixture including the Cpf1 (endonuclease) or a DNA encoding the Cpf1 and a crRNA or a DNA encoding the crRNA or a ribonucleoprotein, or a DNA encoding the ribonucleoprotein may be carried out by delivering a mixture of a Cpf1 and a crRNA expressed (purified) in vitro or a ribonucleoprotein to which the Cpf1 and the crRNA have been conjugated to a eukaryotic cell or a eukaryotic organism by a method such as microinjection, electroporation, and lipofection. In still another example, the delivery of a mixture including the Cpf1 or a DNA encoding the Cpf1 and a crRNA or a DNA encoding the crRNA or a ribonucleoprotein may be carried out by delivering a recombinant vector including an expression cassette including the DNA encoding the Cpf1 and an expression cassette including the DNA encoding the crRNA in separate vectors, respectively or including the same together in one vector to a eukaryotic cell and/or a eukaryotic organism by a method such as local injection, microinjection, electroporation, and lipofection.

The expression cassette may include, in addition to the endonuclease encoding DNA or the crRNA encoding DNA, a typical gene expression control sequence in the form of being operatively linked to the endonuclease encoding DNA or the crRNA encoding DNA.

The term "operatively linked" means a functional bond between a gene expression control sequence and another nucleotide sequence.

The gene expression control sequence may be one or more selected from the group consisting of a replication origin, a promoter, and a transcription termination sequence (terminator).

The promoter described herein is one of the transcription control sequences which regulate the transcription initiation of a specific gene, and is typically a polynucleotide fragment of about 100 to about 2500 bp in length. In an exemplary embodiment, the promoter can be used without limitation as long as the promoter can regulate transcription initiation in a cell, for example, a eukaryotic cell. For example, the promoter may be one or more selected from the group consisting of a cytomegalovirus (CMV) promoter (for example, a human or mouse CMV immediate-early promoter), a U6 promoter, an EF1-alpha (elongation factor 1-a) promoter, an EF1-alpha short (EFS) promoter, an SV40 promoter, an adenovirus promoter (major late promoter), a $pL^{\lambda}$ promoter, a trp promoter, a lac promoter, a tac promoter, a T7 promoter, a vaccinia virus 7.5K promoter, an HSV tk promoter, an SV40E1 promoter, a respiratory syncytial virus (RSV) promoter, a metallothionin promoter, a β-actin promoter, a ubiquitin C promoter, a human interleukin-2 (IL-2) gene promoter, a human lymphotoxin gene promoter, a human granulocyte-macrophage colony stimulating factor (GM-CSF) gene promoter, and the like, but is not limited thereto.

The transcription termination sequence may be a polyadenylation sequence (pA), or the like. The replication origin may be an f1 replication origin, an SV40 replication origin, a μMB1 replication origin, an adeno replication origin, an AAV replication origin, a BBV replication origin, and the like.

The vectors described herein may be selected from the group consisting of plasmid vectors, cosmid vectors, and viral vectors such as bacteriophage vectors, adenovirus vectors, retroviral vectors, and adeno-associated viral vectors. The vector which may be used as the recombinant vector may be constructed by employing a plasmid (for example, pcDNA series, pSC101, pGV1106, pACYC177, ColE1, pKT230, μME290, pBR322, pUC8/9, pUC6, pBD9, pHC79, pIJ61, pLAFR1, pHV14, pGEX series, pET series, pUC19, and the like), a phage (for example, λgt4λB, λ-Charon, λΔz1, M13, and the like), a viral vector (for example, an adeno-associated vural (AAV) vector, and the like), or the used in the art like as a basis, but is not limited thereto.

MODE FOR INVENTION

Hereinafter, the present invention will be described in more detail through Examples. These Examples are only for exemplifying the present invention, and it will be apparent to those of ordinary skill in the art that the scope of the present invention is not interpreted to be limited by these Examples.

Experimental Method

1. Cell Culture and Transfection

10% FBS (Corning) and 1 mM penicillin/streptomycin inactivated by heat were added to a high concentration glucose DMEM medium, and HEK-2931 cells (2931/17, ATCC) were cultured under conditions of 37° C. and 5% $CO_2$.

Cell transduction was performed by electroporation or a lipofection method. Specifically, for electroporation, a plasmid vector (Addgene) in which 2 to 5 μg AsCpf1, LbCpf1, or SpCas9 was encoded was transduced, along with a PCR amplicon in which 1 to 3 μg crRNA or sgRNA was encoded, into $5\times10^5$ to $1\times10^6$ HEK-2931 cells using a Neon electroporator (Invitrogen). A chemically synthesized crRNA (Bioneer) was used instead of the PCR amplicon, if necessary.

For the lipofection method, 3 to 15 μL FuGene reagent (Promega) was mixed with a plasmid vector in which 1 to 5 μg AsCpf1, LbCpf1, or SpCas9 was encoded and 3 to 15 μg PCR amplicon for 15 minutes. $5\times10^5$ cells were plated one day before transduction into a 1 ml DMEM, and then cultured for 48 hours by adding the mixture (300 μL) to the medium.

After culture, the cells were harvested, and a genomic DNA was prepared using a PureHelix™ genomic DNA preparation kit (NanoHelix) or Maxwell™ RSC nucleic acid isolation workstation (Promega).

pSpCas9(BB)-2A-GFP (PX458), pY010(pcDNA3.1-hAsCpf1), and pY016 (pcDNA3.1-hLbCpf1) were obtained from Feng Zhang (Addgene plasmid #48138, #69982, #69988, respectively). The information on the target used in the Examples of the present invention is shown in the following [Table 1] and [Table 2].

TABLE 1

| No. | Gene name | Chromosome | Target Sequence | Location | SEQ ID NO |
|---|---|---|---|---|---|
| 1 | DNMT1 | 19 | [**TTTC**]CTGATGGTCCATGTCTGTTACTC | 1013370 | 1 |
| 2 | DNMT1 | 19 | [**TTTG**]CTACACACTGGGCATCGGTGGGGG | 10207808 | 2 |
| 3 | VEGFA | 6 | [**TTTC**]TCCGCTCTGAGCAAGGCCCACAG | 43781959 | 3 |
| 4 | TP53 | 17 | [**TTTC**]GACATAGTGTGGTGGTGCCCTAT | 7674841 | 4 |
| 5 | LGALS3BP | 17 | [**TTTG**]TGACAGACAGTTCCTGGAGTGCA | 78972059 | 5 |
| 6 | INIP | 9 | [**TTTA**]AGAGCAGCGATTGTAAGGAGAGG | 112718012 | 6 |
| 7 | LOC105370393 | 14 | [**TTTA**]AAGAAAGCTACAGGAAAGCAGGG | 19916499 | 7 |
| 8 | KLHL29 | 2 | [**TTTA**]GAGAGACCGCTCAGGCTGGAGGG | 23847019 | 8 |
| 9 | KLHL29 | 2 | [**TTTA**]GGGAGACAGGGAGAAGTGAGAGG | 23847166 | 9 |
| 10 | KIF26B | 1 | [**TTTA**]CCCCTGCATTGCCATGAGCCCCC | 245687161 | 10 |
| 11 | KIF26B | 1 | [**TTCC**]GGGGGCTCATGGCAATGCAGGGG | 245687161 | 11 |
| 12 | CAV1 | 7 | [**TTTA**]CCCGAGTCCTGGGGACAGTCCCC | 116525483 | 12 |
| 13 | CAV1 | 7 | [**TCCC**]GGGGACTGTCCCAGGACTCGGG | 116525483 | 13 |
| 14 | ITGB5 | 3 | [**TTCC**]CCGCAGTGACACTCGCCATGGCC | 124773887 | 14 |
| 15 | ITGB5 | 3 | [**TTTA**]GGCCATGGCGAGTGTCACTGCGG | 124773887 | 15 |
| 16 | COL8A1 | 3 | [**TTTA**]GATTCATTCTCAGTGCCATGGGG | 99413340 | 16 |
| 17 | COL8A1 | 3 | [**TTTA**]AGGCAATTGCAACCACTGAAGGG | 99413482 | 17 |

(*The four sequences in [ ] of the above target sequence meant the PAM sequence)

TABLE 2

| No. | Gene name | Strand | Type | | Primer (5'-3') | SEQ ID NO |
|---|---|---|---|---|---|---|
| 1 | DNMT1 | negative | intron | forward | CTGGGACTCAGGCGGGTCAC | 18 |
| | | | | reverse | CCTCACACAACAGCTTCATGTCAGC | 19 |
| 2 | DNMT1 | negative | intron | forward | AAGCAAATCCACCTGCCTCG | 20 |
| | | | | reverse | CCTCCCCTAGCCCTTTCAGG | 21 |
| 3 | VEGFA | negative | exon | forward | CTAGCCAGTGCTGCCTCTTT | 22 |
| | | | | reverse | CGCTCGCTCACTCTCTTTCT | 23 |
| 4 | TP53 | positive | exon | forward | CAGATAGCGATGGTGAGCAG | 24 |
| | | | | reverse | GGGAGGTCAAATAAGCAGCAGG | 25 |
| 5 | LGALS3BP | positive | exon | forward | ACTGAAGGCCGTGGACACCT | 26 |
| | | | | reverse | CTTGTCCTGGAAGAGGAAGC | 27 |
| 6 | INIP | negative | exon | forward | ACAGGGCCATCTTGTGACAG | 28 |
| | | | | reverse | CCGCTAAAGTGCGAATCACG | 29 |
| 7 | LOC105370393 | positive | intron | forward | GCCAGCCCCTGATTCTTCAG | 30 |
| | | | | reverse | AGTGAATTATGTTGGCTTGGCA | 31 |
| 8 | KLHL29 | negative | intron | forward | AAGCCGAAAGCCTACACCTC | 32 |
| | | | | reverse | GGACATTCGAAGCCCGTGTA | 33 |
| 9 | KLHL29 | negative | intron | forward | AAGCCGAAAGCCTACACCTC | 34 |
| | | | | reverse | GGACATTCGAAGCCCGTGTA | 35 |
| 10 | KIF26B | positive | exon | forward | CTTTCAACAAAGCAGCCCCC | 36 |
| | | | | reverse | TGCTCTGGTCTCAGCATTCG | 37 |
| 11 | KIF26B | negative | exon | forward | CTTTCAACAAAGCAGCCCCC | 38 |
| | | | | reverse | TGCTCTGGTCTCAGCATTCG | 39 |
| 12 | CAV1 | positive | intron | forward | TGAGATTGGGTCTGTTGGGC | 40 |
| | | | | reverse | TGAGATTGGGTCTGTTGGGC | 41 |
| 13 | CAV1 | negative | intron | forward | TGAGATTGGGTCTGTTGGGC | 42 |
| | | | | reverse | TGAGATTGGGTCTGTTGGGC | 43 |
| 14 | ITGB5 | positive | exon | forward | TTGGTAAGAATGCGGCTCCC | 44 |
| | | | | reverse | CATAACCATCTGGTGCCCCA | 45 |
| 15 | ITGB5 | negative | exon | forward | TTGGTAAGAATGCGGCTCCC | 46 |
| | | | | reverse | CATAACCATCTGGTGCCCCA | 47 |
| 16 | COL8A1 | positive | intron | forward | GTGGCCAGGGTGGAGGATAAG | 48 |
| | | | | reverse | CTCTGGCTCCTTTGATACCTCCG | 49 |
| 17 | COL8A1 | positive | intron | forward | GTGGCCAGGGTGGAGGATAAG | 50 |
| | | | | reverse | CTCTGGCTCCTTTGATACCTCCG | 51 |

2. AsCpf1 PAM Variant

Site-directed mutagenesis was performed on a Veriti thermal cycler (Life Technologies) using pY010 plasmid vector as a template and mutagenic primers. S542R mutation was created using a mutagenic primer pair (SEQ ID NOS: 52 and 53). K607R and K548V/N552R mutations were created using additional mutagenic primers (SEQ ID NOS: 54 to 57). The primer sequences used in the present example are shown in the following Table 3.

TABLE 3

| SEQ ID NO | Primer | Sequence (5'-3') |
|---|---|---|
| 52 | S542R mutagenic F primer | 5'-TACACTGGCCAGAGGCTGGGACG-3' |
| 53 | S542R mutagenic R primer | 5'-CGTCCCAGCCTCTGGCCAGTGTA-3' |
| 54 | K607R mutagenic F primer | 5'-GATGATCCCAAGGTGCAGCACCC-3' |
| 55 | K607R mutagenic R primer | 5'-GGGTGCTGCACCTTGGGATCATC-3' |
| 56 | K548V/N552R mutagenic F primer | 5'-GTGGAGAAGAACAGAGGCGCCATCCTGTTT-3' |

TABLE 3-continued

| SEQ ID NO | Primer | Sequence (5'-3') |
|---|---|---|
| 57 | K548V/N552R mutagenic R primer | 5TCTGTTCTTCTCCACATTCACGTCCCAGCC-3' |

Briefly, 100 ng of plasmid template and 15 pmol of each mutagenic primer were added to a 50 μl Toyobo KOD mixture (Takara), and an initial denaturation step (3 minutes, 94° C.), 25 cycles of a denaturation step (20 seconds, 95° C.), an annealing step (40 seconds, 62° C.), and a polymerization step (10 minutes, 72° C.) were performed. The 10 μl PCR product was reacted with 2 μl DpnI (New England Biolabs) at 37° C. for 2 hours. This reaction mixture (5 μl) was heat denatured at 62° C. for 20 minutes, and then used to transform BL21 (DE3) *E. coli* cells. Mutagenesis was confirmed by a Sanger sequencer.

3. Purification of Recombinant AsCpf1

The codon-humanized Cpf1 gene obtained from *Acidaminococcus* sp. was cloned into a pET-28a(+) plasmid vector (Invitrogen), and the vector structure was transformed into BL21(DE3) *E. coli* cells.

genetically modified *E. coli* colonies were grown in an LB medium (LB broth) at 37° C. to an optical density (ca) up to 0.7, and then the cells were cultured at 30° C. overnight in the presence of 0.1 mM isopropylthio-β-D-galactoside (IPTG) in order to induce the production of a recombinant protein. Next, the cells were obtained by centrifugation at 3,500 g for 30 minutes, and were disrupted by ultrasonication. The cell elute was purified by centrifugation at 15,000 g for 30 minutes and filtered using a 0.45 μm syringe filter (Millipore). The purified eluate was loaded onto a $Ni^{2+}$-affinity column using an FPLC purification system (AKTA Purifier, GE Healthcare).

Further, recombinant AsCpf1 was purified in an automated protein production system (ExiProgen, Bioneer) by adding a 1 μg of a genetic construct to an in vitro transcription mixture. The concentration of the produced protein was confirmed by SDS-PAGE stained with Coomassie blue using bovine serum albumin (BSA) as a reference.

4. AsCpf1 In Vitro DNA Cleavage

The TTTC PAM followed by a PCR amplicon having a DNA sequence of 5'-CTGATGGTCCATGTCTGTTACTC-3' (SEQ ID NO: 58) was cloned into a T-Blunt vector (Solgent). The vector construct was amplified in DH5α*E. coli* cells and purified using a HiGene™ DNA purification kit (Biofact). The target vector (20 ng/μL) was reacted with a purified recombinant AsCpf1 protein (50 ng/μL) and chemically synthesized crRNAs (10 ng/μL) at 37° C. for 30 to 60 minutes. The reacted mixture was used to transform DH5α *E. coli* competent cells by dissolving the reacted mixture in a 10% SDS-PAGE gel for quantification of the cleaved product or by adding thermal shock at 42° C. for 2 minutes. The genetically modified cells were applied to LB agar plates containing ampicillin (50 ng/μL) and cultured at 37° C. The number of colonies formed to induce crRNA-dependent DNA cleavage of AsCpf1 was counted.

5. Indel Quantification

A T7 endonuclease I (T7E1) assay was performed to evaluate the Indel efficiency by AsCpf1, LbCpf1, or SpCas9 in the targeted loci of HEK-293T cells. PCR products were obtained by PCR amplification of the target site using a Solg™ Pfu-based PCR amplification kit (SolGent). The PCR product (100 to 300 μg) was then reacted with 10 units of T7E1 enzyme (New England Biolabs) in a 25 p reaction mixture at 37° C. for 1 hour. The 20 μL reaction mixture was loaded directly onto a 10% SDS-PAGE gel and the cleaved PCR product was run in a TBE buffer system. The gel image was stained with an ethidium bromide solution, and then digitized on a Printgraph 2M gel imaging system (Atto). For the calculation of the indel efficiency, the digitized image was analyzed using Image J software.

6. Off-Target Activity Evaluation

Cas-OFFinder [21; Tables 4 to 9] was used to select potential off-target sites with two or less bulges and mismatches. After transduction with the AsCpf1 vector construct and the crRNA-encoding PCR amplicon, HEK-293T cells were cultured in DMEM for 2 days.

TABLE 4

| Target | Reference (Ref) sequence* | Location** | Gene name | SEQ ID NO |
|---|---|---|---|---|
| Ontarget | [TTTC]TTTCCTGTTTGTCTTGTGTC | 63529049 | PTK6 | 59 |
| Offtarget_1 | [TTTG]TTTtCTGTTTGTCTTGTAGTC | 92840367 | GRID2 | 60 |
| Offtarget_2 | [TTTG]TTTCCTGTTTGTCTTGT-aC | 124222832 | CNTNAP5 | 61 |
| Offtarget_3 | [TTTC]TTTCCTGTTT--CTTtTGTC | 19610119 | SLC24A3 | 62 |
| Offtarget_4 | [TTTC]TTTCCTGTTTGTCTTGCATcTC | 79439750 | NRXN3 | 63 |
| Offtarget_5 | [TTTG]TTTCCTGTTTGTtTTGTGTt | 31598764 | SRD5A2 | 64 |
| Offtarget_6 | [TTTA]TTTCtTGTTTGTCTTG-Gta | 72315368 | [Intergene] | 65 |
| Offtarget_7 | [TTTG]TTTtCTGgTTGTCTTGTTGTC | 81529011 | GBE1 | 66 |
| Offtarget_8 | [TTTG]TTT--TGTTTGTCTTGTtTt | 21505926 | [Intergene] | 67 |
| Offtarget_9 | [TTTG]TTTCCTGTTTcTCT--TtTC | 141212565 | TMEM178B | 68 |

(* The four sequences in the [ ] ov the above target sequence mean the PAM sequence. The lower case is the mismatch sequence, the - sign means bulge;
** the location of the target sequence follos Genome Reference Consortium Human Build 38 patch release 11 (GRCh38.p11).)

TABLE 5

| | Target | | | | | |
|---|---|---|---|---|---|---|
| | Ontarget | | | Offtarget_1 | | |
| crRNA used | None | Con-crRNA | U-rich crRNA | None | Con-crRNA | U-rich crRNA |
| # of Totalreads | 32,198 | 60,926 | 72,353 | 26,146 | 42,698 | 36,134 |
| # of Trimmed reads | 30,593 | 57,674 | 71,154 | 25,671 | 41,974 | 35,638 |
| # of reads withRefsequence | 29,639 | 55,050 | 63,763 | 25,009 | 40,983 | 34,747 |
| % of Refsequence | 96.88 | 95.45 | 89.61 | 97.42 | 97.64 | 97.50 |
| # of reads withSNP*** | 954 | 1,540 | 3,898 | 662 | 991 | 891 |
| # of reads withindel | 0 | 1,084 | 3,493 | 0 | 0 | 0 |
| % of indelmutations | 0.00 | 1.88 | 4.91 | 0.00 | 0.00 | 0.00 |
| Sample ID | crRNA_On_N | crRNA_On_C | crRNA_On_U | crRNA_OF_1_N | crRNA_OF_1_C | crRNA_OF_1_U |

TABLE 6

| | Target | | | | | |
|---|---|---|---|---|---|---|
| | Offtarget_2 | | | Offtarget_3 | | |
| crRNA used | None | Con-crRNA | U-rich crRNA | None | Con-crRNA | U-rich crRNA |
| # of Totalreads | 50,910 | 65,262 | 47,616 | 18,932 | 36,988 | 37,582 |
| # of Trimmed reads | 46,579 | 60,213 | 43,916 | 18,373 | 36,500 | 37,031 |
| # of reads withRefsequence | 45,174 | 58,667 | 42,540 | 18,021 | 36,160 | 36,638 |
| % of Refsequence | 96.98 | 97.43 | 96.87 | 98.08 | 99.07 | 98.94 |
| # of reads withSNP*** | 1,405 | 1,546 | 1,376 | 352 | 340 | 393 |
| # of reads withindel | 0 | 0 | 0 | 0 | 0 | 0 |
| % of indelmutations | 0.00 | 0.00 | 0.00 | 0.00 | 0.00 | 0.00 |
| Sample ID | crRNA_OF_2 _N | crRNA_OF_2_C | crRNA_OF_2_U | crRNA_OF_3_N | crRNA_OF_3_C | crRNA_OF_3_U |

TABLE 7

| | Target | | | | | |
|---|---|---|---|---|---|---|
| | Offtarget_4 | | | Offtarget_5 | | |
| crRNA used | None | Con-crRNA | U-rich crRNA | None | Con-crRNA | U-rich crRNA |
| # of Totalreads | 43,440 | 74,232 | 47,392 | 44,078 | 32,546 | 50,086 |
| # of Trimmed reads | 42,908 | 73,219 | 46,684 | 43,476 | 32,189 | 49,461 |
| # of reads withRefsequence | 41,998 | 71,805 | 45,756 | 41,933 | 31,299 | 48,032 |
| % of Refsequence | 97.88 | 98.07 | 98.01 | 96.45 | 97.24 | 97.11 |
| # of reads withSNP*** | 910 | 1,414 | 928 | 1,543 | 890 | 1,429 |
| # of reads withindel | 0 | 0 | 0 | 0 | 0 | 0 |
| % of indelmutations | 0.00 | 0.00 | 0.00 | 0.00 | 0.00 | 0.00 |
| Sample ID | crRNA_OF_4_N | crRNA_OF_4_C | crRNA_OF_4_U | crRNA_OF_5_N | crRNA_OF_5_C | crRNA_OF_5_U |

TABLE 8

| crRNA used | Target Offtarget_6 None | Con-crRNA | U-rich crRNA | Offtarget_7 None | Con-crRNA | U-rich crRNA |
|---|---|---|---|---|---|---|
| # of Totalreads | 38,444 | 22,976 | 53,748 | 37,844 | 32,386 | 72,972 |
| # of Trimmed reads | 37,670 | 22,558 | 52,520 | 37,202 | 31,899 | 71,896 |
| # of reads withRefsequence | 37,188 | 22,206 | 51,728 | 36,723 | 31,482 | 70,963 |
| % of Ref sequence | 98.72 | 98.44 | 98.49 | 98.71 | 98.69 | 98.70 |
| # of reads withSNP*** | 482 | 352 | 792 | 479 | 417 | 933 |
| # of reads withindel | 0 | 0 | 0 | 0 | 0 | 0 |
| % of indelmutations | 0.00 | 0.00 | 0.00 | 0.00 | 0.00 | 0.00 |
| Sample ID | crRNA_OF_6_N | crRNA_OF_6_C | crRNA_OF_6_U | crRNA_OF_7_N | crRNA_OF_7_C | crRNA_OF_7_U |

TABLE 9

| crRNA used | Target Offtarget_8 None | Con-crRNA | U-rich crRNA | Offtarget_9 None | Con-crRNA | U-rich crRNA |
|---|---|---|---|---|---|---|
| # of Totalreads | 48,632 | 34,676 | 61,954 | 51,196 | 33,514 | 48,680 |
| # of Trimmed reads | 47,419 | 33,957 | 60,478 | 50,220 | 32,951 | 47,851 |
| # of reads withRefsequence | 46,440 | 33,308 | 59,435 | 49,682 | 32,571 | 47,308 |
| % of Refsequence | 97.94 | 98.09 | 98.28 | 98.93 | 98.85 | 98.87 |
| # of reads withSNP*** | 979 | 649 | 1,043 | 538 | 380 | 543 |
| # of reads withindel | 0 | 0 | 0 | 0 | 0 | 0 |
| % of indelmutations | 0.00 | 0.00 | 0.00 | 0.00 | 0.00 | 0.00 |
| Sample ID | crRNA_OF_8_N | crRNA_OF_8_C | crRNA_OF_8_U | crRNA_OF_9_N | crRNA_OF_9_C | crRNA_OF_9_U |

(*** The occurrence of SNP was monitored in the investigated alleles by comparing with the sequences of non-treated alleles. These single-nucleotide variations identically observed between Cpf1-treated and non-treated alleles were deemed to be SNP. Those SNPs were taken into account and excluded when calculating off-target frequencies)

The on-target and potential off-target sites were amplified using nested PCR and used for library construction. Each library was purified using Agencourt AMPure XP (Beckman Coulter) and quantified by a Picogreen method using Quanti-iT Picogreen dsDNA Assay Kit (Invitrogen).

After the size of the library was confirmed using the Agilent 2100 Bioanalyzer System (Agilent technologies), qPCR analysis was performed to confirm whether the doses and the appropriate clusters fit well as suggested in Illumina. Next, paired-end sequencing was performed according to the Illumina MiSeq sequence platform using MiSeq Reagent Kit V3 (Life Sciences). Primer sequences were removed from each raw data using the Cutadapt tool (version 1.14). Trimmed sequences were tied and sequence comparisons were performed. The indel mutation observed in the 23-nt target sequence was considered as a genetic correction by off-target activity.

Alternatively, the DNMT1 target site of the HEK-293T cell line was amplified by PCR, and then the indel mutation was induced by transducing 5 μg of an AsCpf1 vector construct and 3 μg of crRNAs, along with an on-target or only one base mismatched sequence, into $2\times10^6$ HEK-293T cells by electroporation. The Indel efficiency was measured by SDS-PAGE gel through T7E1 digestion assay.

7. Unbiased In Vitro Experiment

A crRNA library oligonucleotide having a random 11-nt sequence at the 3'-end was synthesized and each crRNA was made to have the same molar ratio (Integrated DNA Technologies). Oligonucleotide libraries were cloned into pET21 plasmid vectors using sequence- and ligation-independent cloning (SLIC) methods. The cloned plasmid was used to transform BL21 (DE3) *E. coli* cells and secure colony forming units of $10^8$ CFU/mL or more. CFU values were calculated by counting colonies of genetically modified cells serially diluted on ampicillin (+) plates. Genetically modified cells were grown in LB medium supplemented with 50 ng/mL ampicillin until optical density reached 0.6. The water-soluble cells ($2\times10^{10}$ cells/mL) were genetically modified with dCpf1 or Cpf1-carrying pET-28a (+) plasmid vectors (50 to 200 ng) using a Gene Pulser Xcell electroporator (BioRad). The genetically modified cells were plated on agar plates supplemented with ampicillin and kanamycin, to which 0.1 M IPTG was added. The plasmid vector was purified by collecting the colonies formed on each plate.

Using the Illumina HiSeq X Ten Sequencer (Macrogen, South Korea), a deep sequencing analysis was performed on the plasmid vector to calculate the A/T/G/C frequency at each position of the crRNA.

8. Binding Experiment

Binding experiments were performed using isothermal titration calorimetry (ITC) and microscale thermophoresis (MST).

ITC was performed in Auto-iTC200 Microcalorimeter (GE Healthcare). Specifically, titration cells containing 5 μM of the purified recombinant AsCpf1 protein in PBS buffer (pH 7.4) at 25° C. were titrated with chemically synthesized standard or U-rich crRNA (50 μM) at 2 μL/injection. Data analysis was performed using MicroCal Origin™ software (GE Healthcare). The calculated value is the average value of three independent experiments. Monolith NT. 115 (NanoTemper Technologies GmbH) was used to measure the binding affinity of the guide RNA and the effector proteins (SpCas9 and AsCpf1). A chemically synthesized crRNA (IDT Technologies) was labeled with Cy5 fluorescent dye. Purified recombinant AsCpf1 at various concentrations (0.25 nM to 50 μM) was mixed with 8 nM labeled RNA in a PBS buffer containing 0.05% Tween-20 and 0.05% BSA. Analysis was carried out at 24° C. using 5% LED power and 20% MST power.

Meanwhile, in the Cas9 MST experiment, Cy5-labeled crRNA was hybridized with tracrRNA at the same molecular ratio. Specifically, the two RNA oligos resuspended in Nuclease-Free Duplex Buffer (IDT Technologies) were heated at 95° C. for 5 minutes and then cooled at room temperature. The purified SpCas9 protein at various concentrations (0.1 nM to 15 μM) was mixed with 8 nM labeled RNA in a 20 mM HEPES buffer (pH 7.4) containing 150 mM KCl, 0.05% Tween-20, and 0.05% BSA. Analysis was carried out at 24° C. using 20% LED power and 20% MST power. All samples were placed in a NanoTemper standard capillary tube and each measurement was repeated at least 3 times. Binding affinity data were analyzed using NanoTemper analysis software.

9. Northern Blot Analysis

Total RNA was extracted from HEK-293T cells using the Maxwell RSC miRNA Tissue Kit (Promega) according to the manufacturer's instructions. After each sample was denatured in an RNA denaturation buffer (20% formaldehyde, 50% formamide, 50 mM MOPS, pH 7.0) at 65° C. for 15 minutes, 0.3 to 0.5 μg of isolated RNA was separated from 1% agarose/16% formaldehyde gel. The RNA was then transferred from a 10×SSC to a positively charged nylon membrane by capillary migration overnight. The RNA was prehybridized with 20 to 50 ng/ml PCR DIG probe in DIG Easy Hyb rnight preheated to 50° C. for 30 minutes, reacted with PCR DIG Labeling Mix (Roche), and then denatured at 96° C. for 5 minutes. The blot was washed and immunodetected with Anti-Degoxigenin-AP Fab fragment (Roche). The target RNA-DNA probe hybrids were visualized by chemiluminescent assays using a CDP-Star substrate (Roche). The probe sequences (SEQ ID NOS: 69 and 70) are shown in the following Table 10.

TABLE 10

| SEQ ID NO | Probe target | Sequence (5'-3') |
|---|---|---|
| 69 | DNMT1 target3 on-target | 5'-AATTTCTACTCTTGTAGATCTGATGGT CCATGTCTGTTACTC-3' |
| 70 | DNMT1 target3 U-rich | 5'-AATTTCTACTCTTGTAGATCTGATGGT CCATGTCTGTTATTTTATTTTTT-3' |

10. Statistical Analysis

Statistical analysis of the indel efficiency was performed on a Sigma Plot using a two-tailed Student's t-test. Statistical analysis results showed that P-values <0.05 were significant.

EXAMPLE 1

Confirmation of Effect of crRNA Containing U-Repeat Sequence (U-Rich crRNA) on Improvement of dsDNA Cleavage Efficiency of Ascpf1

According to the prior literature (Dong et al. *Nature* 532, 522-538 (2016), Yamano et al. *Cell* 165, 949-962 (2016)) that performed a structural analysis of the crRNA-Cpf1 complex and target DNA in order to confirm how Cpf1 is guided by crRNA and breaks the DNA double helix on targets having the T-repeat sequence of PAMC, it is known that 3-4 nucleotide residues of the crRNA and the target DNA remain unidentified due to their high flexibility. This implies that the critical nucleotide length of the crRNA required to recognize and bind to a specific target is about 20-nt as in the CRISPR/Cas9 system.

The present inventors transfected HEK-293T cells with a plasmid vector along with a PCR amplicon that expressed the codon-humanized AsCpf1 gene and crRNA to confirm whether the 3-4 nucleotides at the 3' end in the crRNA can be simply an unnecessary part or can play other secondary roles besides target recognition. The crRNA was designed to include a 20-nt target sequence for the DNMT1 gene followed by three variable sequences.

Figure 2:
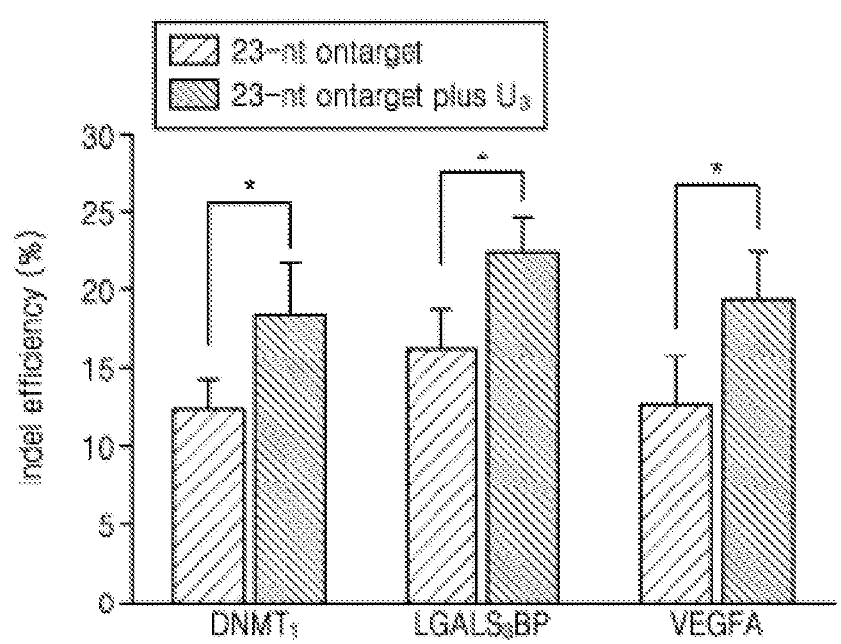
Figure 3:
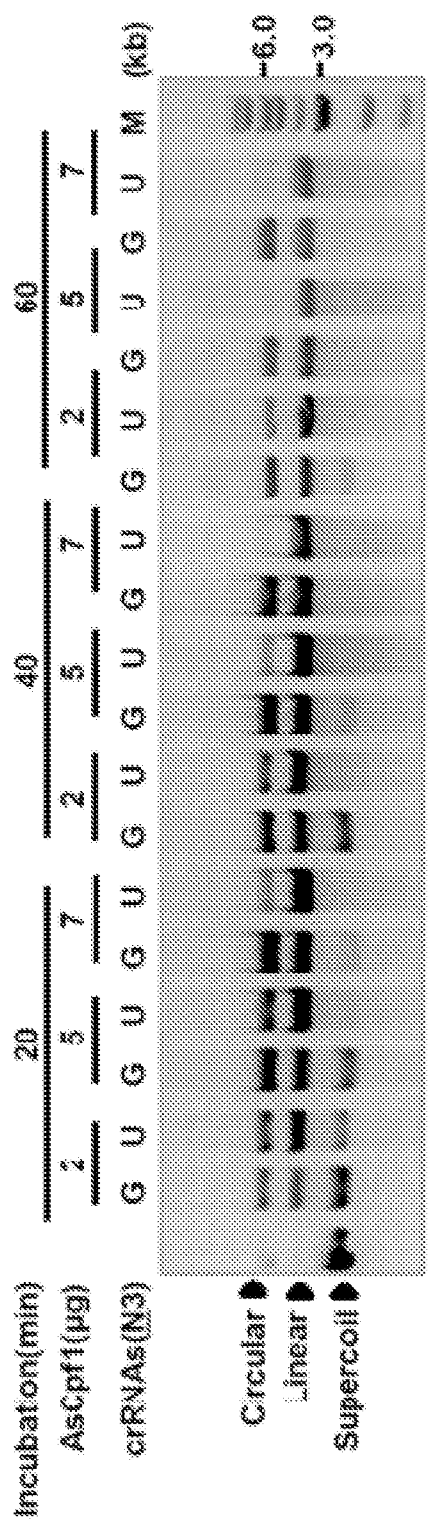

For basic confirmation, four different crRNAs were tested, each including a 3'-overhang of AAA (A3), UUU (U3), GGG (G3), or CCC (C3) as a variable sequence. Results confirmed by a T7E1 digestion analysis showed the highest indel efficiency in the crRNA having the U3 3'-overhang (FIG. 1). In addition, the crRNA having the U3 3'-overhang exhibited improved indel efficiency compared to a crRNA with a 23-nt target-complementary sequence. The same results were exhibited even in experiments on three additional target genes (FIG. 2). In vitro DNA degradation analysis showed that crRNAs having the U3 3'-overhang had remarkably increased dsDNA cleavage compared to the guanidine-rich (G-rich) case (FIG. 3).

Figure 5:
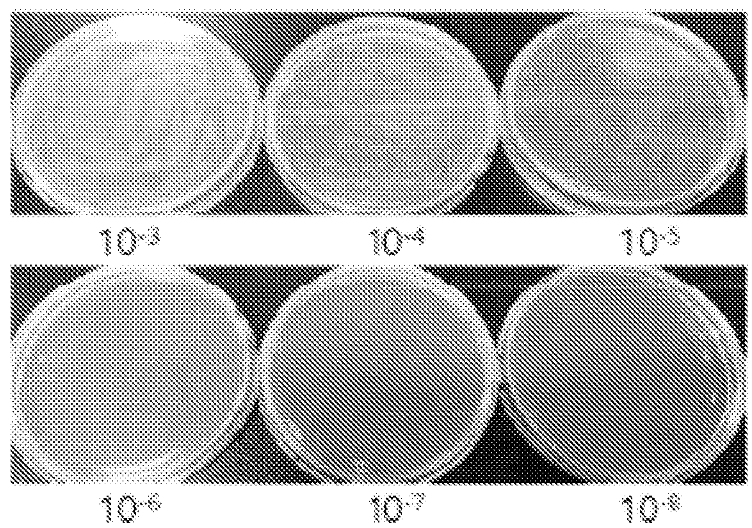
Figure 6:
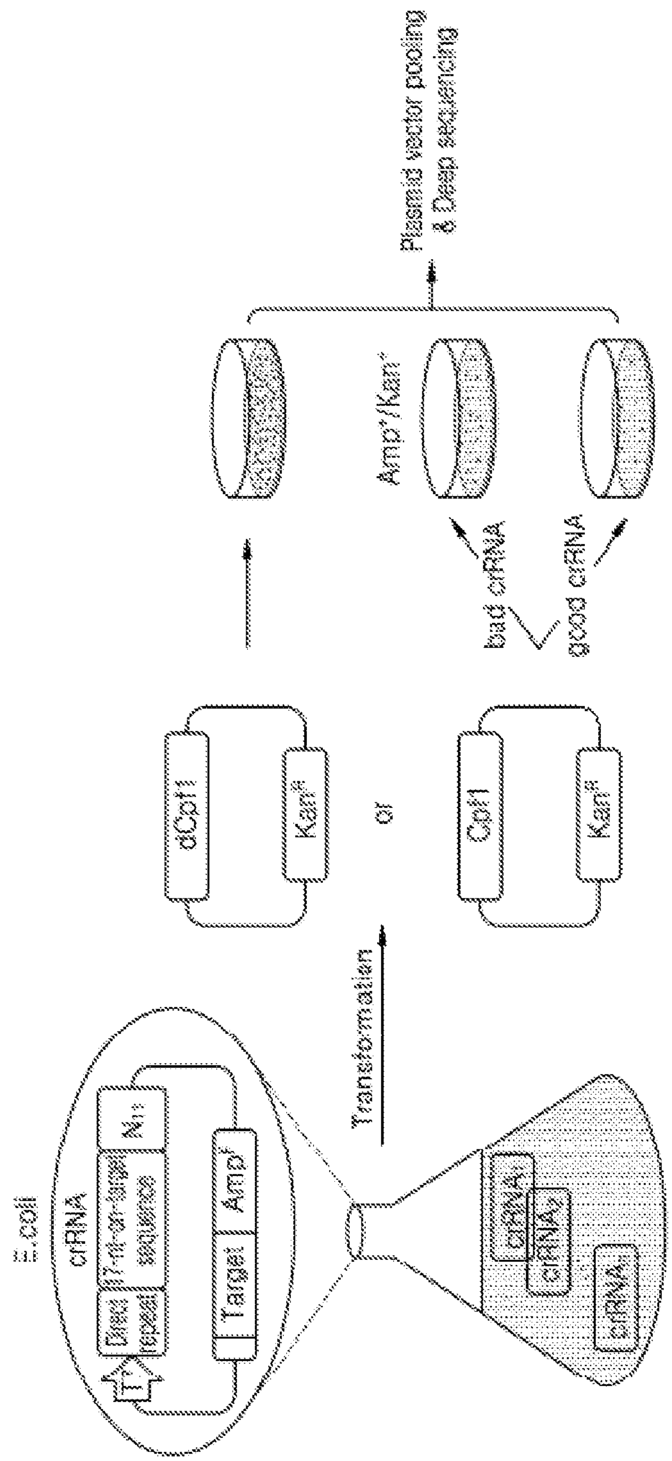
Figure 7:
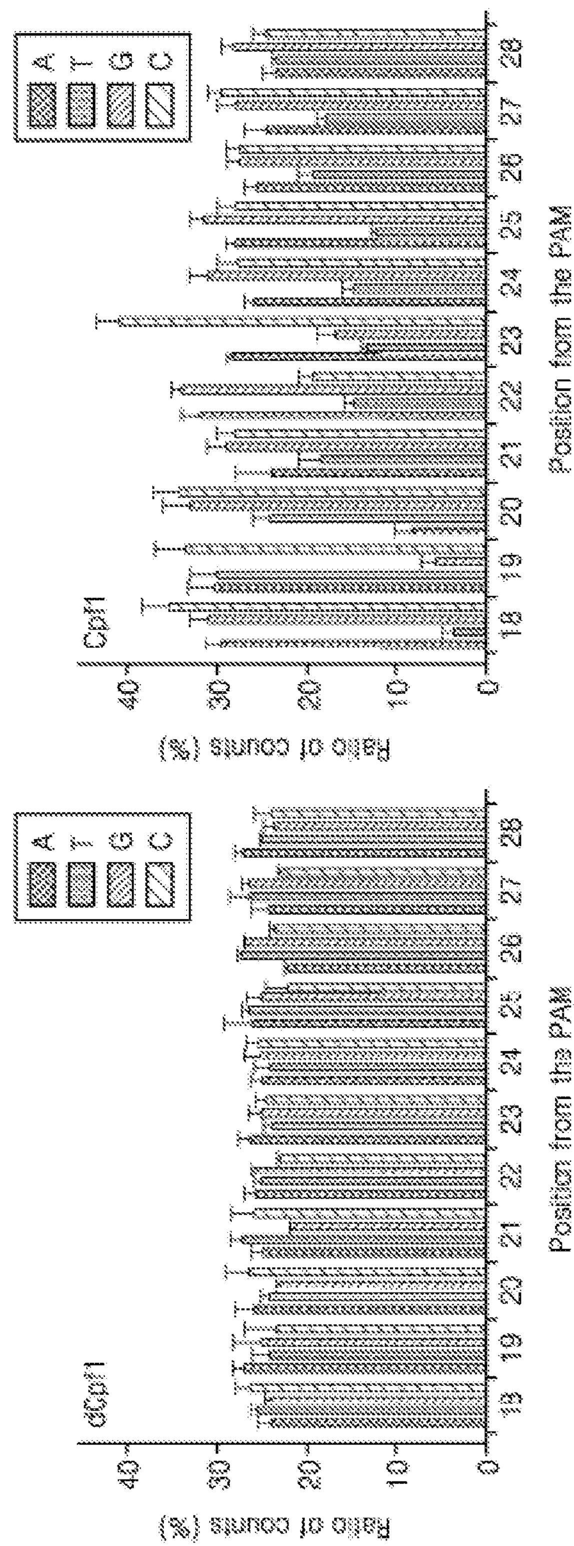
Figure 8:
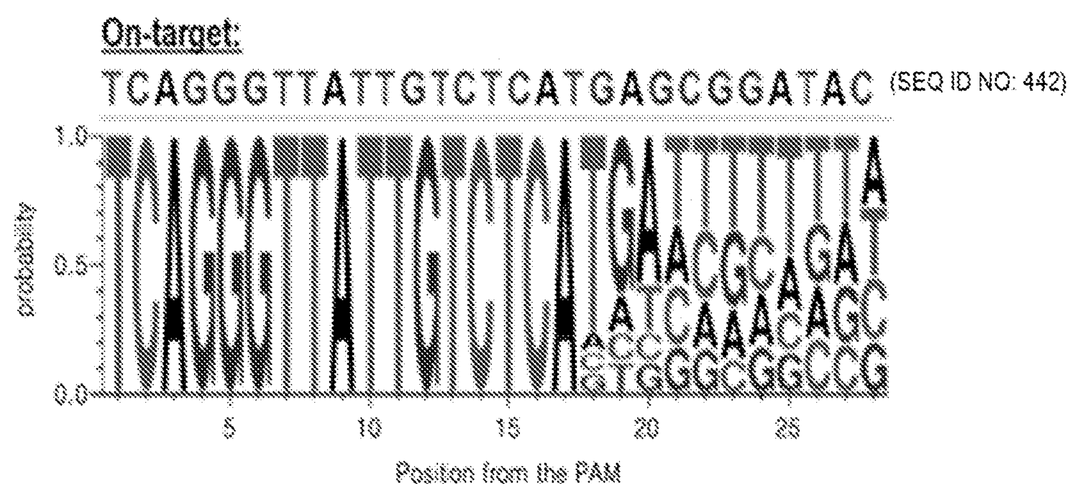

In addition, a plasmid DNA library encoding a crRNA having a 3'-overhang library was prepared. Specifically, a crRNA library oligonucleotide having the 11-nt 3'-end sequence library (411) was synthesized, and each crRNA was allowed to have the same molar ratio. Each crRNA was designed to have 17-nt and 11-nt (N11) random nucleotide sequences for the on-target sequence (FIGS. 4 to 6). Through this design, it was intended to clearly confirm the essential on-target lengths and additional control sequences. Since *E. coli* cells having efficient crRNA are less viable in agar plates supplemented with ampicillin, a negative selection method was applied to track the optimal arrangement of crRNAs. Thereafter, a crRNA-coding plasmid DNA was extracted by collecting viable *E. coli* cells, and the number of nucleotides at each position of the target site was calculated by performing a deep sequencing analysis (FIG. 7). As a result of the analysis of the deep sequencing data, it was confirmed that a crRNA-coding plasmid DNA library was prepared such that A, T, G and C accounted for almost the same molar ratio at each position, as evaluated by dCpf1 treatment. Marginal variation was normalized to the value obtained by dCpf1 treatment. In contrast, it was confirmed that when AsCpf1 was treated, there was a significant difference in the frequency of each nucleotide in a position-dependent manner. A probability value was obtained from the inverted value of the nucleotide ratio at each position exhibiting the optimal crRNA arrangement (FIG. 8). As a result, it was confirmed that the 20-nt on-target sequence was important, but the 21-position was followed by a U-rich 3'-tail independently of the on-target sequence.

Figure 9:
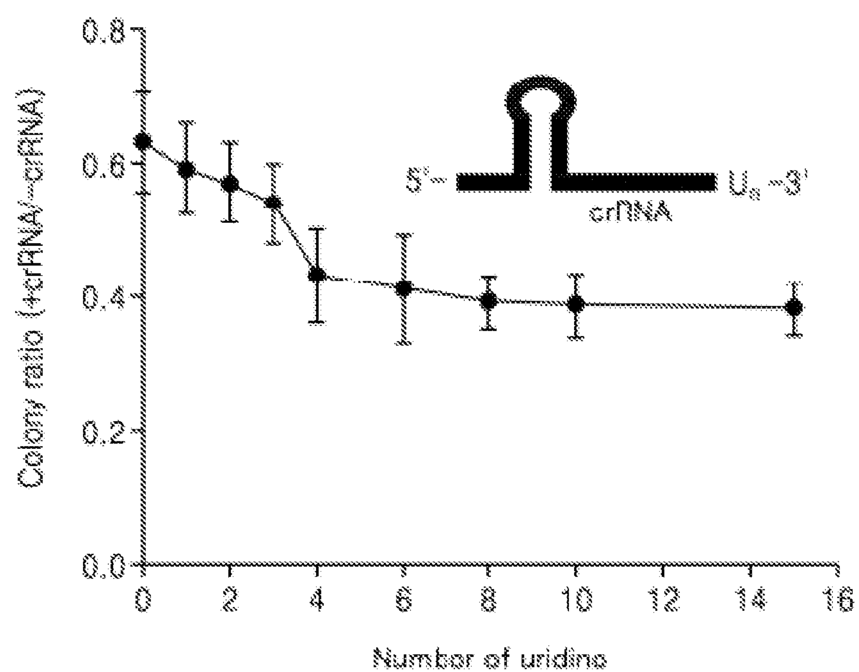

Next, crRNAs having different uridinylate lengths at the 3'-end were chemically synthesized, and the dsDNA cleavage efficiency was tested in vitro of AsCpf1/crRNA ribonucleoproteins. As a result, it could be seen that the DNA cleavage efficiency was the best in the crRNA having the U8 overhang (FIG. 9).

An additional increase in uridinylate length did not have a significant effect on dsDNA cleavage. From this, it could be seen that the addition of 8 uridinylates to the 20-nt target-complementary sequence showed optimal dsDNA cleavage efficiency in vitro.

Figure 10:
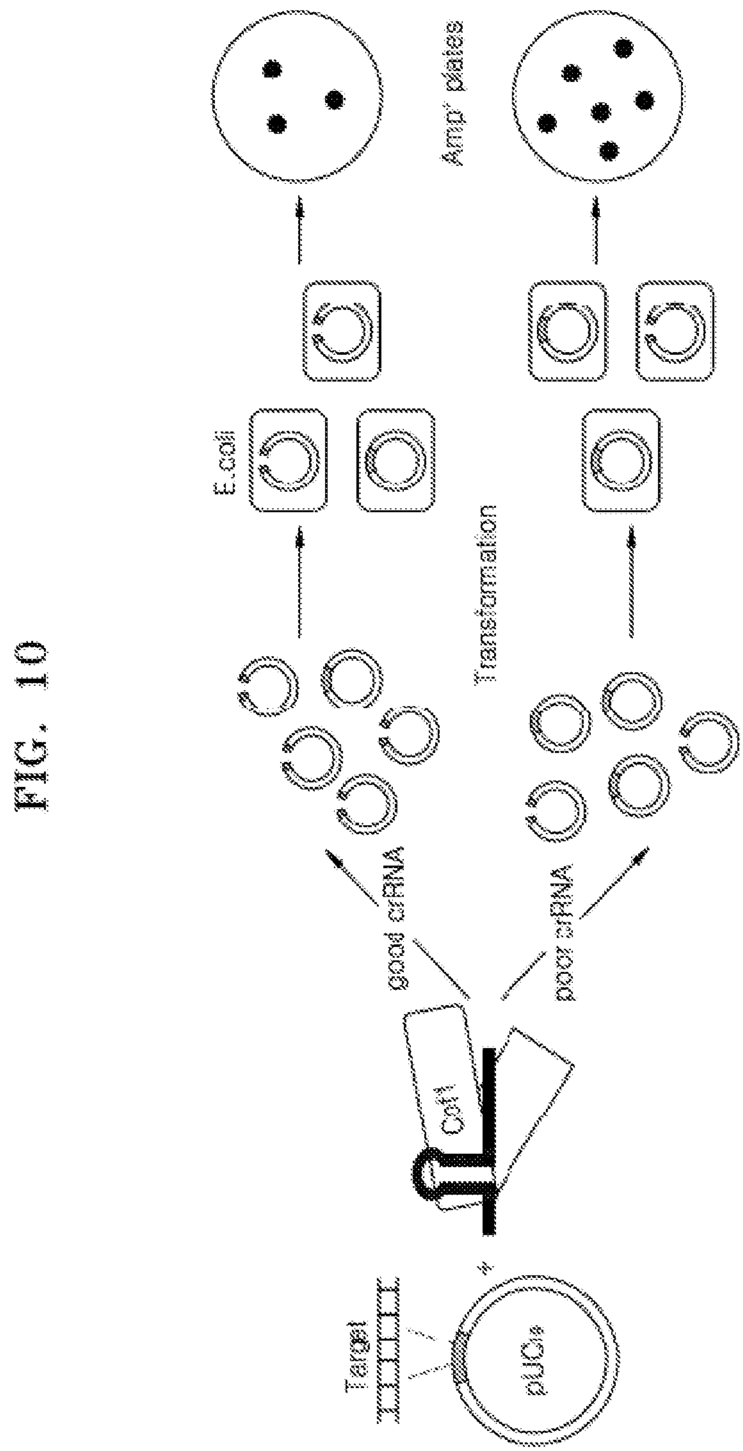
Figure 11:
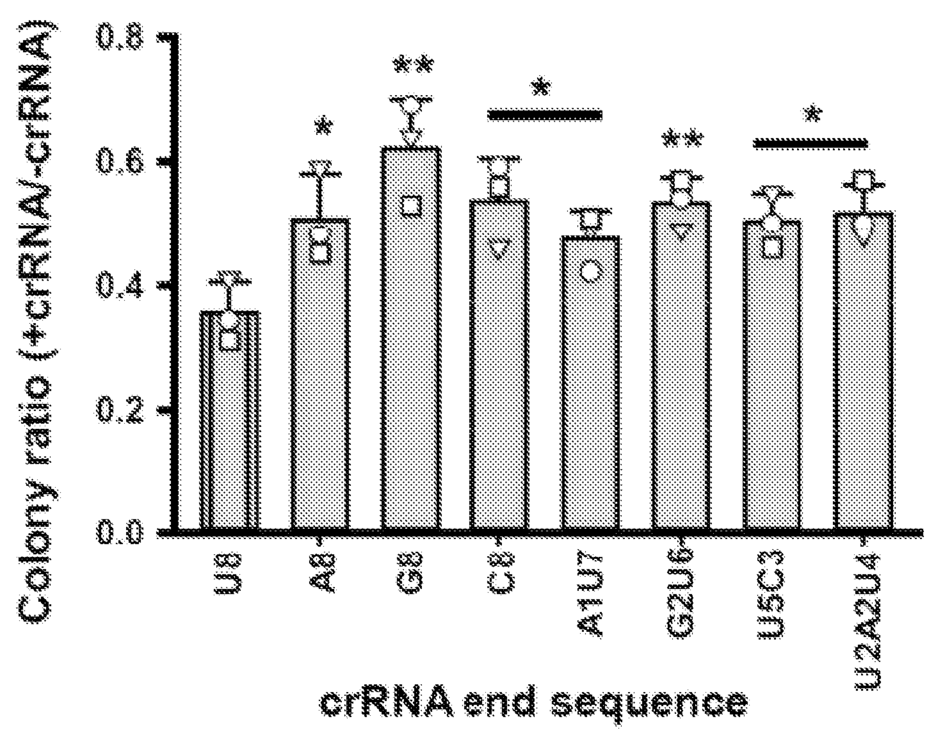

Next, to confirm whether the dsDNA cleavage efficiency of AsCpf1 was increased by the U-rich 3'-overhang of crRNA, an in vitro experiment was designed in which the pUC19 plasmid vector having a 23-nt target sequence for DNMT1 was cultured with the equimolar ratio of AsCpf1/crRNA ribonucleoprotein. Specifically, after partial digestion for 1 hour, *E. coli* DH-5α was transformed using the digested plasmid vector. After *E. coli* cells were plated on LB agar medium containing ampicillin, and the number of colonies formed was counted (FIG. 10). Through repeated experiments, it could be seen that it is important to add eight uridinylates to enhance the efficiency of AsCpf1 activity (FIG. 11). It was confirmed that the dsDNA cleavage activity of AsCpf1 was reduced when uridine is substituted with any other nucleotide at an arbitrary position.

Figure 12:
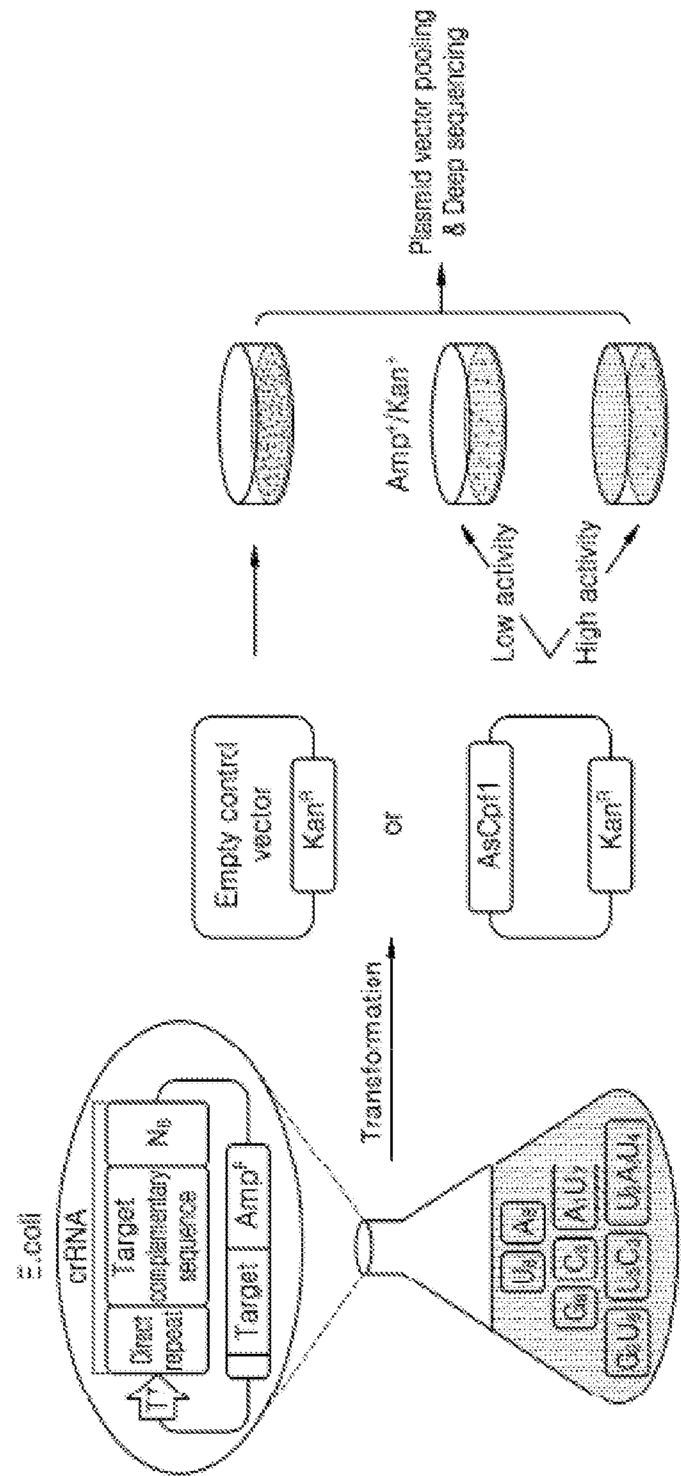
Figure 13:
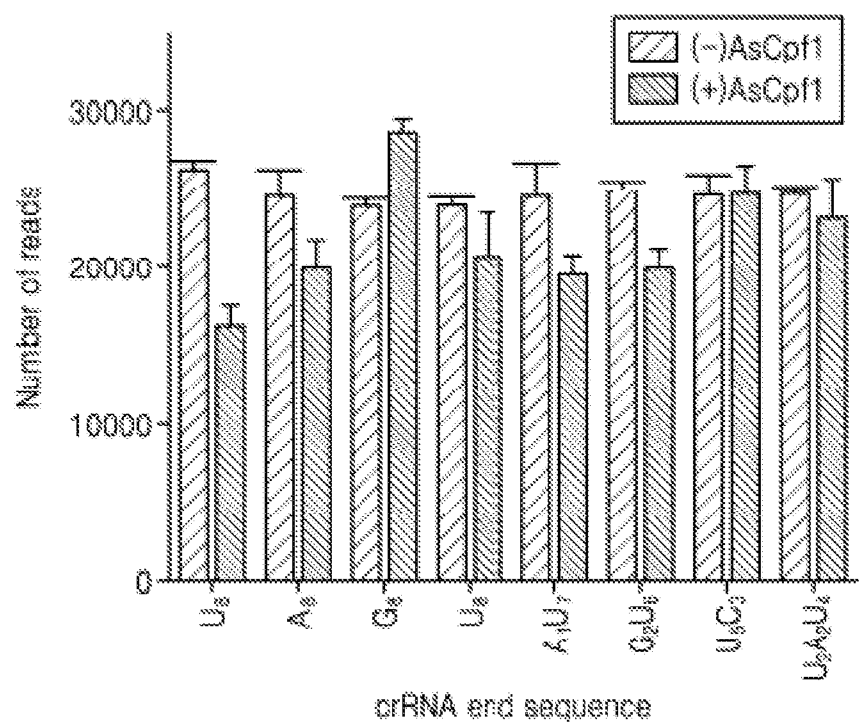
Figure 14:
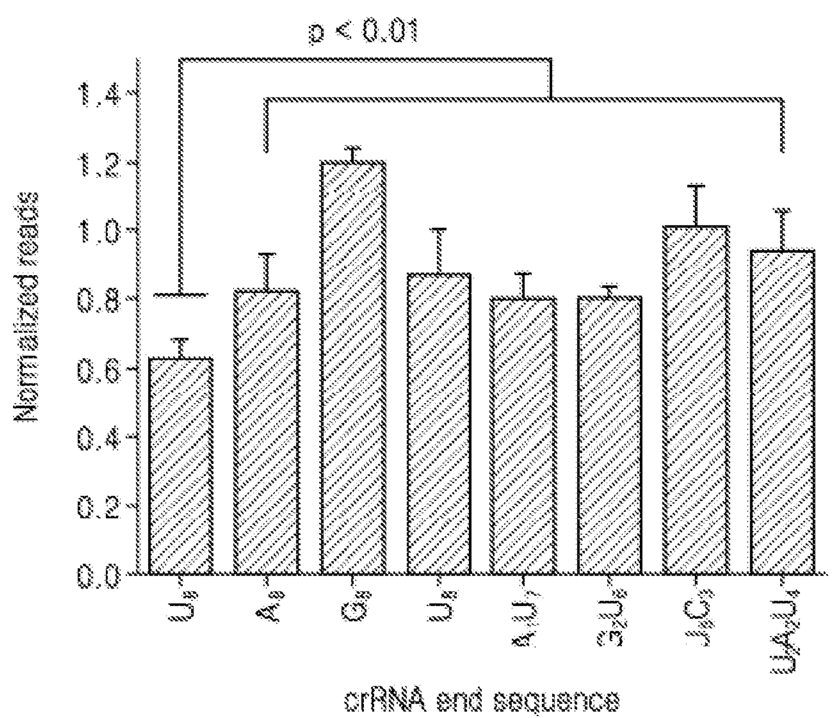

Finally, the effectiveness of the U-rich crRNA was confirmed by performing a robust assay with the strain to confirm the optimal arrangement of the crRNA (FIG. 12). Specifically, BL21 (DE3) *E. coli* cells were transformed with a pET21 vector carrying crRNAs having various 8-nt 3'-tails. The crRNA was designed to target the 5'-close region of the ampicillin resistance gene in the plasmid. Colonies with unique crRNA sequences were screened into electro competent cells. Each competent cell was collected into the same number to prepare crRNA library cells. Thereafter, the competent cells were transformed with the pET-28a (+) plasmid vector with or without AsCpf1 gene. The transformed cells were plated on agar plates supplemented with ampicillin, kanamycin, and 0.1 mM IPTG. The plasmid vectors were purified by collecting colonies formed on each plate, and the occupancy of each crRNA was measured by deep sequencing analysis. As a result, it was confirmed that the number of read was inversely proportional to the efficiency of the crRNA (FIG. 13). Each read obtained in the absence of AsCpf1 was used to standardize the modification of multiple crRNA templates in competent cells. In addition, through standardization of reads, it was confirmed that the crRNA having the U8 3'-overhang showed optimal AsCpf1 activity (FIG. 14) ($p<0.01$, $n=3$ compared to non-U8 overhang).

From the above results, it was confirmed that the 3'-end U-rich-tail of the crRNA is a critical structural determinant for highly efficient dsDNA cleavage by AsCpf1.

EXAMPLE 2

Confirmation of Effect of crRNA Having $U_4AU_4$ 3-Overhang Sequence on Enhancement of Gene Editing Efficiency of Cpf1 (In Vivo)

Figure 15:
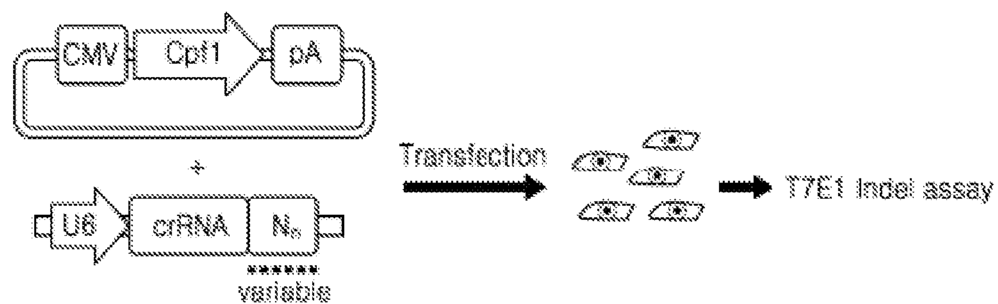
FIGS. 15 to 21 illustrate the results of confirming the optimal crRNA structure for enhancing the genome efficiency in vivo.

In order to confirm whether the U-repeat sequence structure of the crRNA is directly related to the enhancement of the genome editing efficiency in vivo, the indel efficiency was evaluated in HEK-293T cells transfected with a vector construct having a codon-humanized AsCpf1 gene along with a U6 promoter and a crRNA-encoding PCR amplicon including a 20-nt target complementary sequence and a 3'-end mutant sequence (FIG. 15).

Figure 16:
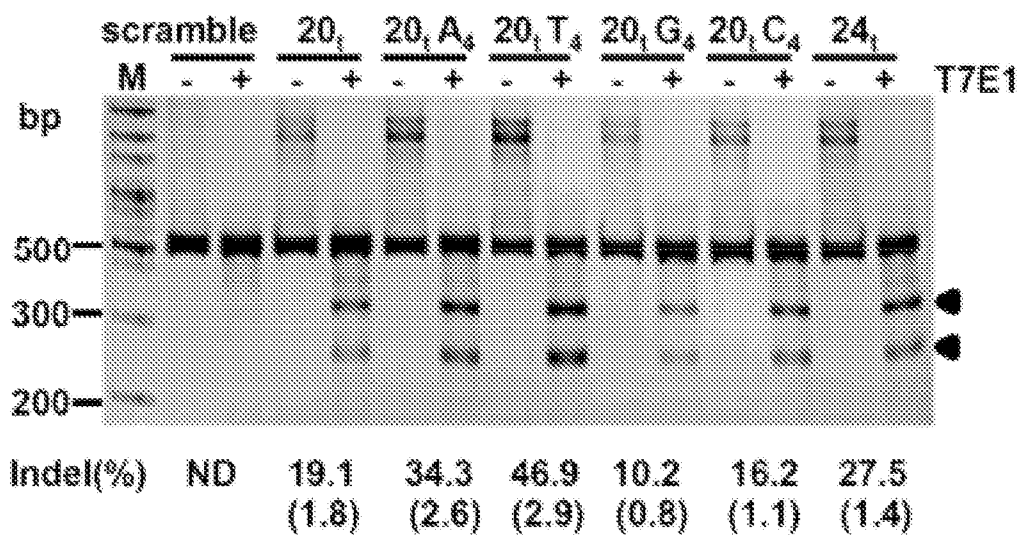

Along with a crRNA-encoding PCR amplicon with a 4-nt 3'-end mutant sequence ($A_4$, $G_4$, $T_4$, $C_4$ or four nucleotides complementary to the target) added to the 20-nt target complementary sequence, the DNMT1 gene was targeted. As a result, it could be confirmed that in the same manner as in the in vitro results (FIG. 1), the indel efficiency was significantly increased compared to other crRNAs ($20_tA_4$, $20_tG_4$, $20_tC_4$, and $24_t$) even when the U-rich crRNA ($20_tT_4$) was used at the 3'-end in vivo (FIG. 16).

From this, it was thought that the repeated uridine residue imparted stability to the crRNA in the cell and the indel efficiency of AsCpf1 was increased due to the stability of the crRNA.

Figure 17:
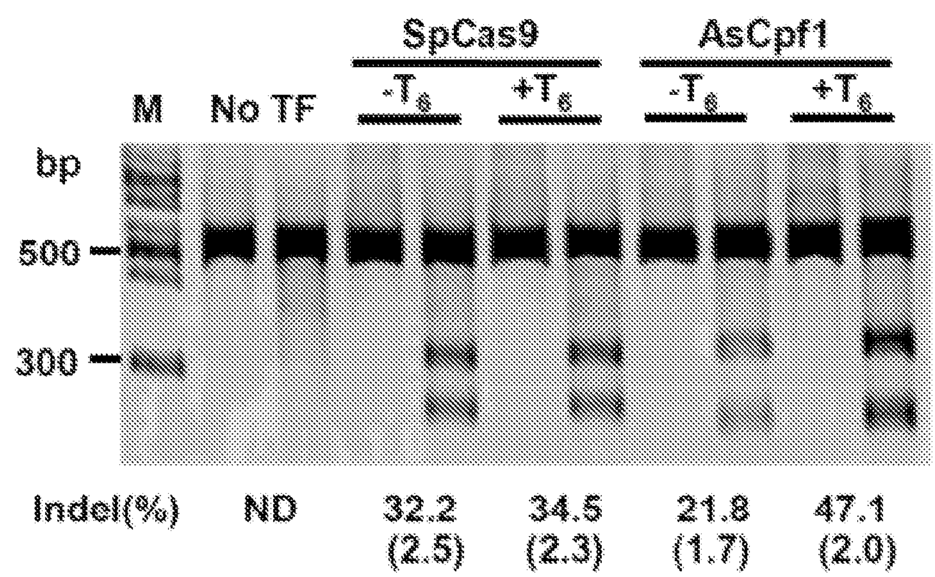

However, the $T_6$ sequence at the 3'-end of the PCR amplicon encoding the single-guide RNA (sgRNA) did not affect the indel efficiency of the CRISPR/Cas9 system, unlike in AsCpf1 (FIG. 17). Further, since the U-rich 3'-overhang was confirmed to be effective in an in vitro system, it could be seen that the U-rich crRNA regulates the activity of Cpf1 when the U-rich drRNA binds to Cpf1.

Figure 18:
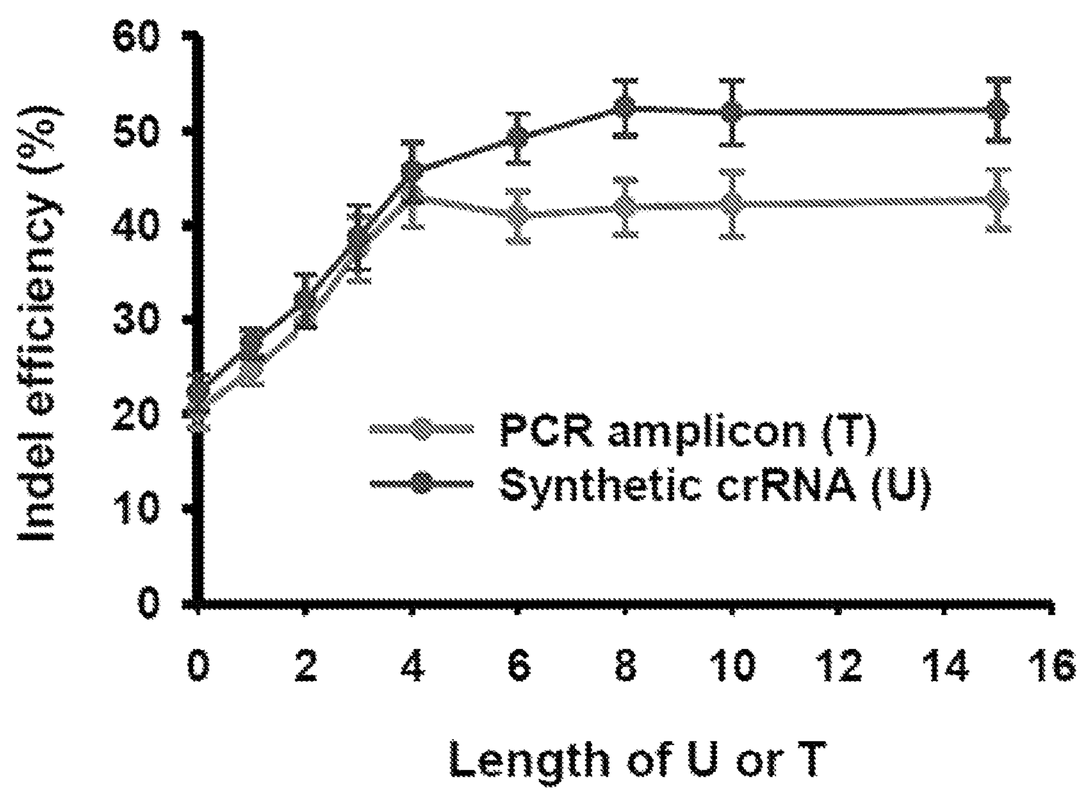

Next, in the crRNA, the change in indel efficiency of AsCpf1 due to the length of the 3'-end uridine was confirmed. It was confirmed in the in vitro experiment that the Cpf1 activity increased in proportion to the length until the length of the uridine was increased to 8-mer in Example 1 (FIG. 3). However, contrary to the in vitro experimental results, it was confirmed that the indel efficiency was almost saturated when the length of T was four in the crRNA-encoding PCR amplicon, and the indel efficiency was not affected even when the length was increased even more (FIG. 18).

This result can be explained by the fact that RNA polymerase III regulates the U6-promoted gene transcription. In this process, successive T-repeat sequences ($T_5$ or $T_6$) of the template DNA act as termination signals, resulting in production of four uridines (U4) at the 3'-end. Accordingly, an increase in the length of the thymidine base sequence in the template is not accompanied by an increase in the length of uridine in the crRNA. However, when a chemically synthesized crRNA was used, it was confirmed that the Cpf1 activity was enhanced in proportion to the length as observed in the in vitro experiment when the length of uridine was increased up to 8-mer (FIG. 18).

Figure 19:
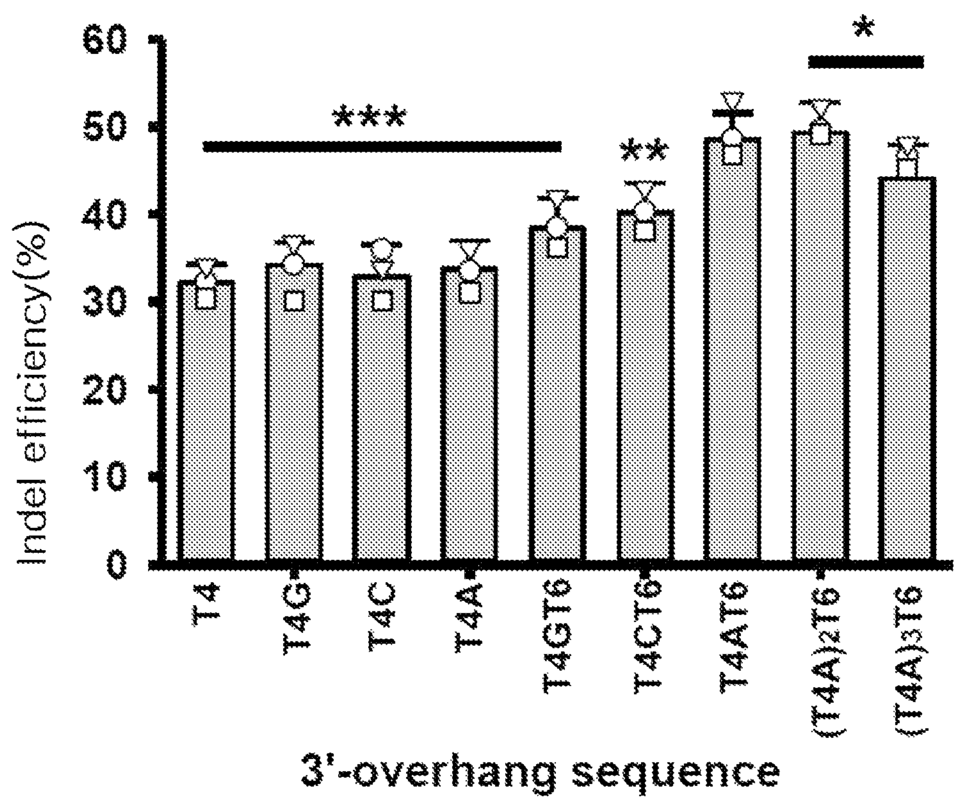

Considering that the repeated uridine at the 3' end is crucial to the increase in indel efficiency in the crRNA, a crRNA-encoding template DNA was designed such that four deoxythymidinylates ($T_4$) were linked to one non-T base and $T_6$, thereby allowing U4VU to produce a crRNA including the 3'-tail sequence (here, V is A, C, or G). The $U_4$ tail is actually made in the transcript of the T-repeat end sequence ($T_5$ or $T_6$) of the template. The indel efficiency was increased when A was bound to the T repeat sequence compared to when G or C was bound to the T repeat sequence (FIG. 19). On the other hand, increasing the number of U by adding $U_4$ A units did not further increase the indel efficiency. From this, it could be seen that synthetic crRNA with at least 8 uridines ($U_8$) added on the target-complementary sequence is important for improving the efficiency of genome editing. When crRNAs are transcribed and made from a DNA template, the template sequence must have a sequence 'TTTTATTTTTT' after the sequence matching the target. This structure produces $U_4AU_4$ 3'-overhangs in the crRNA, which may exhibit indel efficiencies almost similar to that of the synthetic $U_8$-crRNA.

Figure 20:
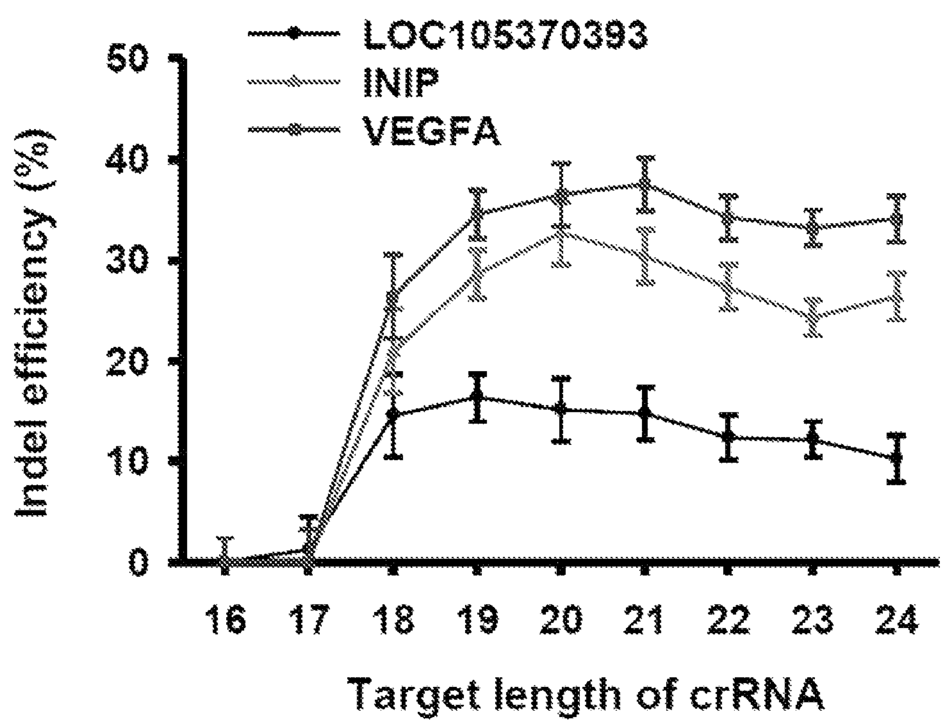

In this case, as a result of examining the indel efficiency according to the length of the target, it could be seen that the most effective target length is 20 (±1) nt, which varies depending on the target (FIG. 20).

Figure 21:
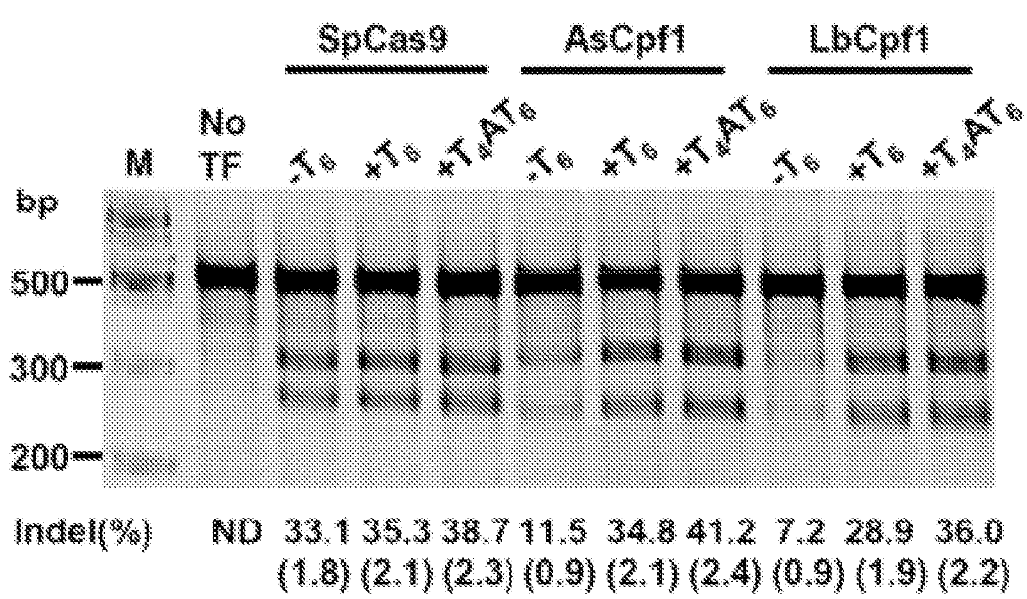

This optimized crRNA structure was applied identically to Cpf1 (LbCpf1) derived from *Lachnospiraceae bacterium*, which is known as an effector protein applicable to eukaryotic cells together with AsCpf1 (FIG. 21).

Figure 22:
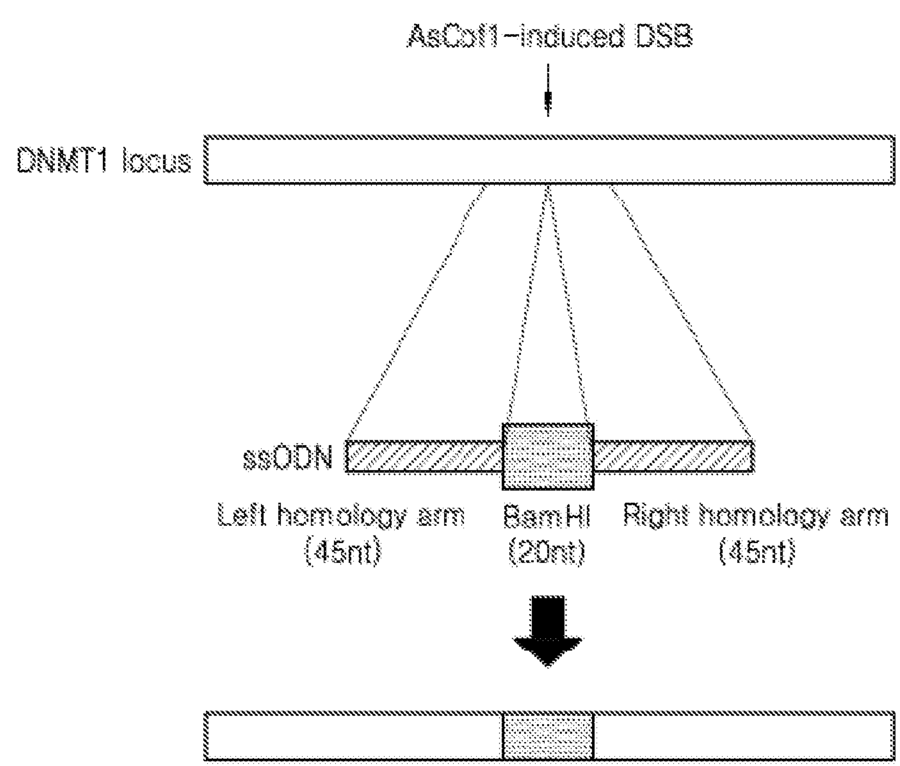
FIGS. 22 to 24 illustrate the results of confirming that the knock-in efficiency is improved by the crRNA including the U-rich 3'-overhang.
Figure 23:
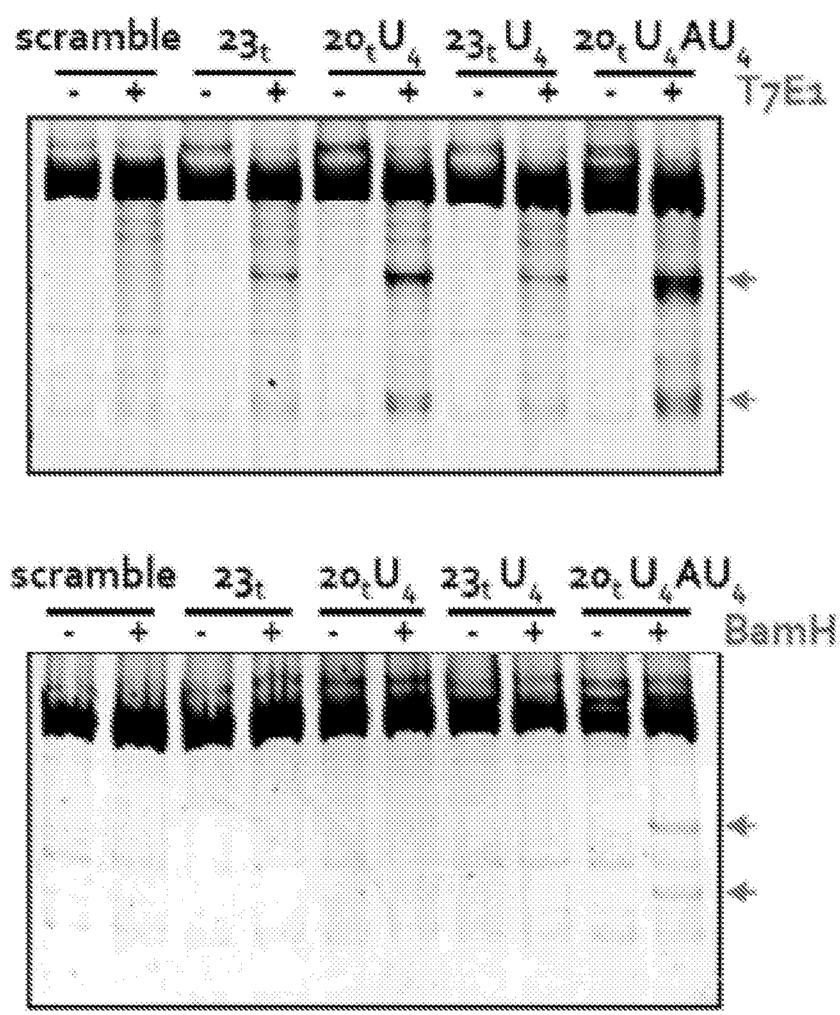
Figure 24:
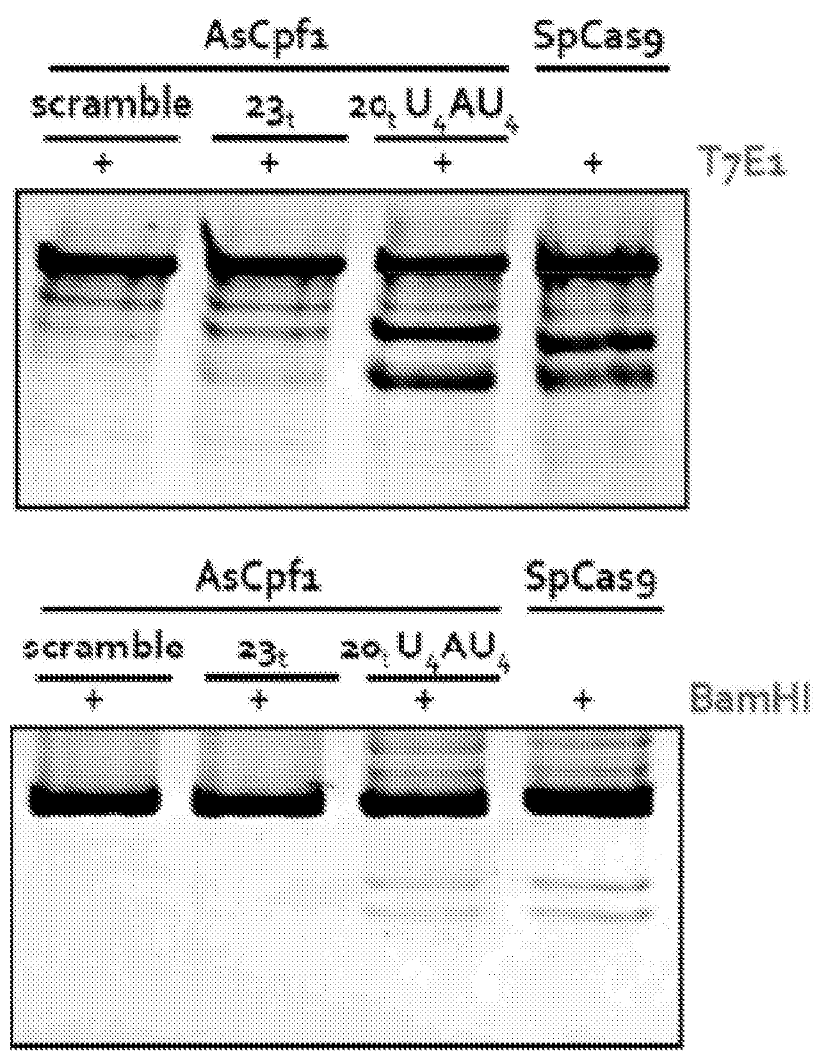

The importance of Cpf1 activity improved by U-rich crRNA could be clearly confirmed in the 'knock-in' experiment. The overall knock-in efficiency of the CRISPR/Cpf1 system is lower than that of CRISPR/Cas9, which also applies even when a single-stranded oligonucleotide (ssODN) is used as a donor. Only U-rich crRNA was able to detect ssODN-based knock-in levels by AsCpf1 (FIGS. 22 to 24).

EXAMPLE 3

Large-Scale Verification of Genome Editing Efficiency of AsCpf1 by U-Rich crRNA Including U-Repeat Sequence In order to confirm whether the indel efficiency improved by the U-rich crRNA is sequence-dependent and the U-rich crRNA can be applied to a wide range of targets, the indel efficiency of AsCpf1 was investigated on a large scale and compared with the results obtained from SpCas9.

First, target genes common to Cpf1 and Cas9 were searched to exclude differences due to target-dependent indel efficiency. Specific targets were searched for against the 5'-TTTV $(N)_{20}$ NGG-3' sequence including the PAM sequence for AsCpf1 and SpCas9 and sharing the 20-nt target sequence. As a result, 115 PCR-validated targets were found in HEK-293T cells including 49 exons, 32 introns, and 34 genes (intergenes) (target information is shown in the following Tables 11 and 12). Single-guide RNAs (sgRNAs) and crRNAs were designed to be transcribed from PCR amplicons including the U6 promoter and sgRNA or crRNA sequences having respective target sequences.

TABLE 11

| Target No. | Chromosome | Location | Gene name | Target sequence (23nt) | SEQ ID NO |
|---|---|---|---|---|---|
| 1 | 22 | 16994935 | GAB4 | CCTGGTGGCTGAGACCAGGGAGG | 71 |
| 2 | 21 | 25603838 | MRPL39 | ATTTCACAGGACTTTGTTAAAGG | 72 |
| 3 | 14 | 28794781 | LINC01551 | ATTTTGAAGTGACCGTACGAGGG | 73 |
| 4 | 14 | 28794751 | LINC01551 | ATAATACACTCTTTACACTGAGG | 74 |
| 5 | 15 | 24987466 | PWAR5 | AACAAATCACTGACTAACCAAGG | 75 |
| 6 | 15 | 24987493 | PWAR5 | GTGTGGATAAGAATCACCTGAGG | 76 |
| 7 | 3 | 131069719 | NUDT16 | GGGGTAGAGGTACTCTACAGGGG | 77 |
| 8 | 3 | 131069756 | NUDT16 | GGGGTAGAGGTAGTCTACAGGGG | 78 |
| 9 | 11 | 3087968 | OSBPL5 | GCATTAAGGCCAGCGCTGGGCGG | 79 |
| 10 | 17 | 3669779 | P2RX5-TAX1BP3 | CACATAGGCCATTCAGAAACGGG | 80 |
| 11 | 17 | 3670244 | P2RX5-TAX1BP3 | ATTTTAGCAATAACCTTACAGGG | 81 |
| 12 | 20 | 499271 | CSNK2A1 | CGTGTTCAAAAACCAAGGCGGGG | 82 |
| 13 | 14 | 20117733 | OR4K17 | ACAAGTTCAGAATCACCTTAGGG | 83 |
| 14 | 17 | 943127 | LOX100130876 | AAATAACCGTCGGTTTCTTAAGG | 84 |
| 15 | 7 | 72574897 | TYW1B | GATCCGATGCAATTTTGGGAAGG | 85 |
| 16 | 13 | 19073987 | LOC107984132 | GGAAAGCGCAGAAAAGTAAAAGG | 86 |
| 17 | 19 | 58005513 | LOC100128398 | AAGAGTTATTGTCAATAGAAAGG | 87 |
| 18 | 19 | 58005993 | LOC100128398 | CAAAGAAATGTACTGCCTTACGG | 88 |
| 19 | 7 | 2434356 | CHST12 | CCTCTGACTTGACTTCAAACAGG | 89 |
| 20 | 16 | 31193648 | RUS | GTGGGTAGGTCCAGTTTGGGGGG | 90 |
| 21 | 16 | 31193383 | FUS | ACAAAGAAACCAGCAGTGGCAGG | 91 |

TABLE 11-continued

| Target No. | Chromosome | Location | Gene name | Target sequence (23nt) | SEQ ID NO |
|---|---|---|---|---|---|
| 22 | 7 | 1233674 | UNCX | CCTGAACTCGGGACTCGACCAGG | 92 |
| 23 | 7 | 1596749 | LOX105375122 | CCAACCAGGTACCCTGTGCCAGG | 93 |
| 24 | 12 | 908894 | WNK1 | ACTGGTTATTTCTTGCCAGAGGG | 94 |
| 25 | 12 | 909294 | WNK1 | GAACCCAGTGAAAAATACCAGGG | 95 |
| 26 | 1 | 25281171 | CLIC4 | CCCTGGCTACCTCCCCTACCCGG | 96 |
| 27 | 1 | 25281244 | CLIC4 | GAGGTAGCTTGCCATCTCTCAGG | 97 |
| 28 | 13 | 19131269 | CENPIP1 | CTATTCACTTGTGTTACAGGAGG | 98 |
| 29 | 13 | 20002951 | ZMYM2 | GTAGGCTGCTGTTGGACAGACGG | 99 |
| 30 | 5 | 202864 | CCDC127 | GGCAAGGGTCTTGATGCATCAGG | 100 |
| 31 | 5 | 202926 | CCDC127 | CCGAAAAAATGACTTTTTAGGGG | 101 |
| 32 | 12 | 884137 | WNK1 | ACTCAAGTTGTTCATTCTGCGGG | 102 |
| 33 | 12 | 674075 | LOC105369597 | GCCATGGTGAAGGTGAAATCAGG | 103 |
| 34 | 13 | 18178734 | LOC107687186 | CTGAATTACAACAAATTGCAAGG | 104 |
| 35 | 14 | 20457546 | APEX1 | AAGAAGGAATGGTAGTTGAGGGG | 105 |
| 36 | 14 | 20457653 | APEX1 | AGCCCAAGATTTTTTATTTGAGG | 106 |
| 37 | 1 | 25684228 | RSRP1 | ATATAGGATTTAGAAACCAAGGG | 107 |
| 38 | 8 | 3000119 | CSMD1 | ACATTTTTAGCTGGCCACTGCGG | 108 |
| 39 | 8 | 3087237 | CSMD1 | GAATACCCCCATTCTTCAGGGGG | 109 |
| 40 | 9 | 112718012 | INIP | AGAGCAGCGATTGTAAGGAGAGG | 110 |
| 41 | 9 | 14020 | DDX11L5 | AAAAGATCCCCATGGCCACAGGG | 111 |
| 42 | 3 | 173963325 | NLGN1 | AACGAATATTCTCAGACCACAGG | 112 |
| 43 | 1 | 61097979 | LOC105378763 | GGGAGGAGAACAGGAAATAAGGG | 113 |
| 44 | 1 | 61097826 | LOC105378763 | ATTGAAACATATACGTGGTAAGG | 114 |
| 45 | 3 | 173963498 | NLGN1 | GTCTAATAGAAATATAGTACAGG | 115 |
| 46 | 1 | 25684090 | RSRP1 | GCTCTAATGTAAGTATATCCAGG | 116 |
| 47 | 11 | 3042164 | CARS | CAACAGCCTCACCAGGAACAAGG | 117 |
| 48 | 9 | 14020 | DDX11L5 | AAAAGATCCCCATGGCCACAGGG | 118 |
| 49 | 12 | 32393 | LOC107987170 | GGGTTGCCAGATTAAAAGACAGG | 119 |
| 50 | 2 | 32383384 | NLRC4 | GAGGGAGACACAAGTTGATAGGG | 120 |
| 51 | 20 | 964362 | RSPO4 | ACTCATACATCACCTCCTCCAGG | 121 |
| 52 | 5 | 359923 | AHRR | CCTTAATAAAGTATAACTTCAGG | 122 |
| 53 | 19 | 627446 | POLRMT | GAAACTGCCCCAAAACCGGCCGG | 123 |
| 54 | 19 | 627491 | POLRMT | AGGACTATGTGTGGCCAGTGAGG | 124 |
| 55 | 17 | 292463 | RPH3AL | ATTTTCAAAACAGCCCTATGGGG | 125 |
| 56 | 17 | 292509 | RPH3AL | CACAAGGGATCTGAGACTTGAGG | 126 |
| 57 | 4 | 888480 | GAK | ACTCAAGGACTGGCTCAGTGAGG | 127 |
| 58 | 4 | 888530 | GAK | CAGAGTCCCGGGAACAAGCCAGG | 128 |
| 59 | 8 | 2204833 | LOC105377782 | TTTACAGCTCTGAGAACTAAACG | 129 |
| 60 | 3 | 27160152 | NEK10 | AGACAAGCTGTCTTCCTTCAGGG | 130 |

TABLE 11-continued

| Target No. | Chromosome | Location | Gene name | Target sequence (23nt) | SEQ ID NO |
|---|---|---|---|---|---|
| 61 | 3 | 27160372 | NEK10 | ATCTGAAGATCATTGAAACAGGG | 131 |
| 62 | 20 | 964345 | RSPO4 | AAGGAAAGGCTTCCTGGAGGAGG | 132 |
| 63 | 2 | 32383454 | NLRC4 | GTCTCAGTCTTCCTTGTGGGAGG | 133 |
| 64 | 4 | 42789361 | LOC105374431 | AGATAAGCGATAGTACATGAGGG | 134 |
| 65 | 14 | 19916429 | LOC105370393 | GCAGTACACCTGAGGGAACAGGG | 135 |
| 66 | 14 | 19916499 | LOC105370393 | AAGAAAGCTACAGGAAAGCAGGG | 136 |
| 67 | 22 | 17678603 | BCL2L13 | ATTTCCAAGTCAACCTTATGAGG | 137 |
| 68 | 22 | 17678663 | BCL2L13 | CAAAGTACCTGTTACTTAACAGG | 138 |
| 69 | 12 | 133140444 | ZNF10 | AATAAGTCTTACCACGTGTCAGG | 139 |
| 70 | 12 | 133140502 | ZNF10 | ATTCCCACAATAACCCTATGAGG | 140 |
| 71 | 12 | 97515285 | RMST | ATAATGCCTTTTAGGTGATAAGG | 141 |
| 72 | 12 | 97515361 | RMST | GAGAATAGAAATAAGAAAAAAGG | 142 |
| 73 | 3 | 114911114 | LOC101926886 | CAAACAAAATAATTGGCTCAGGG | 143 |
| 74 | 3 | 114911188 | LOC101926886 | CAATCATAGCAGAAGGTGAAGGG | 144 |
| 75 | 4 | 42789433 | LOC105374431 | CTTTAAAATGAGGTACTAGGGGG | 145 |
| 76 | 3 | 36995716 | MLH1 | AGGGAATGAAAGTGAAGATGGGG | 146 |
| 77 | 2 | 23847019 | KLHL29 | GAGAGACCGCTCAGGCTGGAGGG | 147 |
| 78 | 3 | 36995868 | MLH1 | GATCAATTTACATCAAACTAGGG | 148 |
| 79 | 4 | 3343318 | RGS12 | ATCCCCACAAATACTCTACGAGG | 149 |
| 80 | 3 | 99413340 | COL8A1 | GATTCATTCTCAGTGCCATGGGG | 150 |
| 81 | 3 | 99413482 | COL8A1 | AGGCAATTGCAACCACTGAAGGG | 151 |
| 82 | 5 | 102556075 | — | GAAATATGACTGGAAGTAAAGGG | 152 |
| 83 | 5 | 102556078 | — | CTTCCAGTCATATTTCTAAAGGG | 153 |
| 84 | 5 | 152068990 | — | CCCTTATTACAATCCTGTGGGGG | 154 |
| 85 | 5 | 152068994 | — | CCCCCACAGGATTGTAATAAGGG | 155 |
| 86 | 1 | 88052746 | — | ATCTCCATAACAATCTTTGGGGG | 156 |
| 87 | 1 | 88052777 | — | CTATCCCCATTTTACAGATGAGG | 157 |
| 88 | 3 | 157350012 | — | CTGAGATTTGCGAAGAGTTAGGG | 158 |
| 89 | 3 | 157350043 | — | ATTAAATAGAGTCTTTTGAAGGG | 159 |
| 90 | 3 | 128213929 | — | ATATTAATTGCAAGTTTGGGGGG | 160 |
| 91 | 3 | 128213984 | — | GGCCAAGTGCGAAGTCAGAGGGG | 161 |
| 92 | 4 | 3634902 | — | GGGGTGAACACCCAAGATCCCGG | 162 |
| 93 | 4 | 3634954 | — | GGGTGGGCTCCTGGCAGGGCAGG | 163 |
| 94 | 14 | 19023974 | — | AAAAGGGGAAAGAGAGAAAGAGG | 164 |
| 95 | 6 | 254091 | — | AGAAGCATGCAAAACCGGCAAGG | 165 |
| 96 | 6 | 254343 | — | AAGAGGGGAGGTTGACTTTGGGG | 166 |
| 97 | 5 | 97245414 | — | GTCAAATAAAGAAATACACGGGG | 167 |
| 98 | 5 | 97245470 | — | GTCAAATAAAGAAAAATACGGGG | 168 |
| 99 | 20 | 156154 | — | ATGCATCTCAGTGGTTAACAGGG | 169 |

TABLE 11-continued

| Target No. | Chromosome | Location | Gene name | Target sequence (23nt) | SEQ ID NO |
|---|---|---|---|---|---|
| 100 | 8 | 296459 | — | ACCTCAGGCCTGATCATCAGGGG | 170 |
| 101 | 4 | 54520460 | — | CATACAGGGCTCTGTACCCAGGG | 171 |
| 102 | 4 | 54520536 | — | CAAAGACACTCACCCTGTTGGGG | 172 |
| 103 | 5 | 170399606 | — | AGAACACATACCCCTGGGCCGGG | 173 |
| 104 | 5 | 170399701 | — | ATAATAAAAGTATTTCCTCAGGG | 174 |
| 105 | 17 | 1919439 | — | AGCCGTGGTCAGTGAGAGGCAGG | 175 |
| 106 | 17 | 1919532 | — | GAGCTCATTAGCTTGGGGAGGGG | 176 |
| 107 | 4 | 96592551 | — | GGAAAAGTCATCTGCTACTAGGG | 177 |
| 108 | 9 | 7742784 | — | GAAAATAACTAAACTTCCCAGGG | 178 |
| 109 | 15 | 25637364 | — | AATTCTTTAAGTAATTTAAGAGG | 179 |
| 110 | 4 | 96592739 | — | ATTGTATTGTCATAAATTTGGGG | 180 |
| 111 | 9 | 7742966 | — | CTTAGTAGTCTCAGAACCAAGGG | 181 |
| 112 | 15 | 25637516 | — | AAAGGAGCACAAGTACAAACAGG | 182 |
| 113 | 18 | 561716 | — | AATGATGCAGTAATCGTGTAGGG | 183 |
| 114 | 5 | 136515115 | — | ACTTGACATAGTAAGAAACAGGG | 184 |
| 115 | 5 | 136515295 | — | ATAAAAGGAACTATTTACAAGGG | 185 |

TABLE 12

| No. | Strand | Type | primer F(5'-3') | SEQ ID NO | primer R(5'-3') | SEQ ID NO |
|---|---|---|---|---|---|---|
| 1 | negative | exon | GTGCTCCCATACCTGTGCTT | 186 | CTCACCCAACCTCCTGCTCT | 187 |
| 2 | positive | exon | GGCAGGCTGGGAACAGATTAT | 188 | GCAGAATCTTGCCTTTCCATTGT | 189 |
| 3 | negative | exon | TGCTGTGTACCCCCATTTGA | 190 | CTTCACCCAACTTGCACTGG | 191 |
| 4 | negative | exon | | | | |
| 5 | negative | exon | GTCAGCTACCTTTCCCATGTT | 192 | TGAAGTGTTTACGTCCTCCCAT | 193 |
| 6 | positive | exon | | | | |
| 7 | positive | exon | AAAAGATGCTGGACCTTGGC | 194 | CAGGATGAGCAGCACTTTGG | 195 |
| 8 | positive | exon | | | | |
| 9 | positive | exon | CGGGGCTCCTCCAAACCTG | 196 | CTCCATGGAGGCAGAGAGGC | 197 |
| 10 | positive | exon | CTGTAACGCTTAGGCTGCCA | 198 | CTGGCCTGTGAAAGGTACAC | 199 |
| 11 | positive | exon | | | | |
| 12 | positive | exon | TCAAGATGCAGAAAGTGGGC | 200 | CCTAGAGCCTGGTGAGACTT | 201 |
| 13 | negative | exon | ACAGGTCATCCAAGAGCGAG | 202 | AGGAGACCCAAGAGCCATGA | 203 |
| 14 | positive | exon | CAAGGCTGGGCAGAGTAACTT | 204 | TCCCTGGATTTACAGTGGGGTG | 205 |
| 15 | positive | exon | GTCGTGATATGAGAGGCCCG | 206 | TCACCTGGCCCTTGGATTTC | 207 |
| 16 | negative | exon | CACTGTCGGAGCTCACATCG | 208 | GCCTCCTTCCAGGGTTGATG | 209 |
| 17 | negative | exon | GCAGAAGCTGGACTTGCCTC | 210 | AACCCCCGAGATAGGAAGGG | 211 |
| 18 | negative | exon | | | | |
| 19 | negative | exon | CCGCACCTGTCTGTTTTTGG | 212 | GCTAGAGTGCAATGTCGCGA | 213 |
| 20 | positive | exon | CAACAGTAGGCGGAGAGTGG | 214 | GAGGCCAGTTCAAGACCAGC | 215 |
| 21 | negative | exon | | | | |
| 22 | negative | exon | GCCCTTCAAGCTGTCAGGTA | 216 | TCTCGCCACCTGGAACAAAG | 217 |

TABLE 12-continued

| No. | Strand | Type | primer F(5'-3') | SEQ ID NO | primer R(5'-3') | SEQ ID NO |
|---|---|---|---|---|---|---|
| 23 | positive | exon | GGGCTCTAATGGCTGTGTGT | 218 | CTTTTCCCTCGACCTCCACC | 219 |
| 24 | positive | exon | GGGAACTGCCTCCTTGCAGAA | 220 | TGGCAAAGTTACATGTCCGC | 221 |
| 25 | positive | exon | | | | |
| 26 | positive | exon | CGCTTTTCCTAACAGGCTACTCC | 222 | GCATTATGCACCAGTTTGGGG | 223 |
| 27 | positive | exon | | | | |
| 28 | positive | exon | ACGCCCTAATGAAATTCTAGCCC | 224 | GCTGTGCCGGACGATCAAAA | 225 |
| 29 | negative | exon | CCTCTCTGCTATGTTGCTGTTCC | 226 | GCCACCTGGACTTGATAGGG | 227 |
| 30 | positive | exon | AGCACACTGGACATTAGAAACAGG | 228 | GATTACAGGCGTGCGCTACC | 229 |
| 31 | positive | exon | | | | |
| 32 | positive | exon | CCAATTCCTGCGTCTTCCATGCC | 230 | CAACATAGCAGAGGCACTGTAG | 231 |
| 33 | positive | exon | GAACCCTTATGGTGGGCTGTGG | 232 | GGGATGTCAGTGCTGTTGTGCAG | 233 |
| 34 | positive | exon | GTCTTTTTCCAGCCTGAGCCAGG | 234 | GTCTGCCAAGCTAAGGCTCTCAC | 235 |
| 35 | negative | exon | GCTTCCCCAGTCTTGCCAGTTGT | 236 | CCACTGTACCCTTCCTTGTCCGA | 237 |
| 36 | positive | exon | | | | |
| 37 | negative | exon | TGTCAGTAGGCCCCCAACTA | 238 | GCCTAACTGGCAAATGCCTTA | 239 |
| 38 | negative | exon | TGAACATGGCACCTCTCCTG | 240 | TGTTGCGCCTTCAATACTGT | 241 |
| 39 | positive | exon | GTTTGCATGGCCACTAGAAGG | 242 | CTCTCACAAAGGCAATGGCAC | 243 |
| 40 | negative | exon | ACAGGGCCATCTTGTGACAG | 244 | CCGCTAAAGTGCGAATCACG | 245 |
| 41 | positive | exon | GACGGAGCAGACCCATCTGC | 246 | GAGCCTAATGGCCCTTGGCAC | 247 |
| 42 | positive | exon | GCCCCCGTATTACCACTCTG | 248 | CCAGTGACATGGCCAAGATG | 249 |
| 43 | positive | exon | ACCCCTTCCAATACCATTTGAGA | 250 | TGCATAACTCGACAGATACACA | 251 |
| 44 | negative | exon | | | | |
| 45 | negative | exon | GCCCCCGTATTACCACTCTG | 252 | CCAGTGACATGGCCAAGATG | 253 |
| 46 | negative | exon | TGTCAGTAGGCCCCCAACTA | 254 | GCCTAACTGGCAAATGCCTTA | 255 |
| 47 | negative | exon | GTCCGAGAGACAAGCCAGGG | 256 | GATCCTGCTCTCTCTGCCTCC | 257 |
| 48 | positive | exon | GACGGAGCAGACCCATCTGC | 258 | GAGCCTAATGGCCCTTGGCAC | 259 |
| 49 | positive | exon | CAGTCAAGTCCAGCAGTTGTCCC | 260 | GAGTAGGGTGGCCAGAGGCAG | 261 |
| 50 | negative | intron | CCCACTCCACTTTGTTCCCAG | 262 | TCCTGGGCCCAATCATTCTG | 263 |
| 51 | negative | intron | AGGGTTTGAGGGGTTCAGTC | 264 | ACTTGACTCCCAACTCAGGC | 265 |
| 52 | negative | intron | TAGGTGGGCAAGAACAGAGG | 266 | TTCAGCACAGAGAGGGACAG | 267 |
| 53 | negative | intron | CTCCCAGGTTCACTCCATCC | 268 | GGCCACGTATTCTAACCAGC | 269 |
| 54 | negative | intron | | | | |
| 55 | positive | intron | TTGGAGAAGCATCACCTGCC | 270 | CGGGCTGTGTCCTAACGAAT | 271 |
| 56 | positive | intron | | | | |
| 57 | positive | intron | ACATTCCCAGTGTTCCGTGAG | 272 | CATCCAGTCCGTCGCTAAGT | 273 |
| 58 | positive | intron | | | | |
| 59 | negative | intron | CACCCCAACAACTTCTGGGG | 274 | AGCATGGTGCAGAATAGTGTGT | 275 |
| 60 | negative | intron | GGATTACCTGGGAGGGAGTCA | 276 | GGTTGATGTCCACCCCTTCA | 277 |
| 61 | negative | intron | | | | |
| 62 | positive | intron | AGGGTTTGAGGGGTTCAGTC | 278 | ACTTGACTCCCAACTCAGGC | 279 |
| 63 | negative | intron | CCCACTCCACTTTGTTCCCAG | 280 | TCCTGGGCCCAATCATTCTG | 281 |
| 64 | positive | intron | AGTTAATGGGTGCAGCACAC | 282 | TCCCAGCAAGTATTCAGCAACA | 283 |
| 65 | positive | intron | GCCAGCCCCTGATTCTTCAG | 284 | AGTGAATTATGTTGGCTTGGCA | 285 |
| 66 | positive | intron | | | | |

TABLE 12-continued

| No. | Strand | Type | primer F(5'-3') | SEQ ID NO | primer R(5'-3') | SEQ ID NO |
|---|---|---|---|---|---|---|
| 67 | negative | intron | AGATGACGAGAGCACAGCCT | 286 | GGGCCACTAAGTTGCAGGTC | 287 |
| 68 | negative | intron | | | | |
| 69 | positive | intron | GCAGTGGCTCACACCTGTAGTTC | 288 | CAGATCTCCAGAATTCTCCTGCTG | 289 |
| 70 | positive | intron | | | | |
| 71 | negative | intron | TAAGAAGCCTATGGGGAGCAG | 290 | GGCAAGGTCCCTGAACAGACATG | 291 |
| 72 | positive | intron | | | | |
| 73 | positive | intron | CCTCCCAGCCATGCTTCCTGTTA | 292 | AGTTTGGATGCTTGCTCCCTCC | 293 |
| 74 | positive | intron | | | | |
| 75 | negative | intron | AGTTAATGGGTGCAGCACAC | 294 | TCCCAGCAAGTATTCAGCAACA | 295 |
| 76 | positive | intron | TGGAGGTTCCAAGGGACCAG | 296 | AAGACTCCAGGAGGCCATGG | 297 |
| 77 | negative | intron | AAGCCGAAAGCCTACACCTC | 298 | GGACATTCGAAGCCCGTGTA | 299 |
| 78 | positive | intron | TGGAGGTTCCAAGGGACCAG | 300 | AAGACTCCAGGAGGCCATGG | 301 |
| 79 | positive | intron | CAGCGTCCCATGCACATTTGGG | 302 | GAGAGGACAGCACGGGCAGG | 303 |
| 80 | positive | intron | GTGGCCAGGGTGGAGGATAAG | 304 | CTCTGGCTCCTTTGATACCTCCG | 305 |
| 81 | positive | intron | | | | |
| 82 | negative | intergenic | CCATGACCCACAGAAACTAGAA | 306 | TCACCACCATCTCACCTTTG | 307 |
| 83 | positive | intergenic | | | | |
| 84 | positive | intergenic | GGAGGCATTTACAGTGCAGG | 308 | AATGCAGGTGAGGCCATTGT | 309 |
| 85 | negative | intergenic | | | | |
| 86 | positive | intergenic | GGGGACACATTCAGACCCTA | 310 | CTCAGTGTGAACGCGATTGG | 311 |
| 87 | positive | intergenic | | | | |
| 88 | negative | intergenic | GCTCCCTGTTTTGCTCCTTC | 312 | CCAACTCCAAGCCAAGCATT | 313 |
| 89 | negative | intergenic | | | | |
| 90 | negative | intergenic | GCTGTGAGGAGAAAAGAGAGCA | 314 | GTGGTGAAAGGCCATGAGGG | 315 |
| 91 | negative | intergenic | | | | |
| 92 | negative | intergenic | AGGGGACCCCCTGTAGAAC | 316 | GGGCCTCAAGTTTGTTTTGC | 317 |
| 93 | negative | | | | | |
| 94 | negative | intergenic | ATGGCTTTTTCAGGATTCCAAACT | 318 | GCAGCCCCTACAGAAATGAGT | 319 |
| 95 | positive | intergenic | GCAGGCTGGTAACTGTGACT | 320 | ACCTGCTGCAGAACTGAAGC | 321 |
| 96 | positive | intergenic | | | | |
| 97 | positive | intergenic | CCAATGGTGATGAGACAGCGT | 322 | GTGGAGGGTGTCCTGGTTCT | 323 |
| 98 | positive | intergenic | | | | |
| 99 | positive | intergenic | CTGCCCTCCAGTTGTGACTT | 324 | TGCCACAAGGAATCGATGTT | 325 |
| 100 | negative | intergenic | TGTCTAAGGCCACGACCACAAGC | 326 | CCTTCTTGGCACTTCTCGGTGGT | 327 |
| 101 | negative | intergenic | GGCCCAGAACCTTGCTCTTTGAG | 328 | AAGGAGCTGTGCTGTGCAGGTA | 329 |
| 102 | positive | intergenic | | | | |
| 103 | negative | intergenic | CTGCACCACCACACCTGGCTAAT | 330 | AGAACAGAGCAGTGGGCAACAGG | 331 |
| 104 | negative | intergenic | | | | |
| 105 | positive | intergenic | AGAGGGGCACTCGGGAAGAGATA | 332 | GGAGGACTTCTTCCCTGTTGGTC | 333 |
| 106 | positive | intergenic | | | | |
| 107 | positive | intergenic | TAAACAGGGAAGCGTGGAAGA | 334 | TGATGCTTCACCTCAGTGTCT | 335 |
| 108 | negative | intergenic | ATGATTGGGTTCTGCTGAGGG | 336 | AGACCACCTAAAACATTGGCT | 337 |
| 109 | negative | intergenic | GGCCTGACCCTCCAGATCTT | 338 | GCACTATGCGATCTCCTGGC | 339 |
| 110 | positive | intergenic | TAAACAGGGAAGCGTGGAAGA | 340 | TGATGCTTCACCTCAGTGTCT | 341 |
| 111 | positive | intergenic | ATGATTGGGTTCTGCTGAGGG | 342 | AGACCACCTAAAACATTGGCT | 343 |
| 112 | positive | intergenic | GGCCTGACCCTCCAGATCTT | 344 | GCACTATGCGATCTCCTGGC | 345 |

TABLE 12-continued

| No. | Strand | Type | primer F(5'-3') | SEQ ID NO | primer R(5'-3') | SEQ ID NO |
|---|---|---|---|---|---|---|
| 113 | positive | intergenic | ACAAATCCCCTCATCCCAACG | 346 | AAGCTCACTCACCCACCACT | 347 |
| 114 | positive | intergenic | GCAACAATCGCCATTCCTCACCC | 348 | GTGGCCCTCTTATAGCTCTAGG | 349 |
| 115 | positive | intergenic | | | | |

Figure 25:
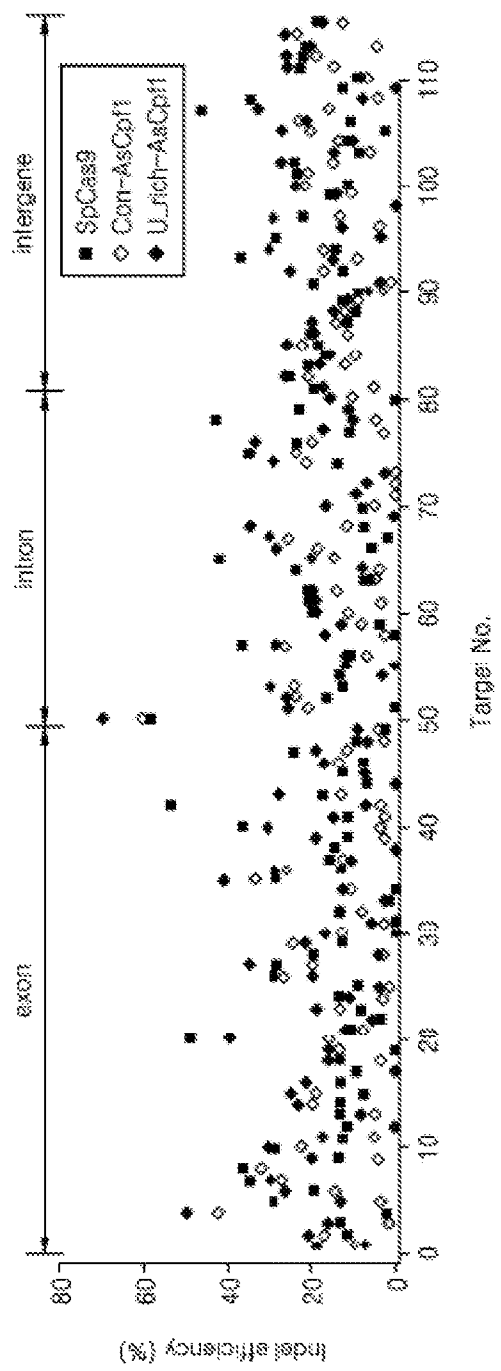
FIGS. 25 and 26 illustrate the results of comparing the genome editing efficiencies of CRISPR/AsCpf1 and CRISPR/SpCas9 on a large scale.
Figure 26:
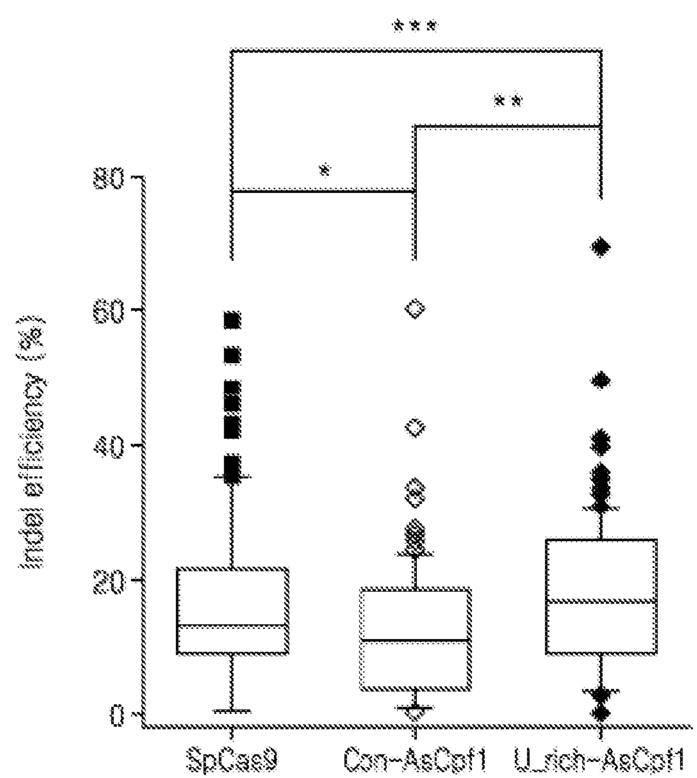

The indel efficiencies in the targets investigated in FIGS. 25 and 26 are represented by dot and box-and-whisker plots, respectively. For each target, the indel efficiencies of AsCpf1 (Con-AsCpf1) having SpCas9 and a standard crRNA (canonical crRNA), and AsCpf1 (U_rich-AsCpf1) having a crRNA including a U-repeat sequence were investigated. Two of the 115 targets did not exhibit the indel mutation by the gene editing system, but the remaining 113 targets exhibited a detectable level of indel mutation in at least one of the tested systems (98.2% coverage).

For the first time through the Examples of the present invention, the indel efficiencies of Cas9 and Cpf1 were compared with statistically sufficient size samples. As a result of the statistical analysis for these large data, the following conclusions are obtained:

1) Unlike the fact that the efficiency of Cpf1 is known to be similar to that of SpCas9, the overall efficiency of AsCpf1 induced by the standard crRNA was lower than the efficiency of SpCas9 (p=0.003).

2) The U-rich crRNA significantly improved the indel efficiency of AsCpf1 (p=0.00003), and the efficiency of AsCpf1 improved by the U-rich crRNA was almost similar to the efficiency of SpCas9 (p=0.29).

3) In the case of a target in which no indel mutation due to the standard crRNA was detected, the use of U-rich crRNA did not affect the efficiency improvement. However, in the case of a target with a detectable mutation, the target of 90.3% (94/104) showed increased efficiency by U-rich crRNA, and the increase/decrease range was 1.07 to 12.98 times, and the average increase rate was 2.31.

4) Cpf1 and Cas9 are complementary to each other as a genome editing tool. AsCpf1 induced by U-rich crRNA efficiently was not induced to be mutated by SpCas9, or efficiently mutated targets with low indel efficiency, and vice versa.

From these results, it could be seen that the CRISPR/Cpf1 system, which uses U-rich crRNA as a highly efficient and predictable method, can be used as a genome editing tool to complement the CRISPR/Cas9 system.

EXAMPLE 4

Off-Target Effect by U-Rich crRNA

The high target specificity and low off-target activity of Cpf1 have been known through several studies, and it has been known that particularly, both AsCpf and LbCpf1 are highly specific for genome editing in human cells and have less off-target activity than SpCas9. While the U-rich crRNA shows a significant increase in activity in on-target editing, there is a concern that a shortened target length (23 to 20 nt) improves the target specificity of Cpf1, but may increase the off-target activity. To solve this problem, the present inventors compared the off-target activity of AsCpf1 induced by the U-rich crRNA in a biased manner with that induced by a standard 23-nt target-complementary crRNA. Since the genome-wide target specificity of Cpf1 has been extensively investigated, the biased analysis of off-target activity can fully evaluate the potential specificity problems which may be caused by the U-rich crRNA.

Figure 27:
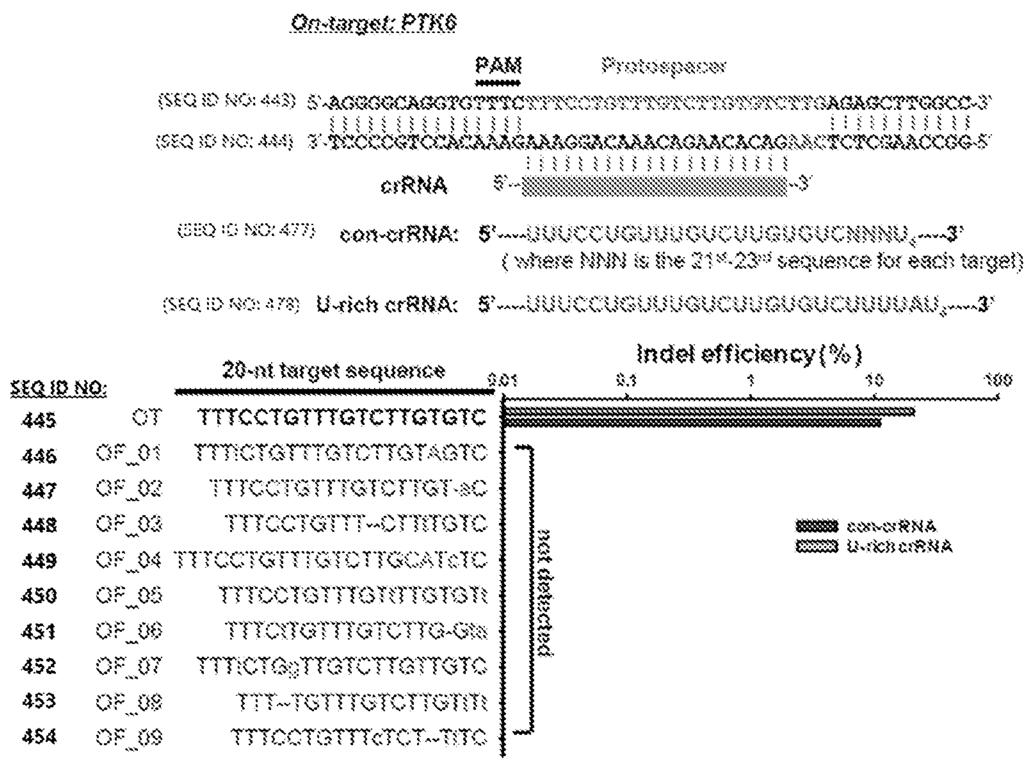
FIGS. 27 to 33 illustrate the results of experiments confirming that the U-rich crRNA according to the present invention does not affect the off-target effect.

Using Cas-OFFinder, nine potential off-target sites with the smallest bulge and a sequence which did not match the target sequence of phospho-tyrosine kinase 6 (PTK6) were selected. Next, the incidence rate of mutation due to AsCpf1 was investigated in HEK-293T cells, and the differences in indel efficiency between the standard 23-nt crRNA (con-crRNA) and the U-rich crRNA were compared. As a result of the deep sequencing analysis, it could be seen that the on-target indel efficiency of the present invention by the U-rich crRNA was increased by 2.61 times as in the results shown in FIGS. 2 and 3 (FIG. 27).

However, no indel mutation was observed within the target sequence for all potential off-targets. Since the single nucleotide polymorphism (SNP) appeared at the same or similar level in AsCpf1 non-treated cells, the difference in reference sequence is likely to be due to the single nucleotide polymorphism (see Tables 4 to 9). From this result, it could be seen that the use of the U-rich crRNA does not affect the off-target activity of AsCpf1.

Next, the present inventors examined whether the off-target level changes in the DNMT1 site using a crRNA having a single base that does not match the protospacer sequence. Significant and considerable levels of tolerance were observed for discrepancies in the 3'-end and the middle site (positions 8 to 10) of the crRNA.

Figure 28:
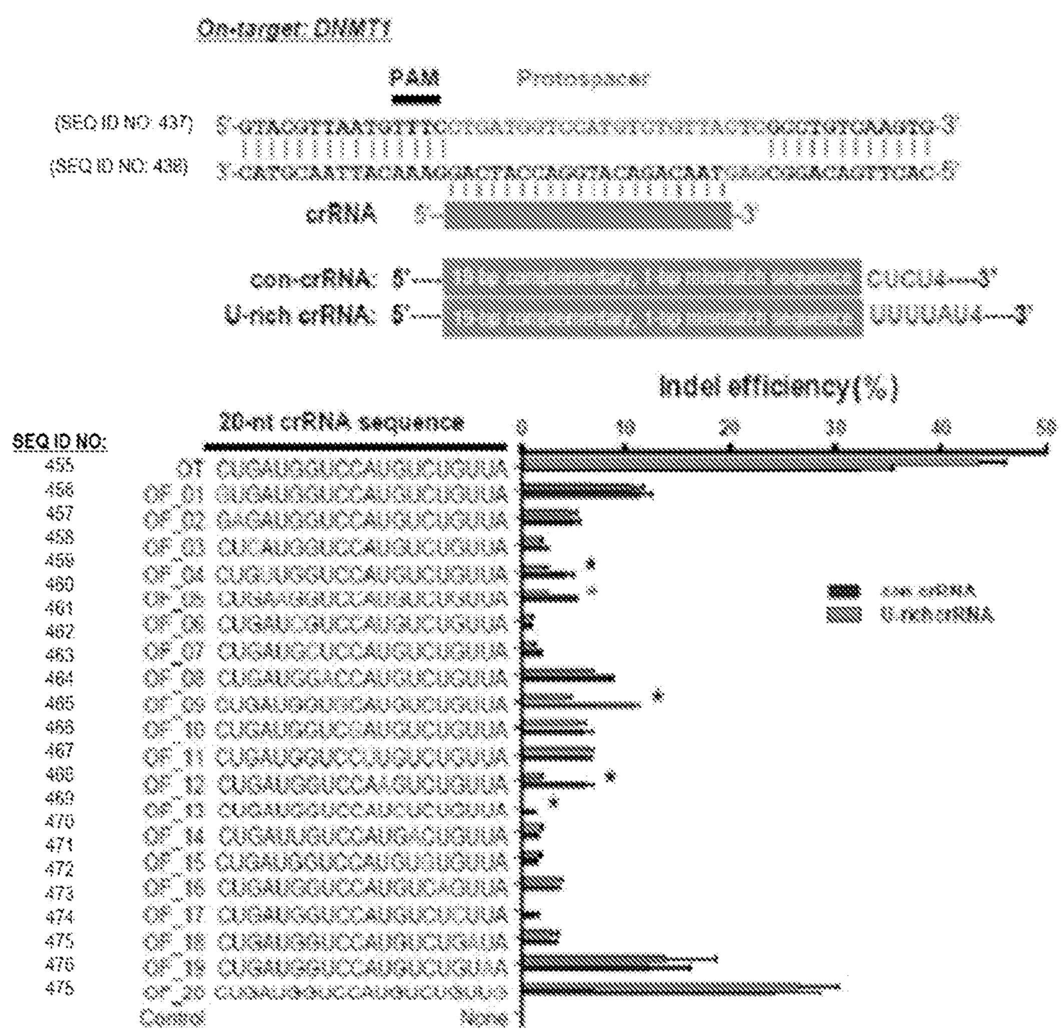

Even though the higher level of off-target in the aforementioned region appeared, it has been confirmed through repetitive experiments that off-target indel mutation occurs widely throughout the target position target site (FIG. 28). Interestingly, the use of the U-rich crRNA reduced the resistance to single nucleotide mismatches at most target positions except for the 3'-end region (18 to 20 positions). This result coincides with studies in the related art showing that cleaved guide RNAs improve the target specificity of SpCas9. The present inventors observed significantly higher off-target activity at the 18 to 20 position as reported in the related art, and confirmed that the U-rich crRNA slightly worsened off-target activity in this region. Nevertheless, in consideration of the fact that the ratio of the off-target to the target mutation level is actually important, the present inventors found that even the use of the U-rich crRNA does not significantly impair the intrinsic level of Cpf1 specificity.

Figure 29:
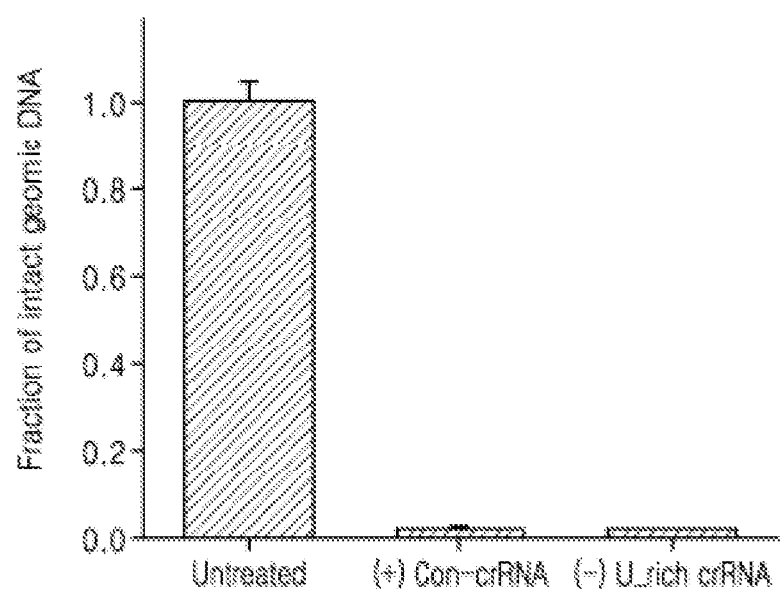
Figure 30:
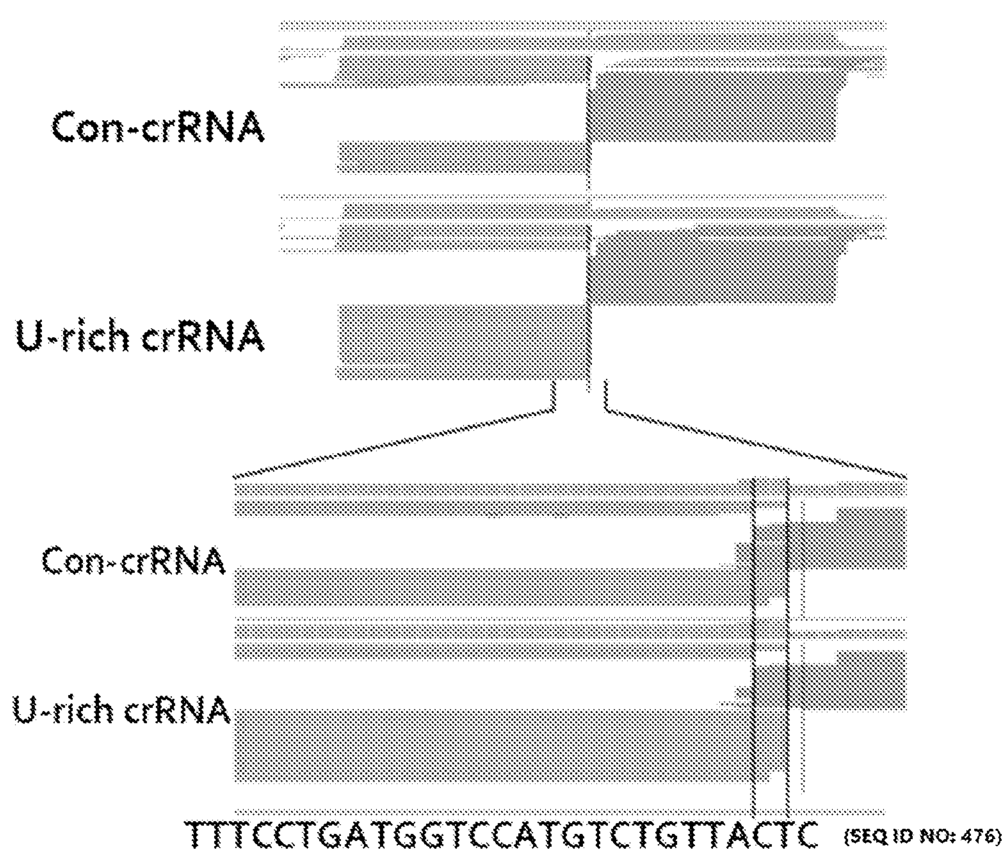

Finally, in order to monitor changes in off-target activity according to the crRNA structure, a non-biased overall genomic assay for Cpf1 specificity was performed by cleavage genome sequencing technique (Digenome-seq) analysis. Cell-free genomic DNA isolated from HEK-293T cells was provided for in vitro cleavage by AsCpf1-crRNA ribonucleoprotein complex. As a result of a quantitative real-time PCR analysis, it was confirmed that over 98% of the genomic DNA was degraded by the AsCpf1-standard crRNA ribonucleoprotein complex as well as by the AsCpf1-U-rich crRNA (FIGS. 29 and 30).

Figure 31:
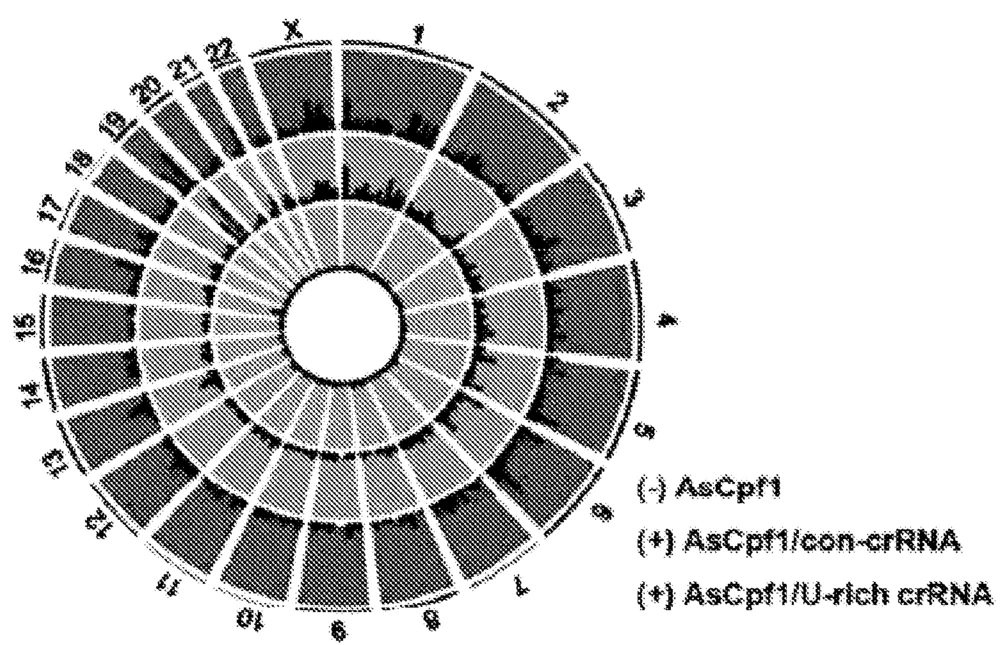

Subsequently, the cleaved product was applied to the whole genome sequencing, and the sequence data were aligned against the human reference genomic database (GRCh38.p11). Through an integrated genomic viewer (IGV), typical cleavage patterns at positions 18-20 of the non-target strand and at position 22 of the target strand were confirmed. A computer analysis was performed using the Digenome-seq program to find off-target sites where the DNA cleavage score and the discrepancy were confirmed to be 2.5 or more and 6 or less, respectively. The confirmed sites are listed in Table 13 (Con-crRNA) and Table 14 (U-rich-crRNA), and off-target sites are shown in the entire genome Circos plot (FIG. 31).

TABLE 13

| Chromosome | Location | DNA Cleavage score | Target sequence | Sequence listing |
|---|---|---|---|---|
| Chr19 | 43767815 | 15.8 | TTTACTGATGGTCCAaacaTcTaA | 350 |
| Chr1 | 10179491 | 10.4 | TTTACTGATGGTCCATccCTtTTA | 351 |
| Chr19 | 43263943 | 9.1 | TTTACTGATGGTCCAaacaTcTaA | 352 |
| Chr1 | 177026436 | 8.4 | TTTGCTGATGGTCgATtTaTacTg | 353 |
| Chr19 | 10244444 | 8.2 | TTTCCTGATGGTCCATGTCTGTTA | 354 |
| Chr6 | 16517291 | 7.7 | ATTCCTGATGaTCCATGcCTGcat | 355 |
| Chr19 | 43416520 | 6.9 | TTTACTGATGGTCCAaacaTcTaA | 356 |
| Chr5 | 39969437 | 6.7 | TCTCCTGATGGTCCATacCTGTTA | 357 |
| Chr2 | 233034313 | 6.2 | TTTAgTGATaGTCCATGTCTGcag | 358 |
| Chr19 | 43353967 | 6 | TTTACTGATGGTCCAaacaTcTgA | 359 |
| Chr6 | 141623485 | 5.7 | TTTGCTGATGGTCtATagCTaTcA | 360 |
| Chr13 | 70187460 | 5.6 | TTTCCTGATGGTCCAcactTGTTg | 361 |
| Chr21 | 44021964 | 5.6 | TTTCCTGATGGTCtAcacCTGTTg | 362 |
| Chr5 | 163936302 | 5.6 | TTTCCTGATGGTCtATtTtTccTt | 363 |
| Chr19 | 43377706 | 5.5 | TTTACTGATGGTCCAaacaTcTaA | 364 |
| ChrX | 81346070 | 5.4 | TTTCCTGATGGTCCAcacCTaTTg | 365 |
| ChrX | 115862098 | 5.1 | TTTCaTGATGGTCCATacCTGTTA | 366 |
| Chr1 | 213377379 | 5.1 | TTTCCTGATGGTCCATGTCTGaat | 367 |
| Chr4 | 151678397 | 4.7 | TTTGCTGATGGTCtcTtTaacTTA | 368 |
| Chr1 | 89819958 | 4.5 | TTTCCTGATGGcCCATacCTGTTA | 369 |
| Chr1 | 242619943 | 4.3 | TTTGgTGATGGTCtATaTCaGagA | 370 |
| Chr2 | 89591302 | 4.2 | TTTCCTGATGGTCCAcacCTtTTg | 371 |
| Chr13 | 81006434 | 4 | TTTCCTGATGGTCCAcactTGTgg | 372 |
| ChrX | 97546178 | 3.9 | TTTCCTGATGGTCCAcGcCTGTTA | 373 |
| Chr22 | 27745385 | 3.8 | TTTCCTGATGGTCCAcactTaTTA | 374 |
| Chr3 | 96050499 | 3.8 | TTTCCTGATGGTCCATactTGTTg | 375 |
| Chr1 | 238343056 | 3.4 | TTTCCTGATGGTCCAcacCTaTTg | 376 |
| Chr3 | 195961223 | 3.4 | TTACCTGATGtTCCATGTCcagTg | 377 |
| Chr13 | 82088076 | 3.4 | TTTCCcGATGGTCCAcaTCTGTTA | 378 |
| Chr17 | 53836590 | 3.2 | TTTACTGATGGTCCATacCTcgTA | 379 |
| Chr1 | 146123498 | 3.2 | TTTCCTGATGGTCCAcacCTGTTg | 380 |
| Chr2 | 4463241 | 3.2 | TTTAgTGATGGTCCcTaTtTcTTc | 381 |
| Chr3 | 142979810 | 3.1 | TCTCCTGATGGTCCAcGcCTGTTA | 382 |
| Chr4 | 125429316 | 3 | TTTCCTGATGGTCCAcacCTaTTg | 383 |

TABLE 13-continued

| Chromosome | Location | DNA Cleavage score | Target sequence | Sequence listing |
|---|---|---|---|---|
| Chr7 | 68777908 | 3 | TTTCCTGcTGGTCCATGTCTaaTA | 384 |
| Chr1 | 236623993 | 3 | TTTACTGATGaTCCATGTCTaaac | 385 |
| ChrX | 92676365 | 3 | TTTCCTGATGGTCCATacCTGTTA | 386 |
| Chr11 | 26124230 | 2.9 | TTTCCTGATGGTCCAcaTCTGTTA | 387 |
| Chr4 | 84421821 | 2.8 | TTTCCTGATGGTCCAcacCTtTTg | 388 |
| Chr6 | 138526961 | 2.6 | TTTCCTGATGGTCtgTtTtTGTag | 389 |
| Chr5 | 35891132 | 2.6 | TTTCCTGATGGTCtAcacCTGTTg | 390 |

TABLE 14

| Chromosome | Location | DNA Cleavage score | Target sequence | SEQ ID NO |
|---|---|---|---|---|
| Chr19 | 43767815 | 11.3 | TTTACTGATGGTCCAaacaTcTaA | 391 |
| Chr6 | 141623485 | 10.2 | TTTGCTGATGGTCtATagCTaTcA | 392 |
| Chr6 | 138526960 | 8.7 | TTTCCTGATGGTCtgTtTtTGTag | 393 |
| Chr19 | 10244444 | 7.8 | TTTCCTGATGGTCCATGTCTGTTA | 394 |
| Chr19 | 43263943 | 7.7 | TTTACTGATGGTCCAaacaTcTaA | 395 |
| Chr5 | 163936302 | 7.3 | TTTCCTGATGGTCtATtTtTccTt | 396 |
| ChrX | 92673750 | 7.3 | TTTCCTGATGGTCCAcagaTacTA | 397 |
| Chr21 | 44021964 | 6.9 | TTTCCTGATGGTCtAcacCTGTTg | 398 |
| Chr19 | 43435385 | 6.9 | TTTACTGATGGTCCAaacaTcTaA | 399 |
| Chr1 | 10179491 | 6.7 | TTTACTGATGGTCCATccCTtTTA | 400 |
| Chr19 | 43377706 | 6.6 | TTTACTGATGGTCCAaacaTcTaA | 401 |
| Chr3 | 122020326 | 6.5 | TTTACTGATGaTCtATaTtTacTA | 402 |
| Chr19 | 43416520 | 6.4 | TTTACTGATGGTCCAaacaTcTaA | 403 |
| Chr1 | 177026436 | 6.3 | TTTGCTGATGGTCgATtTaTacTg | 404 |
| Chr1 | 186592956 | 5.8 | TTTCCTcATGGTCCATGTCaGgac | 405 |
| Chr16 | 75745894 | 5.7 | TTTTCTGATGGTCCATacCTGTTA | 406 |
| Chr6 | 16517291 | 5.7 | ATTCCTGATGaTCCATGcCTGcat | 407 |
| Chr19 | 43353967 | 5.6 | TTTACTGATGGTCCAaacaTcTgA | 408 |
| ChrX | 115862098 | 5.6 | TTTCaTGATGGTCCATacCTGTTA | 409 |
| Chr1 | 236623991 | 4.9 | TTTACTGATGaTCCATGTCTaaac | 410 |
| Chr13 | 70187460 | 4.9 | TTTCCTGATGGTCCAcactTGTTg | 411 |
| Chr1 | 213377380 | 4.9 | TTTCCTGATGGTCCATGTCTGaat | 412 |
| Chr1 | 238343056 | 4.7 | TTTCCTGATGGTCCAcacCTaTTg | 413 |
| Chr5 | 35891131 | 4.5 | TTTCCTGATGGTCtAcacCTGTTg | 414 |
| ChrX | 97546178 | 4.2 | TTTCCTGATGGTCCAcGcCTGTTA | 415 |
| Chr17 | 53836590 | 4.1 | TTTACTGATGGTCCATacCTcgTA | 416 |
| ChrX | 94580341 | 4.1 | TTTCCTGATGGTCCAcactTGTTg | 417 |
| Chr2 | 89591301 | 4 | TTTCCTGATGGTCCAcacCTtTTg | 418 |

TABLE 14-continued

| Chromosome | Location | DNA Cleavage score | Target sequence | SEQ ID NO |
|---|---|---|---|---|
| Chr12 | 58560889 | 3.8 | TTTCCTGATGGTCtAcacCTGTTg | 419 |
| Chr13 | 81006434 | 3.8 | TTTCCTGATGGTCCAcactTGTgg | 420 |
| Chr6 | 154888710 | 3.7 | TTTACTaATGGTCCAaaTCctTcA | 421 |
| Chr4 | 151678397 | 3.6 | TTTGCTGATGGTCtcTtTaacTTA | 422 |
| Chr7 | 112920853 | 3.4 | TTTGCTGATGGTCtgTaTCTGTgA | 423 |
| Chr8 | 34932811 | 3.3 | TCTACTGATGGTCCtTaTtTGTTg | 424 |
| Chr4 | 31284788 | 3.2 | TTTCCTGATGaTCtATcTaTagTA | 425 |
| Chr3 | 135976149 | 3.1 | TTTGCTGATGGTCCcctTCTcccA | 426 |
| ChrX | 130910822 | 3.1 | TCTCCTGATGaTCCAcaTCTGTTA | 427 |
| Chr3 | 96050498 | 3 | TTTCCTGATGGTCCATactTGTTg | 428 |
| Chr7 | 68777909 | 2.9 | TTTCCTGcTGGTCCATGTCTaaTA | 429 |
| Chr4 | 84421821 | 2.9 | TTTCCTGATGGTCCAcacCTtTTg | 430 |
| ChrX | 92676365 | 2.8 | TTTCCTGATGGTCCATacCTGTTA | 431 |
| Chr5 | 178329 | 2.7 | TTTCCTGATGGTCCAcacCTGcTg | 432 |
| Chr11 | 26124230 | 2.7 | TTTCCTGATGGTCCAcaTCTGTTA | 433 |
| Chr6 | 147610255 | 2.7 | TTTCCTGATGGTCCAcacCTGcTg | 434 |
| Chr1 | 89819958 | 2.6 | TTTCCTGATGGcCCATacCTGTTA | 435 |
| Chr9 | 35488299 | 2.5 | TTTCCTGATGGTCCAcacaTGTTA | 436 |

Figure 32:
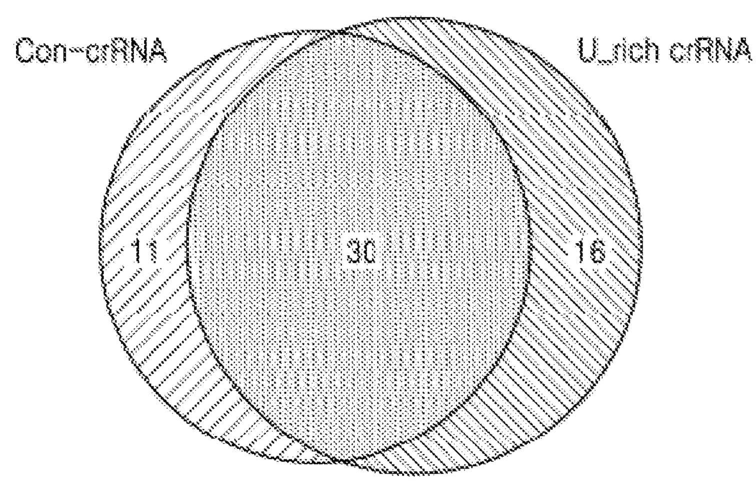

There was no remarkable difference in the number of off-target sites for the standard and the U-rich crRNA. 41 and 46 off-target sites were confirmed for the standard and the U-rich crRNA, respectively, of which 30 were commonly confirmed (FIG. 32).

Figure 33:
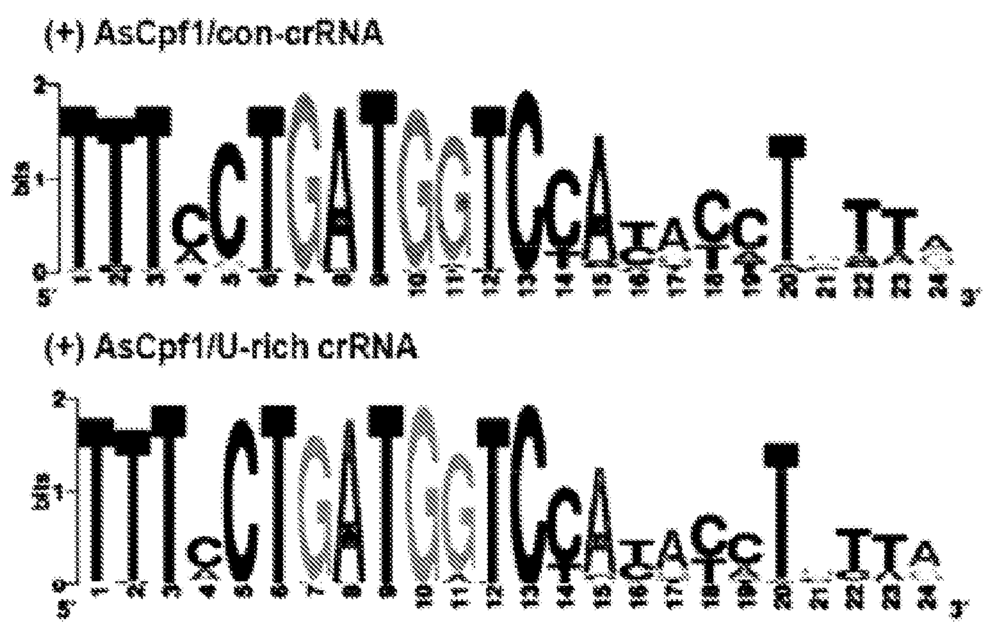

In the absence of crRNA, crRNA-dependent DNA cleavage was confirmed in that no cleavage site with a significant DNA cleavage score (>2.5) was produced. In addition, the overall off-target pattern of the entire genome Circos plot was almost identical for both crRNAs. Through sequence logo analysis, it was confirmed that the PAM proximal sequence was conserved identically and that both crRNAs have the same pattern which is more resistant to the PAM-distal sequence (FIG. 33).

From these results, it was confirmed that the high specificity of AsCpf1 was not impaired by the U-rich 3'-overhang.

EXAMPLE 5

Multi-Genome Editing of Cpf1 and Application of U-Rich crRNA to PAM-Mutation

Figure 34:
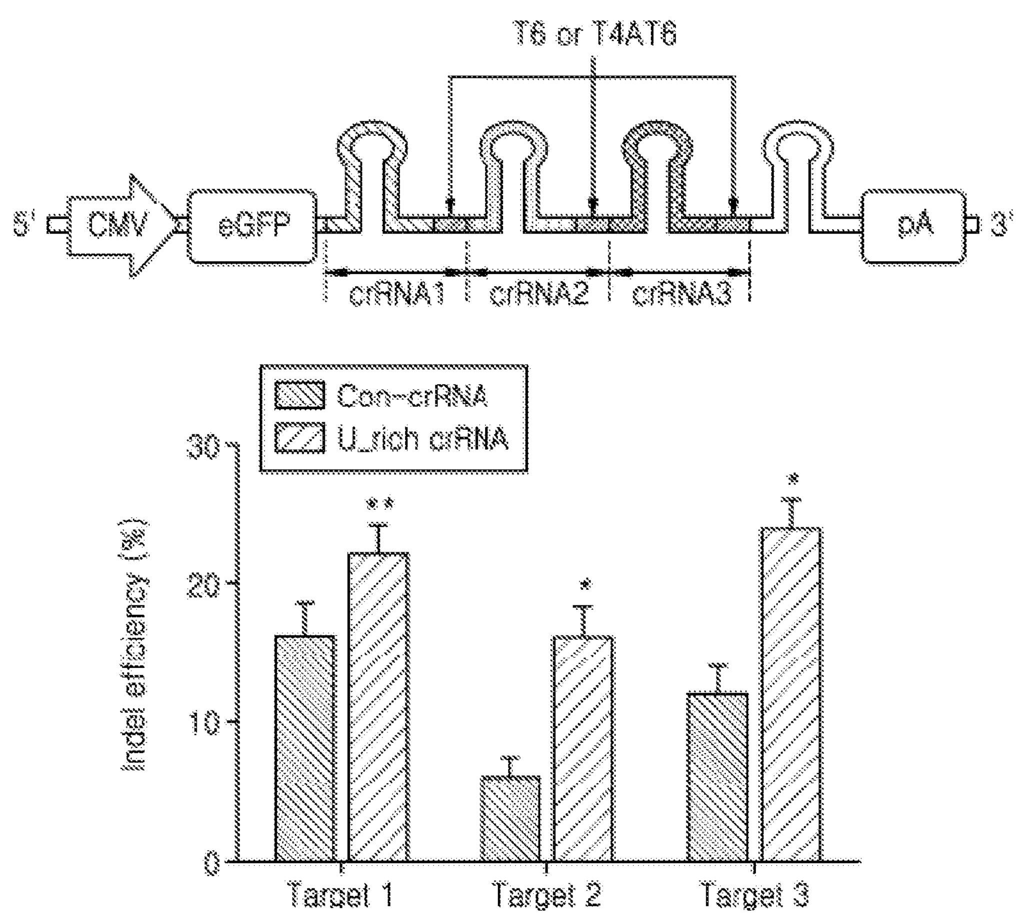
FIGS. 34 to 36 illustrate that the U-rich crRNA according to the present invention is applied to multiple genome editing and PAM-mutation.

To confirm whether the U-rich crRNA can be applied to multi-genome editing in recently reported mammals, the present inventors inserted a crRNA sequence having a 23=nt target complementary sequence into the 3'-UTR region of the eGFP gene. As a comparative example, a T-rich sequence was inserted between the 20-base target and the scaffold of an adjacent crRNA (FIG. 34).

As a result of investigating three of the targets included in the large-scale verification study in Example 3, it could be seen that these three targets showed similar levels of indel efficiencies to those investigated individually, and the indel efficiency was improved to a level similar to those shown in individual experimental results by inserting U-rich sequences.

Additional study results have been published in a group which created two AsCpf1 PAM variants having the mutations S542R/K607R (RR mutation) and S542R/K548V/N552R (RVR mutation) (Gao, L. et al. Engineered Cpf1 variants with altered PAM specificities. *Nat. Biotechnol.* 35, 789-792 (2017)). Since both of these variants are dependent on the PAM sequences TYCV and TATV, respectively, these variants remarkably lower the barrier that the target range of Cpf1 is essentially limited. The present inventors have confirmed whether the U-rich crRNA can improve the indel efficiency against the two AsCpf1 variants observed in wild-type AsCpf1.

Figure 35:
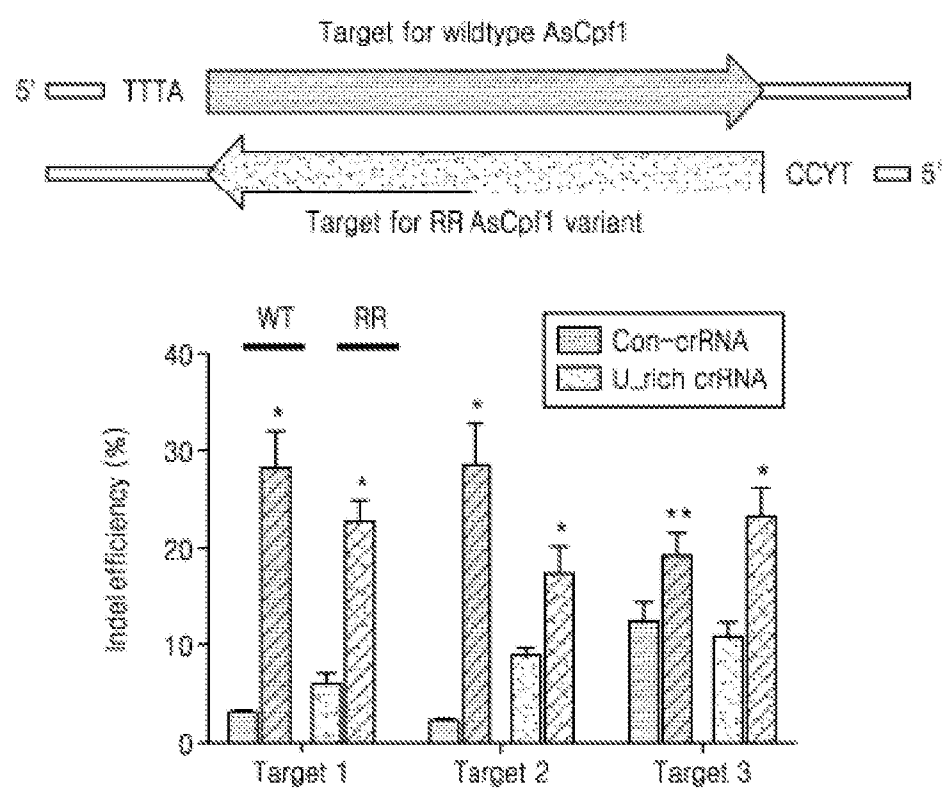

First, three sites were selected as common targets for WT AsCpf1 and RR mutations, and this target has a TTTA PAM sequence on one strand and a two TTCC and one TCCC sequence (TYCC) on the other strand (FIG. 35). As a result of the experiment, it could be seen that the U-rich crRNA enhanced the indel efficiency of AsCpf1 in all three cases, even though there was a difference in the degree of efficiency increase depending on the target. In Target 1 and Target 2, the RR variants exhibited higher indel efficiencies than WT AsCpf1 when guided by the standard crRNA, with a slight decrease in efficiency enhancement when guided by the U-rich crRNA. In target 3, however, the U-rich crRNA remarkably improved the indel level efficiency than RR variants.

Figure 36:
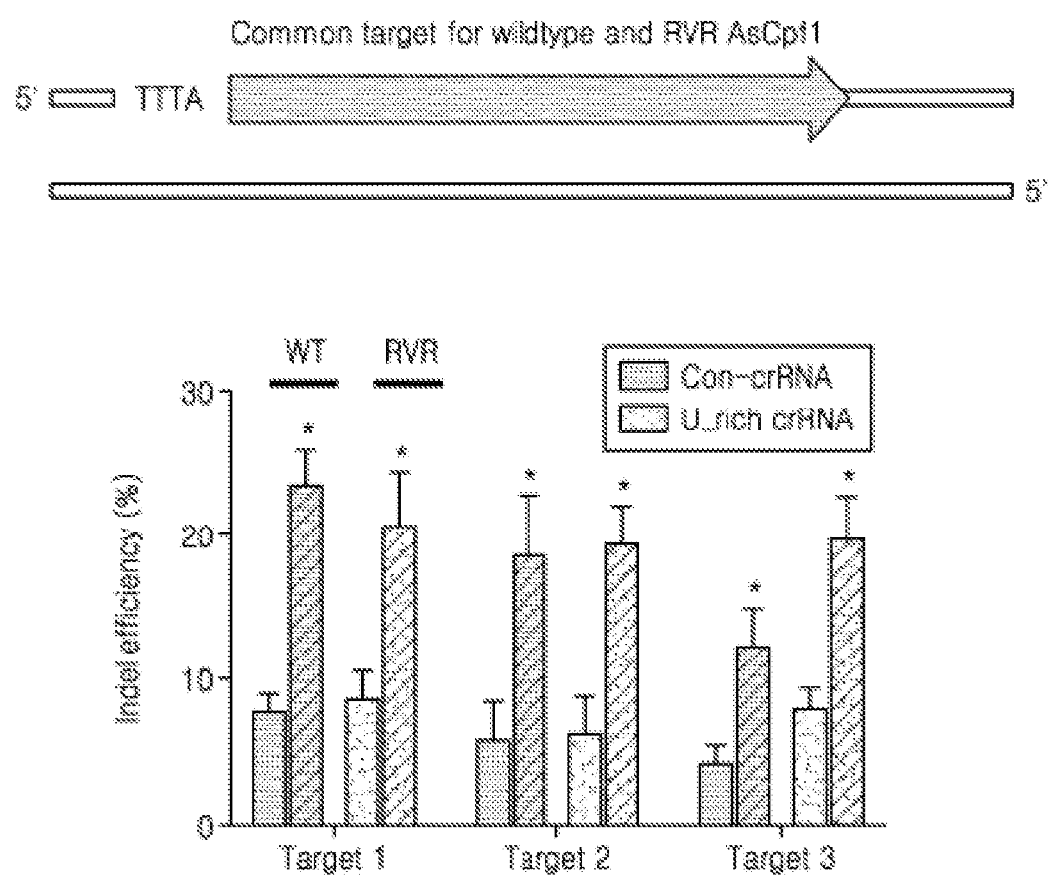

Next, the RVR AsCpf1 variant was compared with WT AsCpf1. Since RVR variants have the characteristic of recognizing TTTV PAM, WT and RVR variants share a single target having TTTA PAM (FIG. 36). As expected, the U-rich crRNA improved the indel efficiency in both WT and RVR variants. In this case, although the efficiency improvement percentages differ for each target, the enhancement of the indel efficiency of the U-rich crRNA was commonly observed regardless of the target and AsCpf1 forms.

From this, it could be seen that the U-rich crRNA can be used variously for genetic editing of multiple targets and for the use of Cpf1 variants in mammalian cells, thus making the CRISPR/Cpf1 system as a new genome editing tool which can be applied in a wider range.

EXAMPLE 6

Confirmation of Improved Binding Affinity of AsCpf1-U-Rich crRNA Complex

Figure 37:
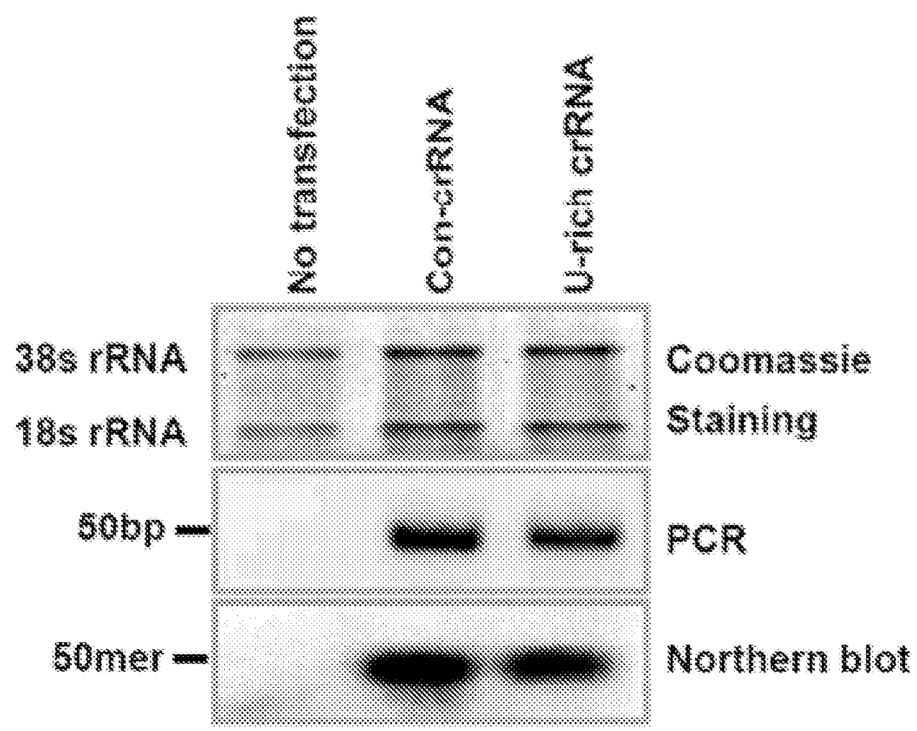
FIGS. 37 to 41 confirm the improved binding affinity of the AsCpf1-U-rich crRNA complex.

If the stability of the crRNA mainly increases the activity of Cpf1, there will be differences in the endogenous level or pattern of the crRNA according to the transfection of the PCR amplified product. In order to confirm whether the increased Cpf1 activity was due to improved stability of the crRNA or to direct regulation of Cpf1, the levels of crRNA were tracked by performing Northern blot analysis (FIG. 37).

As a result, no significant increase in endogenous crRNA levels due to the U-rich 3'-overhang was observed.

In addition, in order to eliminate the differential degradation of crRNA according to the 3'-overhang and the association of ribonuclease, for both Cas9 and Cpf1, a chemically modified guide RNA was used such that the four nucleotides at the 3'-end were covalently bonded to a phosphorothioate group. Through the treatment as described above, it is possible to eliminate the problem of nuclease tolerance by preventing the degradation of the guide RNA by the riboexonuclease, so that the effect of the U-rich 3'-overhang may be investigated.

Figure 38:
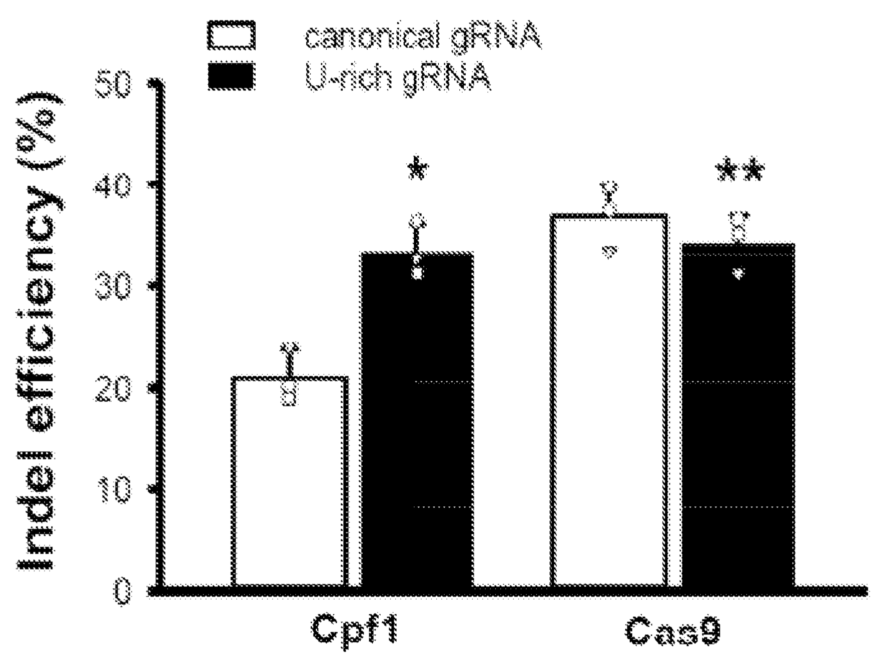
Figure 39:
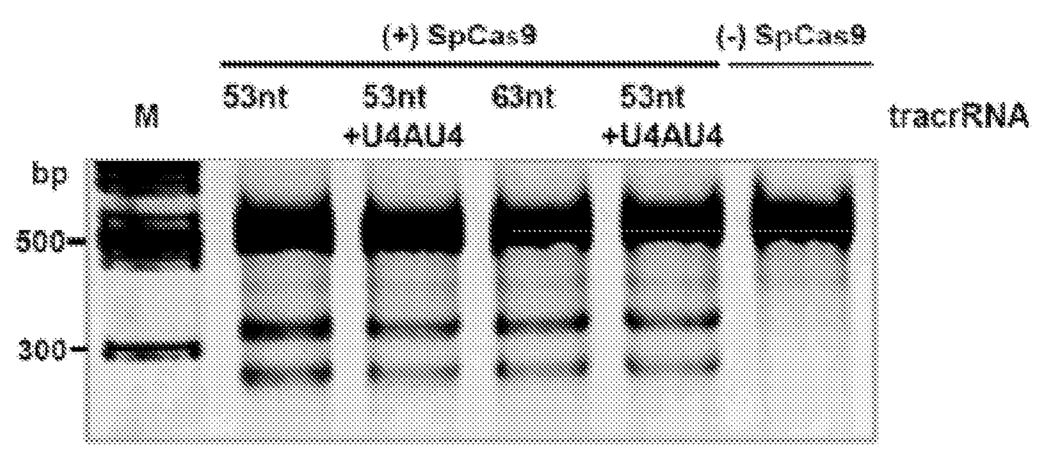

As a result, it was confirmed that the chemically modified U-rich crRNA showed much higher Cpf1 activity than the chemically modified standard crRNA. On the other hand, there was no significant difference for the chemically modified guide RNA against Cas9 (FIG. 38). In the 324th edition, Karvelis et al. reported that the minimum length of the tracrRNA for the entire SpCas9 activity was about 63 nt and shorter lengths (for example: 58 nt) exhibited relaxed activity. U-rich 3'-overhangs in short tracrRNAs will enhance SpCas9 activity if poly-uridine has affected the stability of the guide RNA in cells. However, the presence of U4AU4 in short tracrRNAs did not induce increased Cas9 activity. Rather, poly-uridine down-regulated SpCas9 activity on 63-nt tracrRNA (FIG. 39). Through these results, it was confirmed that the main reason for the improved activity due to the U-rich 3'-overhang was not due to the stability effect.

In addition, by applying two independent methodological approaches, it was analyzed whether the U-rich 3'-overhang contributes to the beneficial binding of crRNA to the cpf1 molecule.

Figure 40:
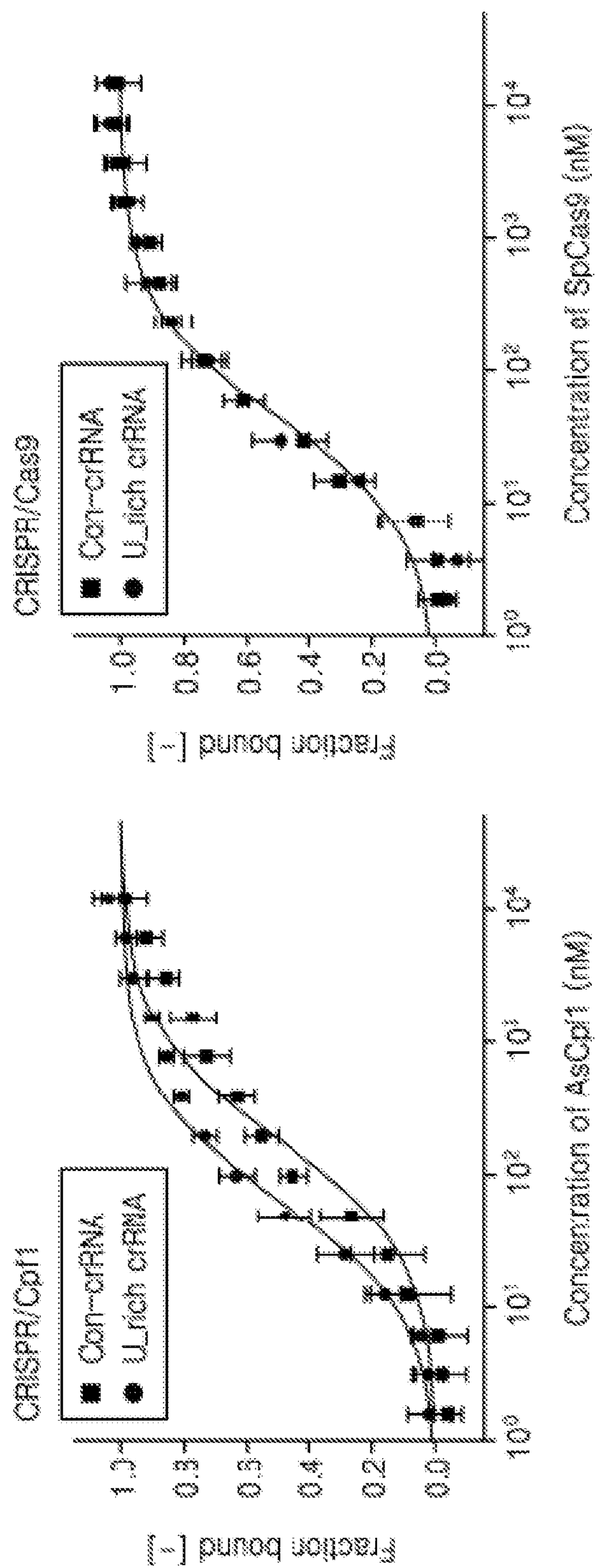

First, MST technology was applied to evaluate the binding properties of effector proteins (SpCas9 and AsCpf1) and their guide RNAs. MST is based on the directional migration of molecules with the temperature gradient, which is an effect called "thermophoresis". The heat transfer behavior of proteins typically differs from the heat transfer of protein-ligand complexes due to binding-induced changes in size, charge and solvation energy. By measuring the change in standardized fluorescence (Fnorm) of the ligand (Cy5-labeled guide RNA) titrated for the binding effector protein, the dissociation constant Kd may be derived by plotting Fnorm against the appropriate concentration. As shown below, the U-rich 3'-overhang had considerably increased binding affinity for AsCpf1 compared to the standard crRNA. However, the U-rich 3'-overhang did not induce a detectable difference in binding characteristics to the sgRNA-SpCas9 complex (FIG. 40).

Figure 41:
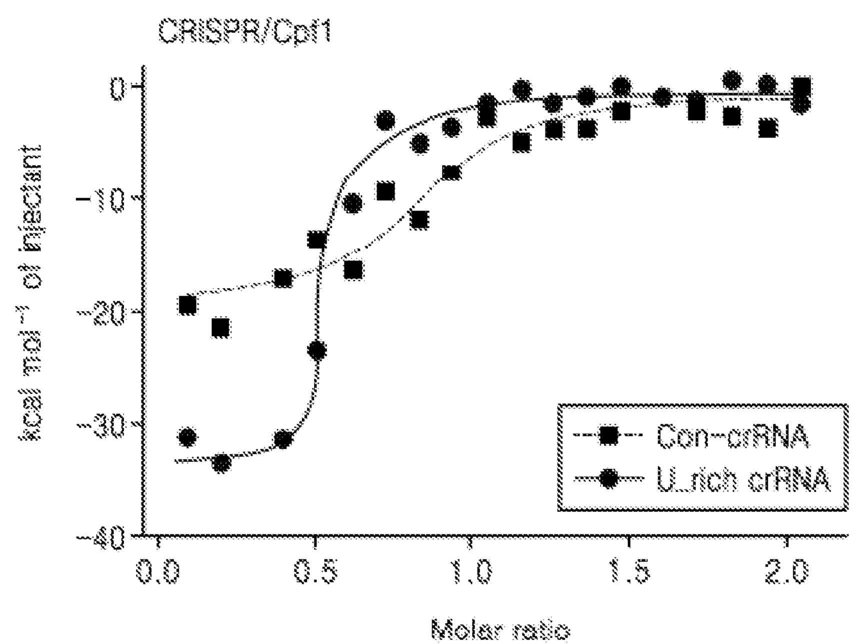

To obtain more quantitative results, ITC analysis was performed (FIG. 41), and the crRNA was titrated in the presence of AsCpf1. As a result, it was confirmed that a more rapid thermal change was observed by the U-rich crRNA and the binding constant was increased by 16.2 times [$Ka=(1.90\pm0.87)\times10^{8}$ M−1 for the U-rich crRNA versus $(1.15\pm0.54)\times10^{7}$ M−1 for the canonical crRNA]. It was confirmed that $\Delta H$ was −31.92±1.79 and −22.86±1.86 kcal $mol^{-1}$ for the U-rich crRNA and the standard crRNA, respectively, and $\Delta S$ was −69.2 and −44.4 $cal^{-1}mol^{-1}deg^{-1}$ for the U-rich crRNA and the standard crRNA, respectively.

Through these results, it was confirmed that the U-rich 3'-overhang contributed to the formation of a more stable crRNA-AsCpf1 complex, and that the U-rich 3'-overhang improved Cpf1 activity by inducing a more advantageous binding between crRNA and Cpf1.

From the foregoing, the present invention has been reviewed mainly based on the preferred examples thereof. A person with ordinary skill in the art to which the present invention pertains will be able to understand that the present invention may be implemented in a modified form without departing from the essential characteristics of the present invention. Therefore, the disclosed examples should be considered not from a restrictive viewpoint, but from an explanatory viewpoint. The scope of the present invention is defined not in the above-described explanation, but in the claims, and it should be interpreted that all the differences within a range equivalent thereto are included in the present invention.

The invention claimed is:

1. A composition for genome editing comprising:

a CRISPR RNA (crRNA) comprising a guide sequence complementary to a target nucleotide sequence and a uridine repeat sequence linked to a 3'-end of the guide sequence, or a DNA encoding the crRNA; and a Cpf1 protein or a DNA encoding the Cpf1 protein, wherein the length of guide sequence is 18 to 24 nt.

2. The composition for genome editing of claim 1, wherein the uridine repeat sequence is a nucleotide sequence represented by $(U_aV)_nU_b$, wherein a and b are an integer from 2 to 20, n is an integer from 1 to 5, and V is adenine (A), cytosine (C), or guanine (G).

3. The composition for genome editing of claim 2, wherein V is A.

4. The composition for genome editing of claim 2, wherein n is 1.

5. The composition for genome editing of claim 2, wherein $(U_aV)_nU_b$ is $U_4AU_4$.

6. The composition for genome editing of claim 1, wherein the length of guide sequence is 18 to 23 nt.

7. The composition for genome editing of claim 1, wherein the Cpf1 protein is derived from one or more microorganisms selected from the group consisting of *Candidatus* genus, *Lachnospira* genus, *Butyrivibrio* genus, *Peregrinibacteria, Acidominococcus* genus, *Porphyromonas* genus, *Prevotella* genus, *Francisella* genus, *Candidatus methanoplasma*, and *Eubacterium* genus microorganisms.

8. The composition for genome editing of claim 1, wherein the composition comprises a PCR amplicon comprising the DNA encoding the crRNA and a recombinant vector comprising the DNA encoding the Cpf1 protein.

9. The composition for genome editing of claim 1, wherein the composition comprises the DNA encoding the crRNA and the DNA encoding the Cpf1 protein.

10. The composition for genome editing of claim 9, wherein the DNA encoding the crRNA and the DNA encoding the Cpf1 protein are inserted either in one recombinant vector or separate vectors.

11. The composition for genome editing of claim 1, wherein the composition is applied for genome editing in a eukaryotic cell or a eukaryotic organism.

12. The composition for genome editing of claim 11, wherein the eukaryotic organism is a eukaryotic animal or a eukaryotic plant.

13. A method for genome editing, the method including: introduction of the composition of claim 1 into an isolated cell or organism.

14. The method of claim 13, wherein the introduction of the composition is achieved by local injection, microinjection, electroporation, or a lipofection method.

15. The method of claim 13, wherein the cell or organism is an isolated eukaryotic cell or a eukaryotic non-human organism.

16. The method of claim 15, wherein the eukaryotic cell is a cell isolated from a eukaryotic animal or a eukaryotic plant.

* * * * *

SEQUENCE LISTING

```
<160> NUMBER OF SEQ ID NOS: 478

<210> SEQ ID NO 1
<211> LENGTH: 27
<212> TYPE: DNA
<213> ORGANISM: Acidaminococcus sp.

<400> SEQUENCE: 1

tttcctgatg gtccatgtct gttactc                                          27
```

<210> SEQ ID NO 2
<211> LENGTH: 28
<212> TYPE: DNA
<213> ORGANISM: Acidaminococcus sp.

<400> SEQUENCE: 2
tttgctacac actgggcatc ggtggggg 28

<210> SEQ ID NO 3
<211> LENGTH: 27
<212> TYPE: DNA
<213> ORGANISM: Acidaminococcus sp.

<400> SEQUENCE: 3
tttctccgct ctgagcaagg cccacag 27

<210> SEQ ID NO 4
<211> LENGTH: 27
<212> TYPE: DNA
<213> ORGANISM: Acidaminococcus sp.

<400> SEQUENCE: 4
tttcgacata gtgtggtggt gccctat 27

<210> SEQ ID NO 5
<211> LENGTH: 27
<212> TYPE: DNA
<213> ORGANISM: Acidaminococcus sp.

<400> SEQUENCE: 5
tttgtgacag acagttcctg gagtgca 27

<210> SEQ ID NO 6
<211> LENGTH: 27
<212> TYPE: DNA
<213> ORGANISM: Acidaminococcus sp.

<400> SEQUENCE: 6
tttaagagca gcgattgtaa ggagagg 27

<210> SEQ ID NO 7
<211> LENGTH: 27
<212> TYPE: DNA
<213> ORGANISM: Acidaminococcus sp.

<400> SEQUENCE: 7
tttaaagaaa gctacaggaa agcaggg 27

<210> SEQ ID NO 8
<211> LENGTH: 27
<212> TYPE: DNA
<213> ORGANISM: Acidaminococcus sp.

<400> SEQUENCE: 8
tttagagaga ccgctcaggc tggaggg 27

<210> SEQ ID NO 9
<211> LENGTH: 27
<212> TYPE: DNA
<213> ORGANISM: Acidaminococcus sp.

<400> SEQUENCE: 9
tttagggaga cagggagaag tgagagg 27

<210> SEQ ID NO 10
<211> LENGTH: 27
<212> TYPE: DNA
<213> ORGANISM: Acidaminococcus sp.

<400> SEQUENCE: 10 tttaccccctg cattgccatg agccccc 27

<210> SEQ ID NO 11
<211> LENGTH: 27
<212> TYPE: DNA
<213> ORGANISM: Acidaminococcus sp.

<400> SEQUENCE: 11
ttccgggggc tcatggcaat gcagggg 27

<210> SEQ ID NO 12
<211> LENGTH: 27
<212> TYPE: DNA
<213> ORGANISM: Acidaminococcus sp.

<400> SEQUENCE: 12
tttacccgag tcctggggac agtcccc 27

<210> SEQ ID NO 13
<211> LENGTH: 27
<212> TYPE: DNA
<213> ORGANISM: Acidaminococcus sp.

<400> SEQUENCE: 13
tcccggggac tgtccccagg actcggg 27

<210> SEQ ID NO 14
<211> LENGTH: 27
<212> TYPE: DNA
<213> ORGANISM: Acidaminococcus sp.

<400> SEQUENCE: 14
ttccccgcag tgacactcgc catggcc 27

<210> SEQ ID NO 15
<211> LENGTH: 27
<212> TYPE: DNA
<213> ORGANISM: Acidaminococcus sp.

<400> SEQUENCE: 15
tttaggccat ggcgagtgtc actgcgg 27

<210> SEQ ID NO 16
<211> LENGTH: 27
<212> TYPE: DNA
<213> ORGANISM: Acidaminococcus sp.

<400> SEQUENCE: 16
tttagattca ttctcagtgc catgggg 27

<210> SEQ ID NO 17
<211> LENGTH: 27
<212> TYPE: DNA
<213> ORGANISM: Acidaminococcus sp.

<400> SEQUENCE: 17
tttaaggcaa ttgcaaccac tgaaggg 27

<210> SEQ ID NO 18
<211> LENGTH: 20
<212> TYPE: DNA
<213> ORGANISM: Acidaminococcus sp.

<400> SEQUENCE: 18
ctgggactca ggcgggtcac 20

<210> SEQ ID NO 19
<211> LENGTH: 25
<212> TYPE: DNA
<213> ORGANISM: Acidaminococcus sp.

<400> SEQUENCE: 19
cctcacacaa cagcttcatg tcagc 25

<210> SEQ ID NO 20
<211> LENGTH: 20
<212> TYPE: DNA
<213> ORGANISM: Acidaminococcus sp.

<400> SEQUENCE: 20
aagcaaatcc acctgcctcg 20

<210> SEQ ID NO 21
<211> LENGTH: 20
<212> TYPE: DNA
<213> ORGANISM: Acidaminococcus sp.

<400> SEQUENCE: 21
cctcccctag ccctttcagg 20

<210> SEQ ID NO 22
<211> LENGTH: 20
<212> TYPE: DNA
<213> ORGANISM: Acidaminococcus sp.

<400> SEQUENCE: 22
ctagccagtg ctgcctcttt 20

<210> SEQ ID NO 23
<211> LENGTH: 20
<212> TYPE: DNA
<213> ORGANISM: Acidaminococcus sp.

<400> SEQUENCE: 23
cgctcgctca ctctctttct 20

<210> SEQ ID NO 24
<211> LENGTH: 20
<212> TYPE: DNA
<213> ORGANISM: Acidaminococcus sp.

<400> SEQUENCE: 24
cagatagcga tggtgagcag 20

<210> SEQ ID NO 25
<211> LENGTH: 22
<212> TYPE: DNA
<213> ORGANISM: Acidaminococcus sp.

<400> SEQUENCE: 25
gggaggtcaa ataagcagca gg 22

<210> SEQ ID NO 26
<211> LENGTH: 20
<212> TYPE: DNA
<213> ORGANISM: Acidaminococcus sp.

<400> SEQUENCE: 26
actgaaggcc gtggacacct 20

<210> SEQ ID NO 27
<211> LENGTH: 20
<212> TYPE: DNA
<213> ORGANISM: Acidaminococcus sp.

<400> SEQUENCE: 27
cttgtcctgg aagaggaagc 20

<210> SEQ ID NO 28
<211> LENGTH: 20
<212> TYPE: DNA
<213> ORGANISM: Acidaminococcus sp.

<400> SEQUENCE: 28
acagggccat cttgtgacag 20

<210> SEQ ID NO 29
<211> LENGTH: 20
<212> TYPE: DNA
<213> ORGANISM: Acidaminococcus sp.

<400> SEQUENCE: 29
ccgctaaagt gcgaatcacg 20

<210> SEQ ID NO 30
<211> LENGTH: 20
<212> TYPE: DNA
<213> ORGANISM: Acidaminococcus sp.

<400> SEQUENCE: 30
gccagcccct gattcttcag 20

<210> SEQ ID NO 31
<211> LENGTH: 22
<212> TYPE: DNA
<213> ORGANISM: Acidaminococcus sp.

<400> SEQUENCE: 31
agtgaattat gttggcttgg ca 22

<210> SEQ ID NO 32
<211> LENGTH: 20
<212> TYPE: DNA
<213> ORGANISM: Acidaminococcus sp.

<400> SEQUENCE: 32
aagccgaaag cctacacctc 20

<210> SEQ ID NO 33
<211> LENGTH: 20
<212> TYPE: DNA
<213> ORGANISM: Acidaminococcus sp.

<400> SEQUENCE: 33
ggacattcga agcccgtgta 20

<210> SEQ ID NO 34
<211> LENGTH: 20
<212> TYPE: DNA
<213> ORGANISM: Acidaminococcus sp.

<400> SEQUENCE: 34
aagccgaaag cctacacctc 20

<210> SEQ ID NO 35
<211> LENGTH: 20
<212> TYPE: DNA
<213> ORGANISM: Acidaminococcus sp.

<400> SEQUENCE: 35
ggacattcga agcccgtgta 20

<210> SEQ ID NO 36
<211> LENGTH: 20
<212> TYPE: DNA
<213> ORGANISM: Acidaminococcus sp.

<400> SEQUENCE: 36
ctttcaacaa agcagccccc 20

<210> SEQ ID NO 37
<211> LENGTH: 20
<212> TYPE: DNA
<213> ORGANISM: Acidaminococcus sp.

<400> SEQUENCE: 37
tgctctggtc tcagcattcg 20

<210> SEQ ID NO 38
<211> LENGTH: 20
<212> TYPE: DNA
<213> ORGANISM: Acidaminococcus sp.

<400> SEQUENCE: 38
ctttcaacaa agcagccccc 20

<210> SEQ ID NO 39
<211> LENGTH: 20
<212> TYPE: DNA
<213> ORGANISM: Acidaminococcus sp.

<400> SEQUENCE: 39
tgctctggtc tcagcattcg 20

<210> SEQ ID NO 40
<211> LENGTH: 20
<212> TYPE: DNA
<213> ORGANISM: Acidaminococcus sp.

<400> SEQUENCE: 40
tgagattggg tctgttgggc 20

<210> SEQ ID NO 41
<211> LENGTH: 20
<212> TYPE: DNA
<213> ORGANISM: Acidaminococcus sp.

<400> SEQUENCE: 41
tgagattggg tctgttgggc 20

<210> SEQ ID NO 42
<211> LENGTH: 20
<212> TYPE: DNA
<213> ORGANISM: Acidaminococcus sp.

<400> SEQUENCE: 42
tgagattggg tctgttgggc 20

<210> SEQ ID NO 43
<211> LENGTH: 20
<212> TYPE: DNA
<213> ORGANISM: Acidaminococcus sp.

<400> SEQUENCE: 43
tgagattggg tctgttgggc 20

<210> SEQ ID NO 44
<211> LENGTH: 20
<212> TYPE: DNA
<213> ORGANISM: Acidaminococcus sp.

<400> SEQUENCE: 44
ttggtaagaa tgcggctccc 20

<210> SEQ ID NO 45
<211> LENGTH: 20
<212> TYPE: DNA
<213> ORGANISM: Acidaminococcus sp.

<400> SEQUENCE: 45
cataaccatc tggtgcccca 20

<210> SEQ ID NO 46
<211> LENGTH: 20
<212> TYPE: DNA
<213> ORGANISM: Acidaminococcus sp.

<400> SEQUENCE: 46
ttggtaagaa tgcggctccc 20

<210> SEQ ID NO 47
<211> LENGTH: 20
<212> TYPE: DNA
<213> ORGANISM: Acidaminococcus sp.

<400> SEQUENCE: 47
cataaccatc tggtgcccca 20

<210> SEQ ID NO 48
<211> LENGTH: 21
<212> TYPE: DNA
<213> ORGANISM: Acidaminococcus sp.

<400> SEQUENCE: 48
gtggccaggg tggaggataa g 21

<210> SEQ ID NO 49
<211> LENGTH: 23
<212> TYPE: DNA

<213> ORGANISM: Acidaminococcus sp.

<400> SEQUENCE: 49
ctctggctcc tttgatacct ccg 23

<210> SEQ ID NO 50
<211> LENGTH: 21
<212> TYPE: DNA
<213> ORGANISM: Acidaminococcus sp.

<400> SEQUENCE: 50
gtggccaggg tggaggataa g 21

<210> SEQ ID NO 51
<211> LENGTH: 23
<212> TYPE: DNA
<213> ORGANISM: Acidaminococcus sp.

<400> SEQUENCE: 51
ctctggctcc tttgatacct ccg 23

<210> SEQ ID NO 52
<211> LENGTH: 23
<212> TYPE: DNA
<213> ORGANISM: Acidaminococcus sp.

<400> SEQUENCE: 52
tacactggcc agaggctggg acg 23

<210> SEQ ID NO 53
<211> LENGTH: 23
<212> TYPE: DNA
<213> ORGANISM: Acidaminococcus sp.

<400> SEQUENCE: 53
cgtcccagcc tctggccagt gta 23

<210> SEQ ID NO 54
<211> LENGTH: 23
<212> TYPE: DNA
<213> ORGANISM: Acidaminococcus sp.

<400> SEQUENCE: 54
gatgatccca aggtgcagca ccc 23

<210> SEQ ID NO 55
<211> LENGTH: 23
<212> TYPE: DNA
<213> ORGANISM: Acidaminococcus sp.

<400> SEQUENCE: 55
gggtgctgca ccttgggatc atc 23

<210> SEQ ID NO 56
<211> LENGTH: 30
<212> TYPE: DNA
<213> ORGANISM: Acidaminococcus sp.

<400> SEQUENCE: 56
gtggagaaga acagaggcgc catcctgttt 30

<210> SEQ ID NO 57
<211> LENGTH: 30

<212> TYPE: DNA
<213> ORGANISM: Acidaminococcus sp.

<400> SEQUENCE: 57
tctgttcttc tccacattca cgtcccagcc 30

<210> SEQ ID NO 58
<211> LENGTH: 23
<212> TYPE: DNA
<213> ORGANISM: Acidaminococcus sp.

<400> SEQUENCE: 58
ctgatggtcc atgtctgtta ctc 23

<210> SEQ ID NO 59
<211> LENGTH: 24
<212> TYPE: DNA
<213> ORGANISM: Acidaminococcus sp.

<400> SEQUENCE: 59
tttctttcct gtttgtcttg tgtc 24

<210> SEQ ID NO 60
<211> LENGTH: 25
<212> TYPE: DNA
<213> ORGANISM: Acidaminococcus sp.

<400> SEQUENCE: 60
tttgttttct gtttgtcttg tagtc 25

<210> SEQ ID NO 61
<211> LENGTH: 21
<212> TYPE: DNA
<213> ORGANISM: Acidaminococcus sp.

<400> SEQUENCE: 61
tttgtttcct gtttgtcttg t 21

<210> SEQ ID NO 62
<211> LENGTH: 22
<212> TYPE: DNA
<213> ORGANISM: Acidaminococcus sp.

<400> SEQUENCE: 62
tttctttcct gtttcttttg tc 22

<210> SEQ ID NO 63
<211> LENGTH: 26
<212> TYPE: DNA
<213> ORGANISM: Acidaminococcus sp.

<400> SEQUENCE: 63
tttctttcct gtttgtcttg catctc 26

<210> SEQ ID NO 64
<211> LENGTH: 24
<212> TYPE: DNA
<213> ORGANISM: Acidaminococcus sp.

<400> SEQUENCE: 64
tttgtttcct gtttgttttg tgtt 24

<210> SEQ ID NO 65

<211> LENGTH: 23
<212> TYPE: DNA
<213> ORGANISM: Acidaminococcus sp.

<400> SEQUENCE: 65
tttatttctt gtttgtcttg gta 23

<210> SEQ ID NO 66
<211> LENGTH: 25
<212> TYPE: DNA
<213> ORGANISM: Acidaminococcus sp.

<400> SEQUENCE: 66
tttgttttct ggttgtcttg ttgtc 25

<210> SEQ ID NO 67
<211> LENGTH: 22
<212> TYPE: DNA
<213> ORGANISM: Acidaminococcus sp.

<400> SEQUENCE: 67
tttgttttgt ttgtcttgtt tt 22

<210> SEQ ID NO 68
<211> LENGTH: 22
<212> TYPE: DNA
<213> ORGANISM: Acidaminococcus sp.

<400> SEQUENCE: 68
tttgtttcct gtttctcttt tc 22

<210> SEQ ID NO 69
<211> LENGTH: 42
<212> TYPE: DNA
<213> ORGANISM: Acidaminococcus sp.

<400> SEQUENCE: 69
aatttctact cttgtagatc tgatggtcca tgtctgttac tc 42

<210> SEQ ID NO 70
<211> LENGTH: 50
<212> TYPE: DNA
<213> ORGANISM: Acidaminococcus sp.

<400> SEQUENCE: 70
aatttctact cttgtagatc tgatggtcca tgtctgttat tttatttttt 50

<210> SEQ ID NO 71
<211> LENGTH: 23
<212> TYPE: DNA
<213> ORGANISM: Acidaminococcus sp.

<400> SEQUENCE: 71
cctggtggct gagaccaggg agg 23

<210> SEQ ID NO 72
<211> LENGTH: 23
<212> TYPE: DNA
<213> ORGANISM: Acidaminococcus sp.

<400> SEQUENCE: 72
atttcacagg actttgttaa agg 23

<210> SEQ ID NO 73
<211> LENGTH: 23
<212> TYPE: DNA
<213> ORGANISM: Acidaminococcus sp.

<400> SEQUENCE: 73
attttgaagt gaccgtacga ggg 23

<210> SEQ ID NO 74
<211> LENGTH: 23
<212> TYPE: DNA
<213> ORGANISM: Acidaminococcus sp.

<400> SEQUENCE: 74
ataatacact ctttacactg agg 23

<210> SEQ ID NO 75
<211> LENGTH: 23
<212> TYPE: DNA
<213> ORGANISM: Acidaminococcus sp.

<400> SEQUENCE: 75
aacaaatcac tgactaacca agg 23

<210> SEQ ID NO 76
<211> LENGTH: 23
<212> TYPE: DNA
<213> ORGANISM: Acidaminococcus sp.

<400> SEQUENCE: 76
gtgtggataa gaatcacctg agg 23

<210> SEQ ID NO 77
<211> LENGTH: 23
<212> TYPE: DNA
<213> ORGANISM: Acidaminococcus sp.

<400> SEQUENCE: 77
ggggtagagg tactctacag ggg 23

<210> SEQ ID NO 78
<211> LENGTH: 23
<212> TYPE: DNA
<213> ORGANISM: Acidaminococcus sp.

<400> SEQUENCE: 78
ggggtagagg tagtctacag ggg 23

<210> SEQ ID NO 79
<211> LENGTH: 23
<212> TYPE: DNA
<213> ORGANISM: Acidaminococcus sp.

<400> SEQUENCE: 79
gcattaaggc cagcgctggg cgg 23

<210> SEQ ID NO 80
<211> LENGTH: 23
<212> TYPE: DNA
<213> ORGANISM: Acidaminococcus sp.

<400> SEQUENCE: 80
cacataggcc attcagaaac ggg 23

<210> SEQ ID NO 81
<211> LENGTH: 23
<212> TYPE: DNA
<213> ORGANISM: Acidaminococcus sp.

<400> SEQUENCE: 81
attttagcaa taaccttaca ggg 23

<210> SEQ ID NO 82
<211> LENGTH: 23
<212> TYPE: DNA
<213> ORGANISM: Acidaminococcus sp.

<400> SEQUENCE: 82
cgtgttcaaa aaccaaggcg ggg 23

<210> SEQ ID NO 83
<211> LENGTH: 23
<212> TYPE: DNA
<213> ORGANISM: Acidaminococcus sp.

<400> SEQUENCE: 83
acaagttcag aatcacctta ggg 23

<210> SEQ ID NO 84
<211> LENGTH: 23
<212> TYPE: DNA
<213> ORGANISM: Acidaminococcus sp.

<400> SEQUENCE: 84
aaataaccgt cggtttctta agg 23

<210> SEQ ID NO 85
<211> LENGTH: 23
<212> TYPE: DNA
<213> ORGANISM: Acidaminococcus sp.

<400> SEQUENCE: 85
gatccgatgc aattttggga agg 23

<210> SEQ ID NO 86
<211> LENGTH: 23
<212> TYPE: DNA
<213> ORGANISM: Acidaminococcus sp.

<400> SEQUENCE: 86
ggaaagcgca gaaaagtaaa agg 23

<210> SEQ ID NO 87
<211> LENGTH: 23
<212> TYPE: DNA
<213> ORGANISM: Acidaminococcus sp.

<400> SEQUENCE: 87
aagagttatt gtcaatagaa agg 23

<210> SEQ ID NO 88
<211> LENGTH: 23
<212> TYPE: DNA
<213> ORGANISM: Acidaminococcus sp.

<400> SEQUENCE: 88
caaagaaatg tactgcctta cgg 23

<210> SEQ ID NO 89
<211> LENGTH: 23
<212> TYPE: DNA
<213> ORGANISM: Acidaminococcus sp.

<400> SEQUENCE: 89
cctctgactt gacttcaaac agg 23

<210> SEQ ID NO 90
<211> LENGTH: 23
<212> TYPE: DNA
<213> ORGANISM: Acidaminococcus sp.

<400> SEQUENCE: 90
gtgggtaggt ccagtttggg ggg 23

<210> SEQ ID NO 91
<211> LENGTH: 23
<212> TYPE: DNA
<213> ORGANISM: Acidaminococcus sp.

<400> SEQUENCE: 91
acaaagaaac cagcagtggc agg 23

<210> SEQ ID NO 92
<211> LENGTH: 23
<212> TYPE: DNA
<213> ORGANISM: Acidaminococcus sp.

<400> SEQUENCE: 92
cctgaactcg ggactcgacc agg 23

<210> SEQ ID NO 93
<211> LENGTH: 22
<212> TYPE: DNA
<213> ORGANISM: Acidaminococcus sp.

<400> SEQUENCE: 93
ccaaccaggt accctgtgcc ag 22

<210> SEQ ID NO 94
<211> LENGTH: 23
<212> TYPE: DNA
<213> ORGANISM: Acidaminococcus sp.

<400> SEQUENCE: 94
actggttatt tcttgccaga ggg 23

<210> SEQ ID NO 95
<211> LENGTH: 23
<212> TYPE: DNA
<213> ORGANISM: Acidaminococcus sp.

<400> SEQUENCE: 95
gaacccagtg aaaaatacca ggg 23

<210> SEQ ID NO 96
<211> LENGTH: 23
<212> TYPE: DNA
<213> ORGANISM: Acidaminococcus sp.

<400> SEQUENCE: 96
ccctggctac ctcccctacc cgg 23

<210> SEQ ID NO 97
<211> LENGTH: 23
<212> TYPE: DNA
<213> ORGANISM: Acidaminococcus sp.

<400> SEQUENCE: 97
gaggtagctt gccatctctc agg 23

<210> SEQ ID NO 98
<211> LENGTH: 23
<212> TYPE: DNA
<213> ORGANISM: Acidaminococcus sp.

<400> SEQUENCE: 98
ctattcactt gtgttacagg agg 23

<210> SEQ ID NO 99
<211> LENGTH: 23
<212> TYPE: DNA
<213> ORGANISM: Acidaminococcus sp.

<400> SEQUENCE: 99
gtaggctgct gttggacaga cgg 23

<210> SEQ ID NO 100
<211> LENGTH: 23
<212> TYPE: DNA
<213> ORGANISM: Acidaminococcus sp.

<400> SEQUENCE: 100
ggcaagggtc ttgatgcatc agg 23

<210> SEQ ID NO 101
<211> LENGTH: 23
<212> TYPE: DNA
<213> ORGANISM: Acidaminococcus sp.

<400> SEQUENCE: 101
ccgaaaaaat gactttttag ggg 23

<210> SEQ ID NO 102
<211> LENGTH: 23
<212> TYPE: DNA
<213> ORGANISM: Acidaminococcus sp.

<400> SEQUENCE: 102
actcaagttg ttcattctgc ggg 23

<210> SEQ ID NO 103
<211> LENGTH: 23
<212> TYPE: DNA
<213> ORGANISM: Acidaminococcus sp.

<400> SEQUENCE: 103
gccatggtga aggtgaaatc agg 23

<210> SEQ ID NO 104
<211> LENGTH: 23
<212> TYPE: DNA
<213> ORGANISM: Acidaminococcus sp.

<400> SEQUENCE: 104
ctgaattaca acaaattgca agg 23

<210> SEQ ID NO 105
<211> LENGTH: 23
<212> TYPE: DNA
<213> ORGANISM: Acidaminococcus sp.

<400> SEQUENCE: 105
aagaaggaat ggtagttgag ggg 23

<210> SEQ ID NO 106
<211> LENGTH: 23
<212> TYPE: DNA
<213> ORGANISM: Acidaminococcus sp.

<400> SEQUENCE: 106
agcccaagat tttttatttg agg 23

<210> SEQ ID NO 107
<211> LENGTH: 23
<212> TYPE: DNA
<213> ORGANISM: Acidaminococcus sp.

<400> SEQUENCE: 107
atataggatt tagaaaccaa ggg 23

<210> SEQ ID NO 108
<211> LENGTH: 23
<212> TYPE: DNA
<213> ORGANISM: Acidaminococcus sp.

<400> SEQUENCE: 108
acatttttag ctggccactg cgg 23

<210> SEQ ID NO 109
<211> LENGTH: 23
<212> TYPE: DNA
<213> ORGANISM: Acidaminococcus sp.

<400> SEQUENCE: 109
gaataccccc attcttcagg ggg 23

<210> SEQ ID NO 110
<211> LENGTH: 23
<212> TYPE: DNA
<213> ORGANISM: Acidaminococcus sp.

<400> SEQUENCE: 110
agagcagcga ttgtaaggag agg 23

<210> SEQ ID NO 111
<211> LENGTH: 23
<212> TYPE: DNA
<213> ORGANISM: Acidaminococcus sp.

<400> SEQUENCE: 111
aaaagatccc catggccaca ggg 23

<210> SEQ ID NO 112
<211> LENGTH: 23
<212> TYPE: DNA
<213> ORGANISM: Acidaminococcus sp.

<400> SEQUENCE: 112
aacgaatatt ctcagaccac agg 23

<210> SEQ ID NO 113
<211> LENGTH: 23
<212> TYPE: DNA
<213> ORGANISM: Acidaminococcus sp.

<400> SEQUENCE: 113
gggaggagaa caggaaataa ggg 23

<210> SEQ ID NO 114
<211> LENGTH: 23
<212> TYPE: DNA
<213> ORGANISM: Acidaminococcus sp.

<400> SEQUENCE: 114
attgaaacat atacgtggta agg 23

<210> SEQ ID NO 115
<211> LENGTH: 23
<212> TYPE: DNA
<213> ORGANISM: Acidaminococcus sp.

<400> SEQUENCE: 115
gtctaataga aatatagtac agg 23

<210> SEQ ID NO 116
<211> LENGTH: 23
<212> TYPE: DNA
<213> ORGANISM: Acidaminococcus sp.

<400> SEQUENCE: 116
gctctaatgt aagtatatcc agg 23

<210> SEQ ID NO 117
<211> LENGTH: 23
<212> TYPE: DNA
<213> ORGANISM: Acidaminococcus sp.

<400> SEQUENCE: 117
caacagcctc accaggaaca agg 23

<210> SEQ ID NO 118
<211> LENGTH: 23
<212> TYPE: DNA
<213> ORGANISM: Acidaminococcus sp.

<400> SEQUENCE: 118
aaaagatccc catggccaca ggg 23

<210> SEQ ID NO 119
<211> LENGTH: 23
<212> TYPE: DNA
<213> ORGANISM: Acidaminococcus sp.

<400> SEQUENCE: 119
gggttgccag attaaaagac agg 23

<210> SEQ ID NO 120
<211> LENGTH: 23
<212> TYPE: DNA
<213> ORGANISM: Acidaminococcus sp.

<400> SEQUENCE: 120
gagggagaca caagttgata ggg 23

<210> SEQ ID NO 121
<211> LENGTH: 23
<212> TYPE: DNA
<213> ORGANISM: Acidaminococcus sp.

<400> SEQUENCE: 121
actcatacat cacctcctcc agg 23

<210> SEQ ID NO 122
<211> LENGTH: 23
<212> TYPE: DNA
<213> ORGANISM: Acidaminococcus sp.

<400> SEQUENCE: 122
ccttaataaa gtataacttc agg 23

<210> SEQ ID NO 123
<211> LENGTH: 23
<212> TYPE: DNA
<213> ORGANISM: Acidaminococcus sp.

<400> SEQUENCE: 123
gaaactgccc caaaaccggc cgg 23

<210> SEQ ID NO 124
<211> LENGTH: 23
<212> TYPE: DNA
<213> ORGANISM: Acidaminococcus sp.

<400> SEQUENCE: 124
aggactatgt gtggccagtg agg 23

<210> SEQ ID NO 125
<211> LENGTH: 23
<212> TYPE: DNA
<213> ORGANISM: Acidaminococcus sp.

<400> SEQUENCE: 125
attttcaaaa cagccctatg ggg 23

<210> SEQ ID NO 126
<211> LENGTH: 23
<212> TYPE: DNA
<213> ORGANISM: Acidaminococcus sp.

<400> SEQUENCE: 126
cacaagggat ctgagacttg agg 23

<210> SEQ ID NO 127
<211> LENGTH: 23
<212> TYPE: DNA
<213> ORGANISM: Acidaminococcus sp.

<400> SEQUENCE: 127
actcaaggac tggctcagtg agg 23

<210> SEQ ID NO 128
<211> LENGTH: 23
<212> TYPE: DNA

<213> ORGANISM: Acidaminococcus sp.

<400> SEQUENCE: 128
cagagtcccg ggaacaagcc agg 23

<210> SEQ ID NO 129
<211> LENGTH: 23
<212> TYPE: DNA
<213> ORGANISM: Acidaminococcus sp.

<400> SEQUENCE: 129
tttacagctc tgagaactaa acg 23

<210> SEQ ID NO 130
<211> LENGTH: 23
<212> TYPE: DNA
<213> ORGANISM: Acidaminococcus sp.

<400> SEQUENCE: 130
agacaagctg tcttccttca ggg 23

<210> SEQ ID NO 131
<211> LENGTH: 23
<212> TYPE: DNA
<213> ORGANISM: Acidaminococcus sp.

<400> SEQUENCE: 131
atctgaagat cattgaaaca ggg 23

<210> SEQ ID NO 132
<211> LENGTH: 23
<212> TYPE: DNA
<213> ORGANISM: Acidaminococcus sp.

<400> SEQUENCE: 132
aaggaaaggc ttcctggagg agg 23

<210> SEQ ID NO 133
<211> LENGTH: 23
<212> TYPE: DNA
<213> ORGANISM: Acidaminococcus sp.

<400> SEQUENCE: 133
gtctcagtct tccttgtggg agg 23

<210> SEQ ID NO 134
<211> LENGTH: 23
<212> TYPE: DNA
<213> ORGANISM: Acidaminococcus sp.

<400> SEQUENCE: 134
agataagcga tagtacatga ggg 23

<210> SEQ ID NO 135
<211> LENGTH: 23
<212> TYPE: DNA
<213> ORGANISM: Acidaminococcus sp.

<400> SEQUENCE: 135
gcagtacacc tgagggaaca ggg 23

<210> SEQ ID NO 136
<211> LENGTH: 23

<212> TYPE: DNA
<213> ORGANISM: Acidaminococcus sp.

<400> SEQUENCE: 136
aagaaagcta caggaaagca ggg 23

<210> SEQ ID NO 137
<211> LENGTH: 23
<212> TYPE: DNA
<213> ORGANISM: Acidaminococcus sp.

<400> SEQUENCE: 137
atttccaagt caaccttatg agg 23

<210> SEQ ID NO 138
<211> LENGTH: 23
<212> TYPE: DNA
<213> ORGANISM: Acidaminococcus sp.

<400> SEQUENCE: 138
caaagtacct gttacttaac agg 23

<210> SEQ ID NO 139
<211> LENGTH: 23
<212> TYPE: DNA
<213> ORGANISM: Acidaminococcus sp.

<400> SEQUENCE: 139
aataagtctt accacgtgtc agg 23

<210> SEQ ID NO 140
<211> LENGTH: 23
<212> TYPE: DNA
<213> ORGANISM: Acidaminococcus sp.

<400> SEQUENCE: 140
attcccacaa taaccctatg agg 23

<210> SEQ ID NO 141
<211> LENGTH: 23
<212> TYPE: DNA
<213> ORGANISM: Acidaminococcus sp.

<400> SEQUENCE: 141
ataatgcctt ttaggtgata agg 23

<210> SEQ ID NO 142
<211> LENGTH: 23
<212> TYPE: DNA
<213> ORGANISM: Acidaminococcus sp.

<400> SEQUENCE: 142
gagaatagaa ataagaaaaa agg 23

<210> SEQ ID NO 143
<211> LENGTH: 23
<212> TYPE: DNA
<213> ORGANISM: Acidaminococcus sp.

<400> SEQUENCE: 143
caaacaaaat aattggctca ggg 23

<210> SEQ ID NO 144

<211> LENGTH: 23
<212> TYPE: DNA
<213> ORGANISM: Acidaminococcus sp.

<400> SEQUENCE: 144
caatcatagc agaaggtgaa ggg 23

<210> SEQ ID NO 145
<211> LENGTH: 23
<212> TYPE: DNA
<213> ORGANISM: Acidaminococcus sp.

<400> SEQUENCE: 145
ctttaaaatg aggtactagg ggg 23

<210> SEQ ID NO 146
<211> LENGTH: 23
<212> TYPE: DNA
<213> ORGANISM: Acidaminococcus sp.

<400> SEQUENCE: 146
agggaatgaa agtgaagatg ggg 23

<210> SEQ ID NO 147
<211> LENGTH: 23
<212> TYPE: DNA
<213> ORGANISM: Acidaminococcus sp.

<400> SEQUENCE: 147
gagagaccgc tcaggctgga ggg 23

<210> SEQ ID NO 148
<211> LENGTH: 23
<212> TYPE: DNA
<213> ORGANISM: Acidaminococcus sp.

<400> SEQUENCE: 148
gatcaattta catcaaacta ggg 23

<210> SEQ ID NO 149
<211> LENGTH: 23
<212> TYPE: DNA
<213> ORGANISM: Acidaminococcus sp.

<400> SEQUENCE: 149
atccccacaa atactctacg agg 23

<210> SEQ ID NO 150
<211> LENGTH: 23
<212> TYPE: DNA
<213> ORGANISM: Acidaminococcus sp.

<400> SEQUENCE: 150
gattcattct cagtgccatg ggg 23

<210> SEQ ID NO 151
<211> LENGTH: 23
<212> TYPE: DNA
<213> ORGANISM: Acidaminococcus sp.

<400> SEQUENCE: 151
aggcaattgc aaccactgaa ggg 23

<210> SEQ ID NO 152
<211> LENGTH: 23
<212> TYPE: DNA
<213> ORGANISM: Acidaminococcus sp.

<400> SEQUENCE: 152
gaaatatgac tggaagtaaa ggg 23

<210> SEQ ID NO 153
<211> LENGTH: 23
<212> TYPE: DNA
<213> ORGANISM: Acidaminococcus sp.

<400> SEQUENCE: 153
cttccagtca tatttctaaa ggg 23

<210> SEQ ID NO 154
<211> LENGTH: 23
<212> TYPE: DNA
<213> ORGANISM: Acidaminococcus sp.

<400> SEQUENCE: 154
cccttattac aatcctgtgg ggg 23

<210> SEQ ID NO 155
<211> LENGTH: 23
<212> TYPE: DNA
<213> ORGANISM: Acidaminococcus sp.

<400> SEQUENCE: 155
cccccacagg attgtaataa ggg 23

<210> SEQ ID NO 156
<211> LENGTH: 23
<212> TYPE: DNA
<213> ORGANISM: Acidaminococcus sp.

<400> SEQUENCE: 156
atctccataa caatctttgg ggg 23

<210> SEQ ID NO 157
<211> LENGTH: 23
<212> TYPE: DNA
<213> ORGANISM: Acidaminococcus sp.

<400> SEQUENCE: 157
ctatccccat tttacagatg agg 23

<210> SEQ ID NO 158
<211> LENGTH: 23
<212> TYPE: DNA
<213> ORGANISM: Acidaminococcus sp.

<400> SEQUENCE: 158
ctgagatttg cgaagagtta ggg 23

<210> SEQ ID NO 159
<211> LENGTH: 23
<212> TYPE: DNA
<213> ORGANISM: Acidaminococcus sp.

<400> SEQUENCE: 159
attaaataga gtcttttgaa ggg 23

<210> SEQ ID NO 160
<211> LENGTH: 23
<212> TYPE: DNA
<213> ORGANISM: Acidaminococcus sp.

<400> SEQUENCE: 160
atattaattg caagtttggg ggg 23

<210> SEQ ID NO 161
<211> LENGTH: 23
<212> TYPE: DNA
<213> ORGANISM: Acidaminococcus sp.

<400> SEQUENCE: 161
ggccaagtgc gaagtcagag ggg 23

<210> SEQ ID NO 162
<211> LENGTH: 23
<212> TYPE: DNA
<213> ORGANISM: Acidaminococcus sp.

<400> SEQUENCE: 162
ggggtgaaca cccaagatcc cgg 23

<210> SEQ ID NO 163
<211> LENGTH: 23
<212> TYPE: DNA
<213> ORGANISM: Acidaminococcus sp.

<400> SEQUENCE: 163
gggtgggctc ctggcagggc agg 23

<210> SEQ ID NO 164
<211> LENGTH: 23
<212> TYPE: DNA
<213> ORGANISM: Acidaminococcus sp.

<400> SEQUENCE: 164
aaaaggggaa agagagaaag agg 23

<210> SEQ ID NO 165
<211> LENGTH: 23
<212> TYPE: DNA
<213> ORGANISM: Acidaminococcus sp.

<400> SEQUENCE: 165
agaagcatgc aaaaccggca agg 23

<210> SEQ ID NO 166
<211> LENGTH: 23
<212> TYPE: DNA
<213> ORGANISM: Acidaminococcus sp.

<400> SEQUENCE: 166
aagaggggag gttgactttg ggg 23

<210> SEQ ID NO 167
<211> LENGTH: 23
<212> TYPE: DNA
<213> ORGANISM: Acidaminococcus sp.

<400> SEQUENCE: 167
gtcaaataaa gaaatacacg ggg 23

<210> SEQ ID NO 168
<211> LENGTH: 23
<212> TYPE: DNA
<213> ORGANISM: Acidaminococcus sp.

<400> SEQUENCE: 168
gtcaaataaa gaaaaatacg ggg 23

<210> SEQ ID NO 169
<211> LENGTH: 23
<212> TYPE: DNA
<213> ORGANISM: Acidaminococcus sp.

<400> SEQUENCE: 169
atgcatctca gtggttaaca ggg 23

<210> SEQ ID NO 170
<211> LENGTH: 23
<212> TYPE: DNA
<213> ORGANISM: Acidaminococcus sp.

<400> SEQUENCE: 170
acctcaggcc tgatcatcag ggg 23

<210> SEQ ID NO 171
<211> LENGTH: 23
<212> TYPE: DNA
<213> ORGANISM: Acidaminococcus sp.

<400> SEQUENCE: 171
catacagggc tctgtaccca ggg 23

<210> SEQ ID NO 172
<211> LENGTH: 23
<212> TYPE: DNA
<213> ORGANISM: Acidaminococcus sp.

<400> SEQUENCE: 172
caaagacact caccctgttg ggg 23

<210> SEQ ID NO 173
<211> LENGTH: 23
<212> TYPE: DNA
<213> ORGANISM: Acidaminococcus sp.

<400> SEQUENCE: 173
agaacacata cccctgggcc ggg 23

<210> SEQ ID NO 174
<211> LENGTH: 23
<212> TYPE: DNA
<213> ORGANISM: Acidaminococcus sp.

<400> SEQUENCE: 174
ataataaaag tatttcctca ggg 23

<210> SEQ ID NO 175
<211> LENGTH: 23
<212> TYPE: DNA
<213> ORGANISM: Acidaminococcus sp.

<400> SEQUENCE: 175
agccgtggtc agtgagaggc agg 23

<210> SEQ ID NO 176
<211> LENGTH: 23
<212> TYPE: DNA
<213> ORGANISM: Acidaminococcus sp.

<400> SEQUENCE: 176
gagctcatta gcttggggag ggg 23

<210> SEQ ID NO 177
<211> LENGTH: 23
<212> TYPE: DNA
<213> ORGANISM: Acidaminococcus sp.

<400> SEQUENCE: 177
ggaaaagtca tctgctacta ggg 23

<210> SEQ ID NO 178
<211> LENGTH: 23
<212> TYPE: DNA
<213> ORGANISM: Acidaminococcus sp.

<400> SEQUENCE: 178
gaaaataact aaacttccca ggg 23

<210> SEQ ID NO 179
<211> LENGTH: 23
<212> TYPE: DNA
<213> ORGANISM: Acidaminococcus sp.

<400> SEQUENCE: 179
aattctttaa gtaatttaag agg 23

<210> SEQ ID NO 180
<211> LENGTH: 23
<212> TYPE: DNA
<213> ORGANISM: Acidaminococcus sp.

<400> SEQUENCE: 180
attgtattgt cataaatttg ggg 23

<210> SEQ ID NO 181
<211> LENGTH: 23
<212> TYPE: DNA
<213> ORGANISM: Acidaminococcus sp.

<400> SEQUENCE: 181
cttagtagtc tcagaaccaa ggg 23

<210> SEQ ID NO 182
<211> LENGTH: 23
<212> TYPE: DNA
<213> ORGANISM: Acidaminococcus sp.

<400> SEQUENCE: 182
aaaggagcac aagtacaaac agg 23

<210> SEQ ID NO 183
<211> LENGTH: 23
<212> TYPE: DNA
<213> ORGANISM: Acidaminococcus sp.

<400> SEQUENCE: 183
aatgatgcag taatcgtgta ggg 23

<210> SEQ ID NO 184
<211> LENGTH: 23
<212> TYPE: DNA
<213> ORGANISM: Acidaminococcus sp.

<400> SEQUENCE: 184
acttgacata gtaagaaaca ggg 23

<210> SEQ ID NO 185
<211> LENGTH: 23
<212> TYPE: DNA
<213> ORGANISM: Acidaminococcus sp.

<400> SEQUENCE: 185
ataaaaggaa ctatttacaa ggg 23

<210> SEQ ID NO 186
<211> LENGTH: 20
<212> TYPE: DNA
<213> ORGANISM: Acidaminococcus sp.

<400> SEQUENCE: 186
gtgctcccat acctgtgctt 20

<210> SEQ ID NO 187
<211> LENGTH: 20
<212> TYPE: DNA
<213> ORGANISM: Acidaminococcus sp.

<400> SEQUENCE: 187
ctcacccaac ctcctgctct 20

<210> SEQ ID NO 188
<211> LENGTH: 21
<212> TYPE: DNA
<213> ORGANISM: Acidaminococcus sp.

<400> SEQUENCE: 188
ggcaggctgg gaacagatta t 21

<210> SEQ ID NO 189
<211> LENGTH: 21
<212> TYPE: DNA
<213> ORGANISM: Acidaminococcus sp.

<400> SEQUENCE: 189
ggcaggctgg gaacagatta t 21

<210> SEQ ID NO 190
<211> LENGTH: 20
<212> TYPE: DNA
<213> ORGANISM: Acidaminococcus sp.

<400> SEQUENCE: 190
tgctgtgtac ccccatttga 20

<210> SEQ ID NO 191
<211> LENGTH: 20
<212> TYPE: DNA
<213> ORGANISM: Acidaminococcus sp.

<400> SEQUENCE: 191
cttcacccaa cttgcactgg 20

<210> SEQ ID NO 192
<211> LENGTH: 21
<212> TYPE: DNA
<213> ORGANISM: Acidaminococcus sp.

<400> SEQUENCE: 192
gtcagctacc tttcccatgt t 21

<210> SEQ ID NO 193
<211> LENGTH: 22
<212> TYPE: DNA
<213> ORGANISM: Acidaminococcus sp.

<400> SEQUENCE: 193
tgaagtgttt acgtcctccc at 22

<210> SEQ ID NO 194
<211> LENGTH: 20
<212> TYPE: DNA
<213> ORGANISM: Acidaminococcus sp.

<400> SEQUENCE: 194
aaaagatgct ggaccttggc 20

<210> SEQ ID NO 195
<211> LENGTH: 20
<212> TYPE: DNA
<213> ORGANISM: Acidaminococcus sp.

<400> SEQUENCE: 195
caggatgagc agcactttgg 20

<210> SEQ ID NO 196
<211> LENGTH: 19
<212> TYPE: DNA
<213> ORGANISM: Acidaminococcus sp.

<400> SEQUENCE: 196
cggggctcct ccaaacctg 19

<210> SEQ ID NO 197
<211> LENGTH: 20
<212> TYPE: DNA
<213> ORGANISM: Acidaminococcus sp.

<400> SEQUENCE: 197
ctccatggag gcagagaggc 20

<210> SEQ ID NO 198
<211> LENGTH: 20
<212> TYPE: DNA
<213> ORGANISM: Acidaminococcus sp.

<400> SEQUENCE: 198
ctgtaacgct taggctgcca 20

<210> SEQ ID NO 199
<211> LENGTH: 20
<212> TYPE: DNA
<213> ORGANISM: Acidaminococcus sp.

<400> SEQUENCE: 199
ctggcctgtg aaaggtacac 20

<210> SEQ ID NO 200
<211> LENGTH: 20
<212> TYPE: DNA
<213> ORGANISM: Acidaminococcus sp.

<400> SEQUENCE: 200
tcaagatgca gaaagtgggc 20

<210> SEQ ID NO 201
<211> LENGTH: 20
<212> TYPE: DNA
<213> ORGANISM: Acidaminococcus sp.

<400> SEQUENCE: 201
cctagagcct ggtgagactt 20

<210> SEQ ID NO 202
<211> LENGTH: 20
<212> TYPE: DNA
<213> ORGANISM: Acidaminococcus sp.

<400> SEQUENCE: 202
acaggtcatc caagagcgag 20

<210> SEQ ID NO 203
<211> LENGTH: 20
<212> TYPE: DNA
<213> ORGANISM: Acidaminococcus sp.

<400> SEQUENCE: 203
aggagaccca agagccatga 20

<210> SEQ ID NO 204
<211> LENGTH: 21
<212> TYPE: DNA
<213> ORGANISM: Acidaminococcus sp.

<400> SEQUENCE: 204
caaggctggg cagagtaact t 21

<210> SEQ ID NO 205
<211> LENGTH: 22
<212> TYPE: DNA
<213> ORGANISM: Acidaminococcus sp.

<400> SEQUENCE: 205
tccctggatt tacagtgggg tg 22

<210> SEQ ID NO 206
<211> LENGTH: 20
<212> TYPE: DNA
<213> ORGANISM: Acidaminococcus sp.

<400> SEQUENCE: 206
gtcgtgatat gagaggcccg 20

<210> SEQ ID NO 207
<211> LENGTH: 20
<212> TYPE: DNA

<213> ORGANISM: Acidaminococcus sp.

<400> SEQUENCE: 207
tcacctggcc cttggatttc 20

<210> SEQ ID NO 208
<211> LENGTH: 20
<212> TYPE: DNA
<213> ORGANISM: Acidaminococcus sp.

<400> SEQUENCE: 208
cactgtcgga gctcacatcg 20

<210> SEQ ID NO 209
<211> LENGTH: 20
<212> TYPE: DNA
<213> ORGANISM: Acidaminococcus sp.

<400> SEQUENCE: 209
gcctccttcc agggttgatg 20

<210> SEQ ID NO 210
<211> LENGTH: 20
<212> TYPE: DNA
<213> ORGANISM: Acidaminococcus sp.

<400> SEQUENCE: 210
gcagaagctg gacttgcctc 20

<210> SEQ ID NO 211
<211> LENGTH: 20
<212> TYPE: DNA
<213> ORGANISM: Acidaminococcus sp.

<400> SEQUENCE: 211
aacccccgag ataggaaggg 20

<210> SEQ ID NO 212
<211> LENGTH: 20
<212> TYPE: DNA
<213> ORGANISM: Acidaminococcus sp.

<400> SEQUENCE: 212
ccgcacctgt ctgtttttgg 20

<210> SEQ ID NO 213
<211> LENGTH: 20
<212> TYPE: DNA
<213> ORGANISM: Acidaminococcus sp.

<400> SEQUENCE: 213
gctagagtgc aatgtcgcga 20

<210> SEQ ID NO 214
<211> LENGTH: 20
<212> TYPE: DNA
<213> ORGANISM: Acidaminococcus sp.

<400> SEQUENCE: 214
caacagtagg cggagagtgg 20

<210> SEQ ID NO 215
<211> LENGTH: 20

<212> TYPE: DNA
<213> ORGANISM: Acidaminococcus sp.

<400> SEQUENCE: 215
gaggccagtt caagaccagc 20

<210> SEQ ID NO 216
<211> LENGTH: 19
<212> TYPE: DNA
<213> ORGANISM: Acidaminococcus sp.

<400> SEQUENCE: 216
gcccttcaag ctgtcaggt 19

<210> SEQ ID NO 217
<211> LENGTH: 20
<212> TYPE: DNA
<213> ORGANISM: Acidaminococcus sp.

<400> SEQUENCE: 217
tctcgccacc tggaacaaag 20

<210> SEQ ID NO 218
<211> LENGTH: 20
<212> TYPE: DNA
<213> ORGANISM: Acidaminococcus sp.

<400> SEQUENCE: 218
gggctctaat ggctgtgtgt 20

<210> SEQ ID NO 219
<211> LENGTH: 20
<212> TYPE: DNA
<213> ORGANISM: Acidaminococcus sp.

<400> SEQUENCE: 219
cttttccctc gacctccacc 20

<210> SEQ ID NO 220
<211> LENGTH: 21
<212> TYPE: DNA
<213> ORGANISM: Acidaminococcus sp.

<400> SEQUENCE: 220
gggaactgcc tccttgcaga a 21

<210> SEQ ID NO 221
<211> LENGTH: 20
<212> TYPE: DNA
<213> ORGANISM: Acidaminococcus sp.

<400> SEQUENCE: 221
tggcaaagtt acatgtccgc 20

<210> SEQ ID NO 222
<211> LENGTH: 23
<212> TYPE: DNA
<213> ORGANISM: Acidaminococcus sp.

<400> SEQUENCE: 222
cgcttttcct aacaggctac tcc 23

<210> SEQ ID NO 223

<211> LENGTH: 21
<212> TYPE: DNA
<213> ORGANISM: Acidaminococcus sp.

<400> SEQUENCE: 223
gcattatgca ccagtttggg g 21

<210> SEQ ID NO 224
<211> LENGTH: 23
<212> TYPE: DNA
<213> ORGANISM: Acidaminococcus sp.

<400> SEQUENCE: 224
acgccctaat gaaattctag ccc 23

<210> SEQ ID NO 225
<211> LENGTH: 20
<212> TYPE: DNA
<213> ORGANISM: Acidaminococcus sp.

<400> SEQUENCE: 225
gctgtgccgg acgatcaaaa 20

<210> SEQ ID NO 226
<211> LENGTH: 23
<212> TYPE: DNA
<213> ORGANISM: Acidaminococcus sp.

<400> SEQUENCE: 226
cctctctgct atgttgctgt tcc 23

<210> SEQ ID NO 227
<211> LENGTH: 20
<212> TYPE: DNA
<213> ORGANISM: Acidaminococcus sp.

<400> SEQUENCE: 227
gccacctgga cttgataggg 20

<210> SEQ ID NO 228
<211> LENGTH: 24
<212> TYPE: DNA
<213> ORGANISM: Acidaminococcus sp.

<400> SEQUENCE: 228
agcacactgg acattagaaa cagg 24

<210> SEQ ID NO 229
<211> LENGTH: 20
<212> TYPE: DNA
<213> ORGANISM: Acidaminococcus sp.

<400> SEQUENCE: 229
gattacaggc gtgcgctacc 20

<210> SEQ ID NO 230
<211> LENGTH: 23
<212> TYPE: DNA
<213> ORGANISM: Acidaminococcus sp.

<400> SEQUENCE: 230
ccaattcctg cgtcttccat gcc 23

<210> SEQ ID NO 231
<211> LENGTH: 22
<212> TYPE: DNA
<213> ORGANISM: Acidaminococcus sp.

<400> SEQUENCE: 231
caacatagca gaggcactgt ag 22

<210> SEQ ID NO 232
<211> LENGTH: 22
<212> TYPE: DNA
<213> ORGANISM: Acidaminococcus sp.

<400> SEQUENCE: 232
gaacccttat ggtgggctgt gg 22

<210> SEQ ID NO 233
<211> LENGTH: 23
<212> TYPE: DNA
<213> ORGANISM: Acidaminococcus sp.

<400> SEQUENCE: 233
gggatgtcag tgctgttgtg cag 23

<210> SEQ ID NO 234
<211> LENGTH: 23
<212> TYPE: DNA
<213> ORGANISM: Acidaminococcus sp.

<400> SEQUENCE: 234
gtctttttcc agcctgagcc agg 23

<210> SEQ ID NO 235
<211> LENGTH: 23
<212> TYPE: DNA
<213> ORGANISM: Acidaminococcus sp.

<400> SEQUENCE: 235
gtctgccaag ctaaggctct cac 23

<210> SEQ ID NO 236
<211> LENGTH: 23
<212> TYPE: DNA
<213> ORGANISM: Acidaminococcus sp.

<400> SEQUENCE: 236
gcttccccag tcttgccagt tgt 23

<210> SEQ ID NO 237
<211> LENGTH: 23
<212> TYPE: DNA
<213> ORGANISM: Acidaminococcus sp.

<400> SEQUENCE: 237
ccactgtacc cttccttgtc cga 23

<210> SEQ ID NO 238
<211> LENGTH: 20
<212> TYPE: DNA
<213> ORGANISM: Acidaminococcus sp.

<400> SEQUENCE: 238
tgtcagtagg cccccaacta 20

<210> SEQ ID NO 239
<211> LENGTH: 21
<212> TYPE: DNA
<213> ORGANISM: Acidaminococcus sp.

<400> SEQUENCE: 239
gcctaactgg caaatgcctt a 21

<210> SEQ ID NO 240
<211> LENGTH: 20
<212> TYPE: DNA
<213> ORGANISM: Acidaminococcus sp.

<400> SEQUENCE: 240
tgaacatggc acctctcctg 20

<210> SEQ ID NO 241
<211> LENGTH: 20
<212> TYPE: DNA
<213> ORGANISM: Acidaminococcus sp.

<400> SEQUENCE: 241
tgttgcgcct tcaatactgt 20

<210> SEQ ID NO 242
<211> LENGTH: 21
<212> TYPE: DNA
<213> ORGANISM: Acidaminococcus sp.

<400> SEQUENCE: 242
gtttgcatgg ccactagaag g 21

<210> SEQ ID NO 243
<211> LENGTH: 21
<212> TYPE: DNA
<213> ORGANISM: Acidaminococcus sp.

<400> SEQUENCE: 243
ctctcacaaa ggcaatggca c 21

<210> SEQ ID NO 244
<211> LENGTH: 20
<212> TYPE: DNA
<213> ORGANISM: Acidaminococcus sp.

<400> SEQUENCE: 244
acagggccat cttgtgacag 20

<210> SEQ ID NO 245
<211> LENGTH: 20
<212> TYPE: DNA
<213> ORGANISM: Acidaminococcus sp.

<400> SEQUENCE: 245
ccgctaaagt gcgaatcacg 20

<210> SEQ ID NO 246
<211> LENGTH: 20
<212> TYPE: DNA
<213> ORGANISM: Acidaminococcus sp.

<400> SEQUENCE: 246
gacggagcag acccatctgc 20

<210> SEQ ID NO 247
<211> LENGTH: 21
<212> TYPE: DNA
<213> ORGANISM: Acidaminococcus sp.

<400> SEQUENCE: 247
gagcctaatg gcccttggca c 21

<210> SEQ ID NO 248
<211> LENGTH: 20
<212> TYPE: DNA
<213> ORGANISM: Acidaminococcus sp.

<400> SEQUENCE: 248
gcccccgtat taccactctg 20

<210> SEQ ID NO 249
<211> LENGTH: 20
<212> TYPE: DNA
<213> ORGANISM: Acidaminococcus sp.

<400> SEQUENCE: 249
ccagtgacat ggccaagatg 20

<210> SEQ ID NO 250
<211> LENGTH: 23
<212> TYPE: DNA
<213> ORGANISM: Acidaminococcus sp.

<400> SEQUENCE: 250
accccttcca ataccatttg aga 23

<210> SEQ ID NO 251
<211> LENGTH: 22
<212> TYPE: DNA
<213> ORGANISM: Acidaminococcus sp.

<400> SEQUENCE: 251
tgcataactc gacagataca ca 22

<210> SEQ ID NO 252
<211> LENGTH: 20
<212> TYPE: DNA
<213> ORGANISM: Acidaminococcus sp.

<400> SEQUENCE: 252
gcccccgtat taccactctg 20

<210> SEQ ID NO 253
<211> LENGTH: 20
<212> TYPE: DNA
<213> ORGANISM: Acidaminococcus sp.

<400> SEQUENCE: 253
ccagtgacat ggccaagatg 20

<210> SEQ ID NO 254
<211> LENGTH: 20
<212> TYPE: DNA
<213> ORGANISM: Acidaminococcus sp.

<400> SEQUENCE: 254
tgtcagtagg cccccaacta 20

<210> SEQ ID NO 255
<211> LENGTH: 21
<212> TYPE: DNA
<213> ORGANISM: Acidaminococcus sp.

<400> SEQUENCE: 255
gcctaactgg caaatgcctt a 21

<210> SEQ ID NO 256
<211> LENGTH: 20
<212> TYPE: DNA
<213> ORGANISM: Acidaminococcus sp.

<400> SEQUENCE: 256
gtccgagaga caagccaggg 20

<210> SEQ ID NO 257
<211> LENGTH: 21
<212> TYPE: DNA
<213> ORGANISM: Acidaminococcus sp.

<400> SEQUENCE: 257
gatcctgctc tctctgcctc c 21

<210> SEQ ID NO 258
<211> LENGTH: 20
<212> TYPE: DNA
<213> ORGANISM: Acidaminococcus sp.

<400> SEQUENCE: 258
gacggagcag acccatctgc 20

<210> SEQ ID NO 259
<211> LENGTH: 21
<212> TYPE: DNA
<213> ORGANISM: Acidaminococcus sp.

<400> SEQUENCE: 259
gagcctaatg gcccttggca c 21

<210> SEQ ID NO 260
<211> LENGTH: 23
<212> TYPE: DNA
<213> ORGANISM: Acidaminococcus sp.

<400> SEQUENCE: 260
cagtcaagtc cagcagttgt ccc 23

<210> SEQ ID NO 261
<211> LENGTH: 21
<212> TYPE: DNA
<213> ORGANISM: Acidaminococcus sp.

<400> SEQUENCE: 261
gagtagggtg gccagaggca g 21

<210> SEQ ID NO 262
<211> LENGTH: 21
<212> TYPE: DNA
<213> ORGANISM: Acidaminococcus sp.

<400> SEQUENCE: 262
cccactccac tttgttccca g 21

<210> SEQ ID NO 263
<211> LENGTH: 20
<212> TYPE: DNA
<213> ORGANISM: Acidaminococcus sp.

<400> SEQUENCE: 263
tcctgggccc aatcattctg 20

<210> SEQ ID NO 264
<211> LENGTH: 20
<212> TYPE: DNA
<213> ORGANISM: Acidaminococcus sp.

<400> SEQUENCE: 264
agggtttgag gggttcagtc 20

<210> SEQ ID NO 265
<211> LENGTH: 20
<212> TYPE: DNA
<213> ORGANISM: Acidaminococcus sp.

<400> SEQUENCE: 265
acttgactcc caactcaggc 20

<210> SEQ ID NO 266
<211> LENGTH: 20
<212> TYPE: DNA
<213> ORGANISM: Acidaminococcus sp.

<400> SEQUENCE: 266
taggtgggca agaacagagg 20

<210> SEQ ID NO 267
<211> LENGTH: 20
<212> TYPE: DNA
<213> ORGANISM: Acidaminococcus sp.

<400> SEQUENCE: 267
ttcagcacag agagggacag 20

<210> SEQ ID NO 268
<211> LENGTH: 20
<212> TYPE: DNA
<213> ORGANISM: Acidaminococcus sp.

<400> SEQUENCE: 268
ctcccaggtt cactccatcc 20

<210> SEQ ID NO 269
<211> LENGTH: 20
<212> TYPE: DNA
<213> ORGANISM: Acidaminococcus sp.

<400> SEQUENCE: 269
ggccacgtat tctaaccagc 20

<210> SEQ ID NO 270
<211> LENGTH: 20
<212> TYPE: DNA
<213> ORGANISM: Acidaminococcus sp.

<400> SEQUENCE: 270
ttggagaagc atcacctgcc 20

<210> SEQ ID NO 271
<211> LENGTH: 20
<212> TYPE: DNA
<213> ORGANISM: Acidaminococcus sp.

<400> SEQUENCE: 271
cgggctgtgt cctaacgaat 20

<210> SEQ ID NO 272
<211> LENGTH: 21
<212> TYPE: DNA
<213> ORGANISM: Acidaminococcus sp.

<400> SEQUENCE: 272
acattcccag tgttccgtga g 21

<210> SEQ ID NO 273
<211> LENGTH: 20
<212> TYPE: DNA
<213> ORGANISM: Acidaminococcus sp.

<400> SEQUENCE: 273
catccagtcc gtcgctaagt 20

<210> SEQ ID NO 274
<211> LENGTH: 20
<212> TYPE: DNA
<213> ORGANISM: Acidaminococcus sp.

<400> SEQUENCE: 274
caccccaaca acttctgggg 20

<210> SEQ ID NO 275
<211> LENGTH: 22
<212> TYPE: DNA
<213> ORGANISM: Acidaminococcus sp.

<400> SEQUENCE: 275
agcatggtgc agaatagtgt gt 22

<210> SEQ ID NO 276
<211> LENGTH: 21
<212> TYPE: DNA
<213> ORGANISM: Acidaminococcus sp.

<400> SEQUENCE: 276
ggattacctg ggagggagtc a 21

<210> SEQ ID NO 277
<211> LENGTH: 20
<212> TYPE: DNA
<213> ORGANISM: Acidaminococcus sp.

<400> SEQUENCE: 277
ggttgatgtc caccccttca 20

<210> SEQ ID NO 278
<211> LENGTH: 20
<212> TYPE: DNA
<213> ORGANISM: Acidaminococcus sp.

<400> SEQUENCE: 278
agggtttgag gggttcagtc 20

<210> SEQ ID NO 279
<211> LENGTH: 20
<212> TYPE: DNA
<213> ORGANISM: Acidaminococcus sp.

<400> SEQUENCE: 279
acttgactcc caactcaggc 20

<210> SEQ ID NO 280
<211> LENGTH: 21
<212> TYPE: DNA
<213> ORGANISM: Acidaminococcus sp.

<400> SEQUENCE: 280
cccactccac tttgttccca g 21

<210> SEQ ID NO 281
<211> LENGTH: 20
<212> TYPE: DNA
<213> ORGANISM: Acidaminococcus sp.

<400> SEQUENCE: 281
tcctgggccc aatcattctg 20

<210> SEQ ID NO 282
<211> LENGTH: 20
<212> TYPE: DNA
<213> ORGANISM: Acidaminococcus sp.

<400> SEQUENCE: 282
agttaatggg tgcagcacac 20

<210> SEQ ID NO 283
<211> LENGTH: 22
<212> TYPE: DNA
<213> ORGANISM: Acidaminococcus sp.

<400> SEQUENCE: 283
tcccagcaag tattcagcaa ca 22

<210> SEQ ID NO 284
<211> LENGTH: 20
<212> TYPE: DNA
<213> ORGANISM: Acidaminococcus sp.

<400> SEQUENCE: 284
gccagcccct gattcttcag 20

<210> SEQ ID NO 285
<211> LENGTH: 22
<212> TYPE: DNA
<213> ORGANISM: Acidaminococcus sp.

<400> SEQUENCE: 285
agtgaattat gttggcttgg ca 22

<210> SEQ ID NO 286
<211> LENGTH: 20
<212> TYPE: DNA

<213> ORGANISM: Acidaminococcus sp.

<400> SEQUENCE: 286
agatgacgag agcacagcct 20

<210> SEQ ID NO 287
<211> LENGTH: 20
<212> TYPE: DNA
<213> ORGANISM: Acidaminococcus sp.

<400> SEQUENCE: 287
gggccactaa gttgcaggtc 20

<210> SEQ ID NO 288
<211> LENGTH: 23
<212> TYPE: DNA
<213> ORGANISM: Acidaminococcus sp.

<400> SEQUENCE: 288
gcagtggctc acacctgtag ttc 23

<210> SEQ ID NO 289
<211> LENGTH: 24
<212> TYPE: DNA
<213> ORGANISM: Acidaminococcus sp.

<400> SEQUENCE: 289
cagatctcca gaattctcct gctg 24

<210> SEQ ID NO 290
<211> LENGTH: 21
<212> TYPE: DNA
<213> ORGANISM: Acidaminococcus sp.

<400> SEQUENCE: 290
taagaagcct atggggagca g 21

<210> SEQ ID NO 291
<211> LENGTH: 23
<212> TYPE: DNA
<213> ORGANISM: Acidaminococcus sp.

<400> SEQUENCE: 291
ggcaaggtcc ctgaacagac atg 23

<210> SEQ ID NO 292
<211> LENGTH: 23
<212> TYPE: DNA
<213> ORGANISM: Acidaminococcus sp.

<400> SEQUENCE: 292
cctcccagcc atgcttcctg tta 23

<210> SEQ ID NO 293
<211> LENGTH: 22
<212> TYPE: DNA
<213> ORGANISM: Acidaminococcus sp.

<400> SEQUENCE: 293
agtttggatg cttgctccct cc 22

<210> SEQ ID NO 294
<211> LENGTH: 20

<212> TYPE: DNA
<213> ORGANISM: Acidaminococcus sp.

<400> SEQUENCE: 294
agttaatggg tgcagcacac 20

<210> SEQ ID NO 295
<211> LENGTH: 22
<212> TYPE: DNA
<213> ORGANISM: Acidaminococcus sp.

<400> SEQUENCE: 295
tcccagcaag tattcagcaa ca 22

<210> SEQ ID NO 296
<211> LENGTH: 20
<212> TYPE: DNA
<213> ORGANISM: Acidaminococcus sp.

<400> SEQUENCE: 296
tggaggttcc aagggaccag 20

<210> SEQ ID NO 297
<211> LENGTH: 20
<212> TYPE: DNA
<213> ORGANISM: Acidaminococcus sp.

<400> SEQUENCE: 297
aagactccag gaggccatgg 20

<210> SEQ ID NO 298
<211> LENGTH: 20
<212> TYPE: DNA
<213> ORGANISM: Acidaminococcus sp.

<400> SEQUENCE: 298
aagccgaaag cctacacctc 20

<210> SEQ ID NO 299
<211> LENGTH: 20
<212> TYPE: DNA
<213> ORGANISM: Acidaminococcus sp.

<400> SEQUENCE: 299
ggacattcga agcccgtgta 20

<210> SEQ ID NO 300
<211> LENGTH: 20
<212> TYPE: DNA
<213> ORGANISM: Acidaminococcus sp.

<400> SEQUENCE: 300
tggaggttcc aagggaccag 20

<210> SEQ ID NO 301
<211> LENGTH: 20
<212> TYPE: DNA
<213> ORGANISM: Acidaminococcus sp.

<400> SEQUENCE: 301
aagactccag gaggccatgg 20

<210> SEQ ID NO 302

<211> LENGTH: 22
<212> TYPE: DNA
<213> ORGANISM: Acidaminococcus sp.

<400> SEQUENCE: 302
cagcgtccca tgcacatttg gg 22

<210> SEQ ID NO 303
<211> LENGTH: 20
<212> TYPE: DNA
<213> ORGANISM: Acidaminococcus sp.

<400> SEQUENCE: 303
gagaggacag cacgggcagg 20

<210> SEQ ID NO 304
<211> LENGTH: 21
<212> TYPE: DNA
<213> ORGANISM: Acidaminococcus sp.

<400> SEQUENCE: 304
gtggccaggg tggaggataa g 21

<210> SEQ ID NO 305
<211> LENGTH: 23
<212> TYPE: DNA
<213> ORGANISM: Acidaminococcus sp.

<400> SEQUENCE: 305
ctctggctcc tttgatacct ccg 23

<210> SEQ ID NO 306
<211> LENGTH: 22
<212> TYPE: DNA
<213> ORGANISM: Acidaminococcus sp.

<400> SEQUENCE: 306
ccatgaccca cagaaactag aa 22

<210> SEQ ID NO 307
<211> LENGTH: 20
<212> TYPE: DNA
<213> ORGANISM: Acidaminococcus sp.

<400> SEQUENCE: 307
tcaccaccat ctcacctttg 20

<210> SEQ ID NO 308
<211> LENGTH: 20
<212> TYPE: DNA
<213> ORGANISM: Acidaminococcus sp.

<400> SEQUENCE: 308
ggaggcattt acagtgcagg 20

<210> SEQ ID NO 309
<211> LENGTH: 20
<212> TYPE: DNA
<213> ORGANISM: Acidaminococcus sp.

<400> SEQUENCE: 309
aatgcaggtg aggccattgt 20

<210> SEQ ID NO 310
<211> LENGTH: 20
<212> TYPE: DNA
<213> ORGANISM: Acidaminococcus sp.

<400> SEQUENCE: 310
ggggacacat tcagacccta 20

<210> SEQ ID NO 311
<211> LENGTH: 20
<212> TYPE: DNA
<213> ORGANISM: Acidaminococcus sp.

<400> SEQUENCE: 311
ctcagtgtga acgcgattgg 20

<210> SEQ ID NO 312
<211> LENGTH: 20
<212> TYPE: DNA
<213> ORGANISM: Acidaminococcus sp.

<400> SEQUENCE: 312
gctccctgtt ttgctccttc 20

<210> SEQ ID NO 313
<211> LENGTH: 20
<212> TYPE: DNA
<213> ORGANISM: Acidaminococcus sp.

<400> SEQUENCE: 313
ccaactccaa gccaagcatt 20

<210> SEQ ID NO 314
<211> LENGTH: 22
<212> TYPE: DNA
<213> ORGANISM: Acidaminococcus sp.

<400> SEQUENCE: 314
gctgtgagga gaaaagagag ca 22

<210> SEQ ID NO 315
<211> LENGTH: 20
<212> TYPE: DNA
<213> ORGANISM: Acidaminococcus sp.

<400> SEQUENCE: 315
gtggtgaaag gccatgaggg 20

<210> SEQ ID NO 316
<211> LENGTH: 19
<212> TYPE: DNA
<213> ORGANISM: Acidaminococcus sp.

<400> SEQUENCE: 316
aggggacccc ctgtagaac 19

<210> SEQ ID NO 317
<211> LENGTH: 20
<212> TYPE: DNA
<213> ORGANISM: Acidaminococcus sp.

<400> SEQUENCE: 317
gggcctcaag tttgttttgc 20

<210> SEQ ID NO 318
<211> LENGTH: 24
<212> TYPE: DNA
<213> ORGANISM: Acidaminococcus sp.

<400> SEQUENCE: 318
atggcttttt caggattcca aact 24

<210> SEQ ID NO 319
<211> LENGTH: 21
<212> TYPE: DNA
<213> ORGANISM: Acidaminococcus sp.

<400> SEQUENCE: 319
gcagccccta cagaaatgag t 21

<210> SEQ ID NO 320
<211> LENGTH: 20
<212> TYPE: DNA
<213> ORGANISM: Acidaminococcus sp.

<400> SEQUENCE: 320
gcaggctggt aactgtgact 20

<210> SEQ ID NO 321
<211> LENGTH: 20
<212> TYPE: DNA
<213> ORGANISM: Acidaminococcus sp.

<400> SEQUENCE: 321
acctgctgca gaactgaagc 20

<210> SEQ ID NO 322
<211> LENGTH: 21
<212> TYPE: DNA
<213> ORGANISM: Acidaminococcus sp.

<400> SEQUENCE: 322
ccaatggtga tgagacagcg t 21

<210> SEQ ID NO 323
<211> LENGTH: 20
<212> TYPE: DNA
<213> ORGANISM: Acidaminococcus sp.

<400> SEQUENCE: 323
gtggagggtg tcctggttct 20

<210> SEQ ID NO 324
<211> LENGTH: 20
<212> TYPE: DNA
<213> ORGANISM: Acidaminococcus sp.

<400> SEQUENCE: 324
ctgccctcca gttgtgactt 20

<210> SEQ ID NO 325
<211> LENGTH: 20
<212> TYPE: DNA
<213> ORGANISM: Acidaminococcus sp.

<400> SEQUENCE: 325
tgccacaagg aatcgatgtt 20

<210> SEQ ID NO 326
<211> LENGTH: 23
<212> TYPE: DNA
<213> ORGANISM: Acidaminococcus sp.

<400> SEQUENCE: 326
tgtctaaggc cacgaccaca agc 23

<210> SEQ ID NO 327
<211> LENGTH: 23
<212> TYPE: DNA
<213> ORGANISM: Acidaminococcus sp.

<400> SEQUENCE: 327
ccttcttggc acttctcggt ggt 23

<210> SEQ ID NO 328
<211> LENGTH: 23
<212> TYPE: DNA
<213> ORGANISM: Acidaminococcus sp.

<400> SEQUENCE: 328
ggcccagaac cttgctcttt gag 23

<210> SEQ ID NO 329
<211> LENGTH: 22
<212> TYPE: DNA
<213> ORGANISM: Acidaminococcus sp.

<400> SEQUENCE: 329
aaggagctgt gctgtgcagg ta 22

<210> SEQ ID NO 330
<211> LENGTH: 22
<212> TYPE: DNA
<213> ORGANISM: Acidaminococcus sp.

<400> SEQUENCE: 330
ctgcaccacc acacctggct aa 22

<210> SEQ ID NO 331
<211> LENGTH: 23
<212> TYPE: DNA
<213> ORGANISM: Acidaminococcus sp.

<400> SEQUENCE: 331
agaacagagc agtgggcaac agg 23

<210> SEQ ID NO 332
<211> LENGTH: 23
<212> TYPE: DNA
<213> ORGANISM: Acidaminococcus sp.

<400> SEQUENCE: 332
agaggggcac tcgggaagag ata 23

<210> SEQ ID NO 333
<211> LENGTH: 23
<212> TYPE: DNA
<213> ORGANISM: Acidaminococcus sp.

<400> SEQUENCE: 333
ggaggacttc ttccctgttg gtc 23

<210> SEQ ID NO 334
<211> LENGTH: 20
<212> TYPE: DNA
<213> ORGANISM: Acidaminococcus sp.

<400> SEQUENCE: 334
aaacagggaa gcgtggaaga 20

<210> SEQ ID NO 335
<211> LENGTH: 21
<212> TYPE: DNA
<213> ORGANISM: Acidaminococcus sp.

<400> SEQUENCE: 335
tgatgcttca cctcagtgtc t 21

<210> SEQ ID NO 336
<211> LENGTH: 21
<212> TYPE: DNA
<213> ORGANISM: Acidaminococcus sp.

<400> SEQUENCE: 336
atgattgggt tctgctgagg g 21

<210> SEQ ID NO 337
<211> LENGTH: 21
<212> TYPE: DNA
<213> ORGANISM: Acidaminococcus sp.

<400> SEQUENCE: 337
agaccaccta aaacattggc t 21

<210> SEQ ID NO 338
<211> LENGTH: 20
<212> TYPE: DNA
<213> ORGANISM: Acidaminococcus sp.

<400> SEQUENCE: 338
ggcctgaccc tccagatctt 20

<210> SEQ ID NO 339
<211> LENGTH: 20
<212> TYPE: DNA
<213> ORGANISM: Acidaminococcus sp.

<400> SEQUENCE: 339
gcactatgcg atctcctggc 20

<210> SEQ ID NO 340
<211> LENGTH: 21
<212> TYPE: DNA
<213> ORGANISM: Acidaminococcus sp.

<400> SEQUENCE: 340
taaacaggga agcgtggaag a 21

<210> SEQ ID NO 341
<211> LENGTH: 21
<212> TYPE: DNA
<213> ORGANISM: Acidaminococcus sp.

<400> SEQUENCE: 341
tgatgcttca cctcagtgtc t 21

<210> SEQ ID NO 342
<211> LENGTH: 21
<212> TYPE: DNA
<213> ORGANISM: Acidaminococcus sp.

<400> SEQUENCE: 342
atgattgggt tctgctgagg g 21

<210> SEQ ID NO 343
<211> LENGTH: 20
<212> TYPE: DNA
<213> ORGANISM: Acidaminococcus sp.

<400> SEQUENCE: 343
gaccacctaa aacattggct 20

<210> SEQ ID NO 344
<211> LENGTH: 20
<212> TYPE: DNA
<213> ORGANISM: Acidaminococcus sp.

<400> SEQUENCE: 344
ggcctgaccc tccagatctt 20

<210> SEQ ID NO 345
<211> LENGTH: 20
<212> TYPE: DNA
<213> ORGANISM: Acidaminococcus sp.

<400> SEQUENCE: 345
gcactatgcg atctcctggc 20

<210> SEQ ID NO 346
<211> LENGTH: 20
<212> TYPE: DNA
<213> ORGANISM: Acidaminococcus sp.

<400> SEQUENCE: 346
acaaatcccc tcatcccaac 20

<210> SEQ ID NO 347
<211> LENGTH: 20
<212> TYPE: DNA
<213> ORGANISM: Acidaminococcus sp.

<400> SEQUENCE: 347
aagctcactc acccaccact 20

<210> SEQ ID NO 348
<211> LENGTH: 23
<212> TYPE: DNA
<213> ORGANISM: Acidaminococcus sp.

<400> SEQUENCE: 348
gcaacaatcg ccattcctca ccc 23

<210> SEQ ID NO 349
<211> LENGTH: 21
<212> TYPE: DNA
<213> ORGANISM: Acidaminococcus sp.

<400> SEQUENCE: 349
tggccctctt atagctctag g 21

<210> SEQ ID NO 350
<211> LENGTH: 24
<212> TYPE: DNA
<213> ORGANISM: Acidaminococcus sp.

<400> SEQUENCE: 350
tttactgatg gtccaaacat ctaa 24

<210> SEQ ID NO 351
<211> LENGTH: 24
<212> TYPE: DNA
<213> ORGANISM: Acidaminococcus sp.

<400> SEQUENCE: 351
tttactgatg gtccatccct ttta 24

<210> SEQ ID NO 352
<211> LENGTH: 24
<212> TYPE: DNA
<213> ORGANISM: Acidaminococcus sp.

<400> SEQUENCE: 352
tttactgatg gtccaaacat ctaa 24

<210> SEQ ID NO 353
<211> LENGTH: 24
<212> TYPE: DNA
<213> ORGANISM: Acidaminococcus sp.

<400> SEQUENCE: 353
tttgctgatg gtcgatttat actg 24

<210> SEQ ID NO 354
<211> LENGTH: 24
<212> TYPE: DNA
<213> ORGANISM: Acidaminococcus sp.

<400> SEQUENCE: 354
tttcctgatg gtccatgtct gtta 24

<210> SEQ ID NO 355
<211> LENGTH: 24
<212> TYPE: DNA
<213> ORGANISM: Acidaminococcus sp.

<400> SEQUENCE: 355
attcctgatg atccatgcct gcat 24

<210> SEQ ID NO 356
<211> LENGTH: 24
<212> TYPE: DNA
<213> ORGANISM: Acidaminococcus sp.

<400> SEQUENCE: 356
tttactgatg gtccaaacat ctaa 24

<210> SEQ ID NO 357
<211> LENGTH: 24
<212> TYPE: DNA
<213> ORGANISM: Acidaminococcus sp.

<400> SEQUENCE: 357
tctcctgatg gtccatacct gtta 24

<210> SEQ ID NO 358
<211> LENGTH: 24
<212> TYPE: DNA
<213> ORGANISM: Acidaminococcus sp.

<400> SEQUENCE: 358
tttagtgata gtccatgtct gcag 24

<210> SEQ ID NO 359
<211> LENGTH: 24
<212> TYPE: DNA
<213> ORGANISM: Acidaminococcus sp.

<400> SEQUENCE: 359
tttactgatg gtccaaacat ctga 24

<210> SEQ ID NO 360
<211> LENGTH: 24
<212> TYPE: DNA
<213> ORGANISM: Acidaminococcus sp.

<400> SEQUENCE: 360
tttgctgatg gtctatagct atca 24

<210> SEQ ID NO 361
<211> LENGTH: 24
<212> TYPE: DNA
<213> ORGANISM: Acidaminococcus sp.

<400> SEQUENCE: 361
tttcctgatg gtccacactt gttg 24

<210> SEQ ID NO 362
<211> LENGTH: 24
<212> TYPE: DNA
<213> ORGANISM: Acidaminococcus sp.

<400> SEQUENCE: 362
tttcctgatg gtctacacct gttg 24

<210> SEQ ID NO 363
<211> LENGTH: 24
<212> TYPE: DNA
<213> ORGANISM: Acidaminococcus sp.

<400> SEQUENCE: 363
tttcctgatg gtctattttt cctt 24

<210> SEQ ID NO 364
<211> LENGTH: 24
<212> TYPE: DNA
<213> ORGANISM: Acidaminococcus sp.

<400> SEQUENCE: 364
tttactgatg gtccaaacat ctaa 24

<210> SEQ ID NO 365
<211> LENGTH: 24
<212> TYPE: DNA

<213> ORGANISM: Acidaminococcus sp.

<400> SEQUENCE: 365
tttcctgatg gtccacacct attg 24

<210> SEQ ID NO 366
<211> LENGTH: 24
<212> TYPE: DNA
<213> ORGANISM: Acidaminococcus sp.

<400> SEQUENCE: 366
tttcatgatg gtccatacct gtta 24

<210> SEQ ID NO 367
<211> LENGTH: 24
<212> TYPE: DNA
<213> ORGANISM: Acidaminococcus sp.

<400> SEQUENCE: 367
tttcctgatg gtccatgtct gaat 24

<210> SEQ ID NO 368
<211> LENGTH: 24
<212> TYPE: DNA
<213> ORGANISM: Acidaminococcus sp.

<400> SEQUENCE: 368
tttgctgatg gtctctttaa ctta 24

<210> SEQ ID NO 369
<211> LENGTH: 24
<212> TYPE: DNA
<213> ORGANISM: Acidaminococcus sp.

<400> SEQUENCE: 369
tttcctgatg gcccatacct gtta 24

<210> SEQ ID NO 370
<211> LENGTH: 24
<212> TYPE: DNA
<213> ORGANISM: Acidaminococcus sp.

<400> SEQUENCE: 370
tttggtgatg gtctatatca gaga 24

<210> SEQ ID NO 371
<211> LENGTH: 24
<212> TYPE: DNA
<213> ORGANISM: Acidaminococcus sp.

<400> SEQUENCE: 371
tttcctgatg gtccacacct tttg 24

<210> SEQ ID NO 372
<211> LENGTH: 24
<212> TYPE: DNA
<213> ORGANISM: Acidaminococcus sp.

<400> SEQUENCE: 372
tttcctgatg gtccacactt gtgg 24

<210> SEQ ID NO 373
<211> LENGTH: 24

<212> TYPE: DNA
<213> ORGANISM: Acidaminococcus sp.

<400> SEQUENCE: 373
tttcctgatg gtccacgcct gtta 24

<210> SEQ ID NO 374
<211> LENGTH: 24
<212> TYPE: DNA
<213> ORGANISM: Acidaminococcus sp.

<400> SEQUENCE: 374
tttcctgatg gtccacactt atta 24

<210> SEQ ID NO 375
<211> LENGTH: 24
<212> TYPE: DNA
<213> ORGANISM: Acidaminococcus sp.

<400> SEQUENCE: 375
tttcctgatg gtccatactt gttg 24

<210> SEQ ID NO 376
<211> LENGTH: 24
<212> TYPE: DNA
<213> ORGANISM: Acidaminococcus sp.

<400> SEQUENCE: 376
tttcctgatg gtccacacct attg 24

<210> SEQ ID NO 377
<211> LENGTH: 24
<212> TYPE: DNA
<213> ORGANISM: Acidaminococcus sp.

<400> SEQUENCE: 377
ttacctgatg ttccatgtcc agtg 24

<210> SEQ ID NO 378
<211> LENGTH: 24
<212> TYPE: DNA
<213> ORGANISM: Acidaminococcus sp.

<400> SEQUENCE: 378
tttcccgatg gtccacatct gtta 24

<210> SEQ ID NO 379
<211> LENGTH: 24
<212> TYPE: DNA
<213> ORGANISM: Acidaminococcus sp.

<400> SEQUENCE: 379
tttactgatg gtccatacct cgta 24

<210> SEQ ID NO 380
<211> LENGTH: 24
<212> TYPE: DNA
<213> ORGANISM: Acidaminococcus sp.

<400> SEQUENCE: 380
tttcctgatg gtccacacct gttg 24

<210> SEQ ID NO 381

<211> LENGTH: 24
<212> TYPE: DNA
<213> ORGANISM: Acidaminococcus sp.

<400> SEQUENCE: 381
tttagtgatg gtccctattt cttc 24

<210> SEQ ID NO 382
<211> LENGTH: 24
<212> TYPE: DNA
<213> ORGANISM: Acidaminococcus sp.

<400> SEQUENCE: 382
tctcctgatg gtccacgcct gtta 24

<210> SEQ ID NO 383
<211> LENGTH: 24
<212> TYPE: DNA
<213> ORGANISM: Acidaminococcus sp.

<400> SEQUENCE: 383
tttcctgatg gtccacacct attg 24

<210> SEQ ID NO 384
<211> LENGTH: 24
<212> TYPE: DNA
<213> ORGANISM: Acidaminococcus sp.

<400> SEQUENCE: 384
tttcctgctg gtccatgtct aata 24

<210> SEQ ID NO 385
<211> LENGTH: 24
<212> TYPE: DNA
<213> ORGANISM: Acidaminococcus sp.

<400> SEQUENCE: 385
tttactgatg atccatgtct aaac 24

<210> SEQ ID NO 386
<211> LENGTH: 24
<212> TYPE: DNA
<213> ORGANISM: Acidaminococcus sp.

<400> SEQUENCE: 386
tttcctgatg gtccatacct gtta 24

<210> SEQ ID NO 387
<211> LENGTH: 24
<212> TYPE: DNA
<213> ORGANISM: Acidaminococcus sp.

<400> SEQUENCE: 387
tttcctgatg gtccacatct gtta 24

<210> SEQ ID NO 388
<211> LENGTH: 24
<212> TYPE: DNA
<213> ORGANISM: Acidaminococcus sp.

<400> SEQUENCE: 388
tttcctgatg gtccacacct tttg 24

<210> SEQ ID NO 389
<211> LENGTH: 24
<212> TYPE: DNA
<213> ORGANISM: Acidaminococcus sp.

<400> SEQUENCE: 389
tttcctgatg gtctgttttt gtag 24

<210> SEQ ID NO 390
<211> LENGTH: 24
<212> TYPE: DNA
<213> ORGANISM: Acidaminococcus sp.

<400> SEQUENCE: 390
tttcctgatg gtctacacct gttg 24

<210> SEQ ID NO 391
<211> LENGTH: 24
<212> TYPE: DNA
<213> ORGANISM: Acidaminococcus sp.

<400> SEQUENCE: 391
tttactgatg gtccaaacat ctaa 24

<210> SEQ ID NO 392
<211> LENGTH: 24
<212> TYPE: DNA
<213> ORGANISM: Acidaminococcus sp.

<400> SEQUENCE: 392
tttgctgatg gtctatagct atca 24

<210> SEQ ID NO 393
<211> LENGTH: 24
<212> TYPE: DNA
<213> ORGANISM: Acidaminococcus sp.

<400> SEQUENCE: 393
tttcctgatg gtctgttttt gtag 24

<210> SEQ ID NO 394
<211> LENGTH: 24
<212> TYPE: DNA
<213> ORGANISM: Acidaminococcus sp.

<400> SEQUENCE: 394
tttcctgatg gtccatgtct gtta 24

<210> SEQ ID NO 395
<211> LENGTH: 24
<212> TYPE: DNA
<213> ORGANISM: Acidaminococcus sp.

<400> SEQUENCE: 395
tttactgatg gtccaaacat ctaa 24

<210> SEQ ID NO 396
<211> LENGTH: 24
<212> TYPE: DNA
<213> ORGANISM: Acidaminococcus sp.

<400> SEQUENCE: 396
tttcctgatg gtctattttt cctt 24

<210> SEQ ID NO 397
<211> LENGTH: 24
<212> TYPE: DNA
<213> ORGANISM: Acidaminococcus sp.

<400> SEQUENCE: 397
tttcctgatg gtccacagat acta 24

<210> SEQ ID NO 398
<211> LENGTH: 24
<212> TYPE: DNA
<213> ORGANISM: Acidaminococcus sp.

<400> SEQUENCE: 398
tttcctgatg gtctacacct gttg 24

<210> SEQ ID NO 399
<211> LENGTH: 24
<212> TYPE: DNA
<213> ORGANISM: Acidaminococcus sp.

<400> SEQUENCE: 399
tttactgatg gtccaaacat ctaa 24

<210> SEQ ID NO 400
<211> LENGTH: 24
<212> TYPE: DNA
<213> ORGANISM: Acidaminococcus sp.

<400> SEQUENCE: 400
tttactgatg gtccatccct ttta 24

<210> SEQ ID NO 401
<211> LENGTH: 24
<212> TYPE: DNA
<213> ORGANISM: Acidaminococcus sp.

<400> SEQUENCE: 401
tttactgatg gtccaaacat ctaa 24

<210> SEQ ID NO 402
<211> LENGTH: 24
<212> TYPE: DNA
<213> ORGANISM: Acidaminococcus sp.

<400> SEQUENCE: 402
tttactgatg gtccaaacat ctaa 24

<210> SEQ ID NO 403
<211> LENGTH: 24
<212> TYPE: DNA
<213> ORGANISM: Acidaminococcus sp.

<400> SEQUENCE: 403
tttactgatg gtccaaacat ctaa 24

<210> SEQ ID NO 404
<211> LENGTH: 24
<212> TYPE: DNA
<213> ORGANISM: Acidaminococcus sp.

<400> SEQUENCE: 404
tttgctgatg gtcgatttat actg 24

<210> SEQ ID NO 405
<211> LENGTH: 24
<212> TYPE: DNA
<213> ORGANISM: Acidaminococcus sp.

<400> SEQUENCE: 405
tttcctcatg gtccatgtca ggac 24

<210> SEQ ID NO 406
<211> LENGTH: 24
<212> TYPE: DNA
<213> ORGANISM: Acidaminococcus sp.

<400> SEQUENCE: 406
ttttctgatg gtccatacct gtta 24

<210> SEQ ID NO 407
<211> LENGTH: 24
<212> TYPE: DNA
<213> ORGANISM: Acidaminococcus sp.

<400> SEQUENCE: 407
attcctgatg atccatgcct gcat 24

<210> SEQ ID NO 408
<211> LENGTH: 24
<212> TYPE: DNA
<213> ORGANISM: Acidaminococcus sp.

<400> SEQUENCE: 408
tttactgatg gtccaaacat ctga 24

<210> SEQ ID NO 409
<211> LENGTH: 24
<212> TYPE: DNA
<213> ORGANISM: Acidaminococcus sp.

<400> SEQUENCE: 409
tttcatgatg gtccatacct gtta 24

<210> SEQ ID NO 410
<211> LENGTH: 24
<212> TYPE: DNA
<213> ORGANISM: Acidaminococcus sp.

<400> SEQUENCE: 410
tttactgatg atccatgtct aaac 24

<210> SEQ ID NO 411
<211> LENGTH: 24
<212> TYPE: DNA
<213> ORGANISM: Acidaminococcus sp.

<400> SEQUENCE: 411
tttcctgatg gtccacactt gttg 24

<210> SEQ ID NO 412
<211> LENGTH: 24
<212> TYPE: DNA
<213> ORGANISM: Acidaminococcus sp.

<400> SEQUENCE: 412
tttcctgatg gtccatgtct gaat 24

<210> SEQ ID NO 413
<211> LENGTH: 24
<212> TYPE: DNA
<213> ORGANISM: Acidaminococcus sp.

<400> SEQUENCE: 413
tttcctgatg gtccacacct attg 24

<210> SEQ ID NO 414
<211> LENGTH: 24
<212> TYPE: DNA
<213> ORGANISM: Acidaminococcus sp.

<400> SEQUENCE: 414
tttcctgatg gtctacacct gttg 24

<210> SEQ ID NO 415
<211> LENGTH: 24
<212> TYPE: DNA
<213> ORGANISM: Acidaminococcus sp.

<400> SEQUENCE: 415
tttcctgatg gtccacgcct gtta 24

<210> SEQ ID NO 416
<211> LENGTH: 24
<212> TYPE: DNA
<213> ORGANISM: Acidaminococcus sp.

<400> SEQUENCE: 416
tttactgatg gtccatacct cgta 24

<210> SEQ ID NO 417
<211> LENGTH: 24
<212> TYPE: DNA
<213> ORGANISM: Acidaminococcus sp.

<400> SEQUENCE: 417
tttcctgatg gtccacactt gttg 24

<210> SEQ ID NO 418
<211> LENGTH: 24
<212> TYPE: DNA
<213> ORGANISM: Acidaminococcus sp.

<400> SEQUENCE: 418
tttcctgatg gtccacacct tttg 24

<210> SEQ ID NO 419
<211> LENGTH: 24
<212> TYPE: DNA
<213> ORGANISM: Acidaminococcus sp.

<400> SEQUENCE: 419
tttcctgatg gtctacacct gttg 24

<210> SEQ ID NO 420
<211> LENGTH: 24
<212> TYPE: DNA
<213> ORGANISM: Acidaminococcus sp.

<400> SEQUENCE: 420
tttcctgatg gtccacactt gtgg 24

<210> SEQ ID NO 421
<211> LENGTH: 24
<212> TYPE: DNA
<213> ORGANISM: Acidaminococcus sp.

<400> SEQUENCE: 421
tttactaatg gtccaaatcc ttca 24

<210> SEQ ID NO 422
<211> LENGTH: 24
<212> TYPE: DNA
<213> ORGANISM: Acidaminococcus sp.

<400> SEQUENCE: 422
tttgctgatg gtctctttaa ctta 24

<210> SEQ ID NO 423
<211> LENGTH: 24
<212> TYPE: DNA
<213> ORGANISM: Acidaminococcus sp.

<400> SEQUENCE: 423
tttgctgatg gtctgtatct gtga 24

<210> SEQ ID NO 424
<211> LENGTH: 24
<212> TYPE: DNA
<213> ORGANISM: Acidaminococcus sp.

<400> SEQUENCE: 424
tctactgatg gtccttattt gttg 24

<210> SEQ ID NO 425
<211> LENGTH: 24
<212> TYPE: DNA
<213> ORGANISM: Acidaminococcus sp.

<400> SEQUENCE: 425
tttcctgatg atctatctat agta 24

<210> SEQ ID NO 426
<211> LENGTH: 24
<212> TYPE: DNA
<213> ORGANISM: Acidaminococcus sp.

<400> SEQUENCE: 426
tttgctgatg gtccccttct ccca 24

<210> SEQ ID NO 427
<211> LENGTH: 24
<212> TYPE: DNA
<213> ORGANISM: Acidaminococcus sp.

<400> SEQUENCE: 427
tctcctgatg atccacatct gtta 24

<210> SEQ ID NO 428
<211> LENGTH: 24
<212> TYPE: DNA
<213> ORGANISM: Acidaminococcus sp.

<400> SEQUENCE: 428
tttcctgatg gtccatactt gttg 24

<210> SEQ ID NO 429
<211> LENGTH: 24
<212> TYPE: DNA
<213> ORGANISM: Acidaminococcus sp.

<400> SEQUENCE: 429
tttcctgctg gtccatgtct aata 24

<210> SEQ ID NO 430
<211> LENGTH: 24
<212> TYPE: DNA
<213> ORGANISM: Acidaminococcus sp.

<400> SEQUENCE: 430
tttcctgatg gtccacacct tttg 24

<210> SEQ ID NO 431
<211> LENGTH: 24
<212> TYPE: DNA
<213> ORGANISM: Acidaminococcus sp.

<400> SEQUENCE: 431
tttcctgatg gtccatacct gtta 24

<210> SEQ ID NO 432
<211> LENGTH: 24
<212> TYPE: DNA
<213> ORGANISM: Acidaminococcus sp.

<400> SEQUENCE: 432
tttcctgatg gtccacacct gctg 24

<210> SEQ ID NO 433
<211> LENGTH: 24
<212> TYPE: DNA
<213> ORGANISM: Acidaminococcus sp.

<400> SEQUENCE: 433
tttcctgatg gtccacatct gtta 24

<210> SEQ ID NO 434
<211> LENGTH: 24
<212> TYPE: DNA
<213> ORGANISM: Acidaminococcus sp.

<400> SEQUENCE: 434
tttcctgatg gtccacacct gctg 24

<210> SEQ ID NO 435
<211> LENGTH: 24
<212> TYPE: DNA
<213> ORGANISM: Acidaminococcus sp.

<400> SEQUENCE: 435
tttcctgatg gcccatacct gtta 24

<210> SEQ ID NO 436
<211> LENGTH: 24
<212> TYPE: DNA
<213> ORGANISM: Acidaminococcus sp.

<400> SEQUENCE: 436
tttcctgatg gtccacacat gtta 24

<210> SEQ ID NO 437
<211> LENGTH: 50
<212> TYPE: DNA
<213> ORGANISM: Artificial Sequence
<220> FEATURE:
<223> OTHER INFORMATION: Synthetic_5'-terminal part of DNMT1

<400> SEQUENCE: 437
gtacgttaat gtttcctgat ggtccatgtc tgttactcgc ctgtcaagtg 50

<210> SEQ ID NO 438
<211> LENGTH: 50
<212> TYPE: DNA
<213> ORGANISM: Artificial Sequence
<220> FEATURE:
<223> OTHER INFORMATION: Synthetic_3'-terminal part of DNMT1

<400> SEQUENCE: 438
catgcaatta caaaggacta ccaggtacag acaatgagcg gacagttcac 50

<210> SEQ ID NO 439
<211> LENGTH: 23
<212> TYPE: RNA
<213> ORGANISM: Artificial Sequence
<220> FEATURE:
<223> OTHER INFORMATION: Synthetic_Essential part of crRNA
<220> FEATURE:
<221> NAME/KEY: misc_feature
<222> LOCATION: (21)
<223> OTHER INFORMATION: Synthetic_n is U, A, G, or C
<220> FEATURE:
<221> NAME/KEY: misc_feature
<222> LOCATION: (22)
<223> OTHER INFORMATION: Synthetic_n is U, A, G, or C
<220> FEATURE:
<221> NAME/KEY: misc_feature
<222> LOCATION: (23)
<223> OTHER INFORMATION: Synthetic_n is U, A, G, or C

<400> SEQUENCE: 439
cugauggucc augucuguua nnn 23

<210> SEQ ID NO 440
<211> LENGTH: 38
<212> TYPE: DNA
<213> ORGANISM: Artificial Sequence
<220> FEATURE:
<223> OTHER INFORMATION: Synthetic_AmpR gene

<400> SEQUENCE: 440
tttatcaggg ttattgtctc atgagcggat acatattt 38

<210> SEQ ID NO 441
<211> LENGTH: 48
<212> TYPE: RNA
<213> ORGANISM: Artificial Sequence
<220> FEATURE:
<223> OTHER INFORMATION: Synthetic_crRNA library
<220> FEATURE:
<221> NAME/KEY: misc_feature
<222> LOCATION: (38)
<223> OTHER INFORMATION: Synthetic_n is U, A, G, or C
<220> FEATURE:
<221> NAME/KEY: misc_feature
<222> LOCATION: (39)

<223> OTHER INFORMATION: Synthetic_n is U, A, G, or C
<220> FEATURE:
<221> NAME/KEY: misc_feature
<222> LOCATION: (40)
<223> OTHER INFORMATION: Synthetic_n is U, A, G, or C
<220> FEATURE:
<221> NAME/KEY: misc_feature
<222> LOCATION: (41)
<223> OTHER INFORMATION: Synthetic_n is U, A, G, or C
<220> FEATURE:
<221> NAME/KEY: misc_feature
<222> LOCATION: (42)
<223> OTHER INFORMATION: Synthetic_n is U, A, G, or C
<220> FEATURE:
<221> NAME/KEY: misc_feature
<222> LOCATION: (43)
<223> OTHER INFORMATION: Synthetic_n is U, A, G, or C
<220> FEATURE:
<221> NAME/KEY: misc_feature
<222> LOCATION: (44)
<223> OTHER INFORMATION: Synthetic_n is U, A, G, or C
<220> FEATURE:
<221> NAME/KEY: misc_feature
<222> LOCATION: (45)
<223> OTHER INFORMATION: Synthetic_n is U, A, G, or C
<220> FEATURE:
<221> NAME/KEY: misc_feature
<222> LOCATION: (46)
<223> OTHER INFORMATION: Synthetic_n is U, A, G, or C
<220> FEATURE:
<221> NAME/KEY: misc_feature
<222> LOCATION: (47)
<223> OTHER INFORMATION: Synthetic_n is U, A, G, or C
<220> FEATURE:
<221> NAME/KEY: misc_feature
<222> LOCATION: (48)
<223> OTHER INFORMATION: Synthetic_n is U, A, G, or C

<400> SEQUENCE: 441
uaauuucuac ucuuguagau ucaggguuau ugucucannn nnnnnnnn 48

<210> SEQ ID NO 442
<211> LENGTH: 28
<212> TYPE: DNA
<213> ORGANISM: Artificial Sequence
<220> FEATURE:
<223> OTHER INFORMATION: on-target

<400> SEQUENCE: 442
tcagggttat tgtctcatga gcggatac 28

<210> SEQ ID NO 443
<211> LENGTH: 49
<212> TYPE: DNA
<213> ORGANISM: Artificial Sequence
<220> FEATURE:
<223> OTHER INFORMATION: on-target (PTK6)

<400> SEQUENCE: 443
aggggcaggt gtttctttcc tgtttgtctt gtgtcttgag agcttggcc 49

<210> SEQ ID NO 444
<211> LENGTH: 49
<212> TYPE: DNA
<213> ORGANISM: Artificial Sequence
<220> FEATURE:
<223> OTHER INFORMATION: on-target (PTK6)

<400> SEQUENCE: 444
tccccgtcca caaagaaagg acaaacagaa cacagaactc tcgaaccgg 49

<210> SEQ ID NO 445
<211> LENGTH: 20
<212> TYPE: DNA
<213> ORGANISM: Artificial Sequence
<220> FEATURE:
<223> OTHER INFORMATION: OT (PTK6)

<400> SEQUENCE: 445
tttcctgttt gtcttgtgtc 20

<210> SEQ ID NO 446
<211> LENGTH: 21
<212> TYPE: DNA
<213> ORGANISM: Artificial Sequence
<220> FEATURE:
<223> OTHER INFORMATION: OF_01 (PTK6)

<400> SEQUENCE: 446
ttttctgttt gtcttgtagt c 21

<210> SEQ ID NO 447
<211> LENGTH: 19
<212> TYPE: DNA
<213> ORGANISM: Artificial Sequence
<220> FEATURE:
<223> OTHER INFORMATION: OF_02 (PTK6)

<400> SEQUENCE: 447
tttcctgttt gtcttgtac 19

<210> SEQ ID NO 448
<211> LENGTH: 18
<212> TYPE: DNA
<213> ORGANISM: Artificial Sequence
<220> FEATURE:
<223> OTHER INFORMATION: OF_03 (PTK6)

<400> SEQUENCE: 448
tttcctgttt cttttgtc 18

<210> SEQ ID NO 449
<211> LENGTH: 22
<212> TYPE: DNA
<213> ORGANISM: Artificial Sequence
<220> FEATURE:
<223> OTHER INFORMATION: OF_04 (PTK6)

<400> SEQUENCE: 449
tttcctgttt gtcttgcatc tc 22

<210> SEQ ID NO 450
<211> LENGTH: 20
<212> TYPE: DNA
<213> ORGANISM: Artificial Sequence
<220> FEATURE:
<223> OTHER INFORMATION: OF_05 (PTK6)

<400> SEQUENCE: 450
tttcctgttt gttttgtgtt 20

<210> SEQ ID NO 451
<211> LENGTH: 19
<212> TYPE: DNA
<213> ORGANISM: Artificial Sequence
<220> FEATURE:
<223> OTHER INFORMATION: OF_06 (PTK6)

<400> SEQUENCE: 451
tttcttgttt gtcttggta 19

<210> SEQ ID NO 452
<211> LENGTH: 21
<212> TYPE: DNA
<213> ORGANISM: Artificial Sequence
<220> FEATURE:
<223> OTHER INFORMATION: OF_07 (PTK6)

<400> SEQUENCE: 452
ttttctggtt gtcttgttgt c 21

<210> SEQ ID NO 453
<211> LENGTH: 18
<212> TYPE: DNA
<213> ORGANISM: Artificial Sequence
<220> FEATURE:
<223> OTHER INFORMATION: OF_08 (PTK6)

<400> SEQUENCE: 453
ttttgtttgt cttgtttt 18

<210> SEQ ID NO 454
<211> LENGTH: 18
<212> TYPE: DNA
<213> ORGANISM: Artificial Sequence
<220> FEATURE:
<223> OTHER INFORMATION: OF_09 (PTK6)

<400> SEQUENCE: 454
tttcctgttt ctcttttc 18

<210> SEQ ID NO 455
<211> LENGTH: 20
<212> TYPE: RNA
<213> ORGANISM: Artificial Sequence
<220> FEATURE:
<223> OTHER INFORMATION: OT (DNMT1)

<400> SEQUENCE: 455
cugauggucc augucuguua 20

<210> SEQ ID NO 456
<211> LENGTH: 20
<212> TYPE: RNA
<213> ORGANISM: Artificial Sequence
<220> FEATURE:
<223> OTHER INFORMATION: OF_01 (DNMT1)

<400> SEQUENCE: 456
gugauggucc augucuguua 20

<210> SEQ ID NO 457
<211> LENGTH: 20
<212> TYPE: RNA
<213> ORGANISM: Artificial Sequence
<220> FEATURE:
<223> OTHER INFORMATION: OF_02 (DNMT1)

<400> SEQUENCE: 457
gagauggucc augucuguua 20

<210> SEQ ID NO 458
<211> LENGTH: 20

<212> TYPE: RNA
<213> ORGANISM: Artificial Sequence
<220> FEATURE:
<223> OTHER INFORMATION: OF_03 (DNMT1)

<400> SEQUENCE: 458
cucauggucc augucuguua 20

<210> SEQ ID NO 459
<211> LENGTH: 20
<212> TYPE: RNA
<213> ORGANISM: Artificial Sequence
<220> FEATURE:
<223> OTHER INFORMATION: OF_04 (DNMT1)

<400> SEQUENCE: 459 cuguugguccaugucuguua 20

<210> SEQ ID NO 460
<211> LENGTH: 20
<212> TYPE: RNA
<213> ORGANISM: Artificial Sequence
<220> FEATURE:
<223> OTHER INFORMATION: OF_05 (DNMT1)

<400> SEQUENCE: 460 cugaagguccaugucuguua 20

<210> SEQ ID NO 461
<211> LENGTH: 20
<212> TYPE: RNA
<213> ORGANISM: Artificial Sequence
<220> FEATURE:
<223> OTHER INFORMATION: OF_06 (DNMT1)

<400> SEQUENCE: 461
cugaucgucc augucuguua 20

<210> SEQ ID NO 462
<211> LENGTH: 20
<212> TYPE: RNA
<213> ORGANISM: Artificial Sequence
<220> FEATURE:
<223> OTHER INFORMATION: OF_07 (DNMT1)

<400> SEQUENCE: 462
cugaugcucc augucuguua 20

<210> SEQ ID NO 463
<211> LENGTH: 20
<212> TYPE: RNA
<213> ORGANISM: Artificial Sequence
<220> FEATURE:
<223> OTHER INFORMATION: OF_08 (DNMT1)

<400> SEQUENCE: 463
cugauggacc augucuguua 20

<210> SEQ ID NO 464
<211> LENGTH: 20
<212> TYPE: RNA
<213> ORGANISM: Artificial Sequence
<220> FEATURE:
<223> OTHER INFORMATION: OF_09 (DNMT1)

<400> SEQUENCE: 464
cugauggugc augucuguua 20

<210> SEQ ID NO 465
<211> LENGTH: 20
<212> TYPE: RNA
<213> ORGANISM: Artificial Sequence
<220> FEATURE:
<223> OTHER INFORMATION: OF_10 (DNMT1)

<400> SEQUENCE: 465
cugauggucg augucuguua 20

<210> SEQ ID NO 466
<211> LENGTH: 20
<212> TYPE: RNA
<213> ORGANISM: Artificial Sequence
<220> FEATURE:
<223> OTHER INFORMATION: OF_11 (DNMT1)

<400> SEQUENCE: 466
cugauggucc uugucuguua 20

<210> SEQ ID NO 467
<211> LENGTH: 20
<212> TYPE: RNA
<213> ORGANISM: Artificial Sequence
<220> FEATURE:
<223> OTHER INFORMATION: OF_12 (DNMT1)

<400> SEQUENCE: 467
cugauggucc aagucuguua 20

<210> SEQ ID NO 468
<211> LENGTH: 20
<212> TYPE: RNA
<213> ORGANISM: Artificial Sequence
<220> FEATURE:
<223> OTHER INFORMATION: OF_13 (DNMT1)

<400> SEQUENCE: 468
cugauggucc aucucuguua 20

<210> SEQ ID NO 469
<211> LENGTH: 20
<212> TYPE: RNA
<213> ORGANISM: Artificial Sequence
<220> FEATURE:
<223> OTHER INFORMATION: OF_14 (DNMT1)

<400> SEQUENCE: 469
cugauugucc augacuguua 20

<210> SEQ ID NO 470
<211> LENGTH: 20
<212> TYPE: RNA
<213> ORGANISM: Artificial Sequence
<220> FEATURE:
<223> OTHER INFORMATION: OF_15 (DNMT1)

<400> SEQUENCE: 470
cugauggucc augugguuua 20

<210> SEQ ID NO 471
<211> LENGTH: 20
<212> TYPE: RNA
<213> ORGANISM: Artificial Sequence

<220> FEATURE:
<223> OTHER INFORMATION: OF_16 (DNMT1)

<400> SEQUENCE: 471
cugauggucc augucaguua 20

<210> SEQ ID NO 472
<211> LENGTH: 20
<212> TYPE: RNA
<213> ORGANISM: Artificial Sequence
<220> FEATURE:
<223> OTHER INFORMATION: OF_17 (DNMT1)

<400> SEQUENCE: 472
cugauggucc augucucuua 20

<210> SEQ ID NO 473
<211> LENGTH: 20
<212> TYPE: RNA
<213> ORGANISM: Artificial Sequence
<220> FEATURE:
<223> OTHER INFORMATION: OF_18 (DNMT1)

<400> SEQUENCE: 473
cugauggucc augucugaua 20

<210> SEQ ID NO 474
<211> LENGTH: 20
<212> TYPE: RNA
<213> ORGANISM: Artificial Sequence
<220> FEATURE:
<223> OTHER INFORMATION: OF_19 (DNMT1)

<400> SEQUENCE: 474
cugauggucc augucuguaa 20

<210> SEQ ID NO 475
<211> LENGTH: 20
<212> TYPE: RNA
<213> ORGANISM: Artificial Sequence
<220> FEATURE:
<223> OTHER INFORMATION: OF_20 (DNMT1)

<400> SEQUENCE: 475
cugauggucc augucuguug 20

<210> SEQ ID NO 476
<211> LENGTH: 27
<212> TYPE: DNA
<213> ORGANISM: Artificial Sequence
<220> FEATURE:
<223> OTHER INFORMATION: cleavage patterns at position 22 of the target strand

<400> SEQUENCE: 476
tttcctgatg gtccatgtct gttactc 27

<210> SEQ ID NO 477
<211> LENGTH: 27
<212> TYPE: RNA
<213> ORGANISM: Artificial Sequence
<220> FEATURE:
<223> OTHER INFORMATION: Synthetic_Essential part of con-crRNA
<220> FEATURE:
<221> NAME/KEY: misc_feature
<222> LOCATION: (21)
<223> OTHER INFORMATION: Synthetic_n is U, A, G, or C

```
<220> FEATURE:
<221> NAME/KEY: misc_feature
<222> LOCATION: (22)
<223> OTHER INFORMATION: Synthetic_n is U, A, G, or C
<220> FEATURE:
<221> NAME/KEY: misc_feature
<222> LOCATION: (23)
<223> OTHER INFORMATION: Synthetic_n is U, A, G, or C

<400> SEQUENCE: 477

uuuccuguuu gucuuguguc nnnuuuu                                    27


<210> SEQ ID NO 478
<211> LENGTH: 29
<212> TYPE: RNA
<213> ORGANISM: Artificial Sequence
<220> FEATURE:
<223> OTHER INFORMATION: Synthetic_Essential part of U-rich crRNA

<400> SEQUENCE: 478

uuuccuguuu gucuuguguc uuuuauuuu                                  29
```